(12) United States Patent
Uchida et al.

(10) Patent No.: US 6,653,330 B2
(45) Date of Patent: Nov. 25, 2003

(54) AMIDE-TYPE TRIAZOLE COMPOUNDS

(75) Inventors: Takuya Uchida, Tokyo (JP); Toshiyuki Konosu, Kawasaki (JP)

(73) Assignee: Sankyo Company, Limited, Tokyo (JP)

(*) Notice: Subject to any disclaimer, the term of this patent is extended or adjusted under 35 U.S.C. 154(b) by 0 days.

(21) Appl. No.: 10/259,944

(22) Filed: Sep. 27, 2002

(65) Prior Publication Data

US 2003/0176480 A1 Sep. 18, 2003

Related U.S. Application Data

(63) Continuation of application No. PCT/JP01/02443, filed on Mar. 27, 2001.

(30) Foreign Application Priority Data

Mar. 27, 2000 (JP) ......................................... 2000-086943

(51) Int. Cl.⁷ ................ A61K 31/4439; A61K 31/4196; A61K 31/428; C07D 405/14; C07D 405/12
(52) U.S. Cl. ........................ 514/340; 514/367; 514/371; 514/377; 514/380; 514/383; 548/163; 548/195; 548/233; 548/246; 548/268.6; 546/272.4
(58) Field of Search .............................. 548/268.6, 163, 548/195, 233, 246, 272.4; 514/383, 340, 367, 371, 377, 380

(56) References Cited

U.S. PATENT DOCUMENTS 5,977,152 A   11/1999   Oida et al.

FOREIGN PATENT DOCUMENTS

| JP | 10-158167 A | 6/1998 |
|---|---|---|
| JP | 10-279567 A | 10/1998 |
| JP | 11-80135 A | 3/1999 |

*Primary Examiner*—Alan L. Rotman
*Assistant Examiner*—Rebecca Anderson
(74) *Attorney, Agent, or Firm*—Frishauf, Holtz, Goodman & Chick, P.C.

(57) ABSTRACT

A compound of formula (I) or a pharmacologically acceptable prodrug or salt thereof which exhibits excellent antifungal activity:

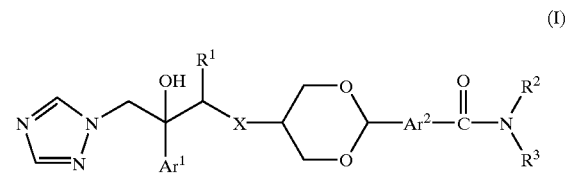

(I)

wherein $Ar^1$ represents a phenyl group or the like; $Ar^2$ represents a phenylene group or the like. X represents a sulfur atom or a methylene group. $R^1$ represents a hydrogen atom or a $C_{1-3}$ alkyl group; $R^2$ represents a hydrogen atom or a $C_{1-3}$ alkyl group; and $R^3$ represents an optionally substituted $C_{6-10}$ aryl group or the like. Fungal infections may be prevented and/or treated by administering said compound (I) or said prodrug or salt thereof.

30 Claims, No Drawings

AMIDE-TYPE TRIAZOLE COMPOUNDS

This appliction is a continuation application of International Application PCT/JP01/02443 filed Mar. 27, 2001.

The present invention relates to amide-type triazole compounds which have excellent antifungal activity or pharmacologically acceptable prodrugs thereof or salts thereof; to medicaments (particularly antifungal agents) containing these compounds as active ingredients; to pharmaceutical compositions for treatment of fungal infections which contain these compounds; to the use of these compounds in the manufacture of medicaments (particularly antifungal agents); and to a method for the prevention or treatment of fungal infections which comprises administering these compounds to a warm-blooded animal (particularly a human) in need thereof.

BACKGROUND OF THE INVENTION

A lot of triazole-type compounds have been known as agents for the treatment of fungal infections in a human or animal. One of the most popular triazole-type compounds is fluconazole. However there have been fungal infections which cannot be clinically treated with fluconazole and there is a need for further compounds having more excellent antifungal activity.

Similar compounds to those of the present invention are disclosed in Japanese Patent Application Publication Nos. Hei-8-333350, Hei-10-279567 and Hei-11-80135.

The present inventors have made a great effort to find compounds having an excellent antifungal activity and found that the compounds of formula (I) (hereinafter referred to as compounds (I)) and pharmacologically acceptable prodrugs thereof and salts thereof exhibit excellent antifungal activity. Thereby the present invention has been completed.

SUMMARY OF THE INVENTION

The present invention relates to:

(1) an amide-type triazole compound (I) or a pharmacologically acceptable prodrug thereof or a salt thereof:

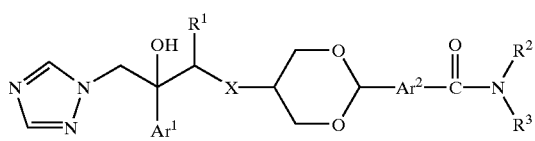

(I)

wherein:
Ar$^1$ represents a phenyl group or a phenyl group substituted with 1 to 3 substituents (said substituents are selected from a halogen atom and a trifluoromethyl group);
Ar$^2$ represents a phenylene group, a phenylene group substituted with 1 or 2 substituents (said substituents are selected from a fluorine atom and a chlorine atom), a naphthylene group or a naphthylene group substituted with 1 or 2 substituents (said substituents are selected from a fluorine atom and a chlorine atom);
X represents a sulfur atom or a methylene group;
R$^1$ represents a hydrogen atom or a C$_{1-3}$ alkyl group;
R$^2$ represents a hydrogen atom or a C$_{1-3}$ alkyl group;
R$^3$ represents a C$_{6-10}$ aryl group, a C$_{6-10}$ aryl group substituted with 1 to 5 substituents selected from substituent group A, a heteroaryl group, a heteroaryl group substituted with 1 or 2 substituents selected from substituent group A, a C$_{7-14}$ aralkyl group, and a C$_{7-14}$ aralkyl group substituted with 1 to 5 substituents selected from substituent group A;
substituent group A comprises a C$_{1-6}$ alkyl group, a C$_{1-6}$ alkyl group substituted with 1 to 5 substituents (said substituents are selected from a halogen atom, a hydroxyl group, a cyano group and a C$_{1-6}$ alkoxy group), a C$_{1-6}$ alkoxy group, a C$_{1-6}$ alkoxy group substituted with 1 to 5 substituents (said substituents are selected from a halogen atom, a hydroxyl group, a cyano group and a C$_{1-6}$ alkoxy group), a C$_{1-6}$ alkanoyl group, a C$_{2-6}$ alkanoyl group substituted with 1 to 5 substituents (said substituents are selected from a halogen atom, a hydroxyl group, a cyano group and a C$_{1-6}$ alkoxy group), a C$_{1-6}$ alkanoyloxy group, a C$_{2-6}$ alkanoyloxy group substituted with 1 to 5 substituents (said substituents are selected from a halogen atom, a hydroxyl group, a cyano group and a C$_{1-6}$ alkoxy group), a halogen atom, a hydroxyl group, an amino group, a mercapto group, a carbamoyl group, a nitro group, a cyano group, a carboxyl group, a group of formula —S(O)$_n$R$^4$ (wherein R$^4$ represents a C$_{1-6}$ alkyl group or a C$_{1-6}$ alkyl group substituted with 1 to 5 substituents (said substituents are selected from halogen atoms), and n represents 0, 1, or 2), a C$_{2-6}$ alkenyl group, a C$_{2-6}$ alkynyl group, a C$_{3-6}$ cycloalkyl group and a (C$_{3-6}$ cycloalkyl)C$_{1-6}$ alkyl group; and (2) a medicament containing an amide-type triazole compound or a pharmacologically acceptable prodrug thereof or a salt thereof described in (1) as an active ingredient.

In the above description:
The "halogen atom" in the definitions of the substituent of Ar$^1$ and the substituent group A is, for example, a fluorine, chlorine, bromine and iodine atom; preferably a fluorine or chlorine atom; and most preferably a fluorine atom.

The "C$_{1-3}$ alkyl group" in the definitions of R$^1$ and R$^2$ is a straight or branched chain alkyl group having 1 to 3 carbons, for example, a methyl, ethyl, propyl or isopropyl group; preferably a methyl or ethyl group; and most preferably a methyl group.

The "C$_{6-10}$ aryl group" in the definition of R$^3$ is an aromatic hydrocarbon group having 6 to 10 carbons, for example a phenyl, indenyl or naphthyl group, preferably a phenyl group.

The "heteroaryl group" in the definition of R$^3$ is a monocyclic aromatic heterocyclyl group or a fused aromatic heterocyclyl group. The "monocyclic aromatic heterocyclyl group" is a 5- or 6-membered aromatic heterocyclyl group containing 1 to 4 nitrogen, oxygen or sulfur atoms, for example, a furyl, thienyl, pyrrolyl, pyrazolyl, imidazolyl, oxazolyl, isoxazolyl, thiazolyl, triazolyl, tetrazolyl, pyridyl, pyrimidyl, pyridazinyl or pyrazyl group; preferably pyridyl or thiazolyl. The "fused aromatic heterocyclyl group" is a 5- or 6-membered aromatic heterocyclyl group which contains 1 to 4 nitrogen, oxygen or sulfur atoms and is fused to 1 or 2 benzene rings or to 5- or 6-membered aromatic heterocyclyl groups containing 1 to 4 nitrogen, oxygen or sulfur atoms. Examples of such a fused heterocyclyl group include isobenzofuranyl, chromenyl, xanthenyl, phenoxathynyl, indolizinyl, isoindolyl, indolyl, indazolyl, purinyl, quinolizinyl, isoquinolyl, quinolyl, phthalazinyl, naphthyridinyl, quinoxalinyl, quinazolinyl, carbazolyl, carbolinyl, acridinyl, isoindolinyl and benzothiazolyl; preferably benzothiazolyl.

A preferred heteroaryl group is a 5- or 6-membered aromatic heterocyclyl group having 1 or 2 nitrogen, oxygen or sulfur atoms or a bicyclic heterocyclyl group which is a 5- or 6-membered aromatic heterocyclyl group that has 1 or 2 nitrogen, oxygen or sulfur atoms and is fused to a benzene ring. A more preferred heteroaryl group is a furyl, thienyl, pyridyl, isoxazolyl, thiazolyl or benzothiazolyl group; and most preferred is a pyridyl, thiazolyl or benzothiazolyl group.

The "$C_{7-14}$ aralkyl group" in the definition of $R^3$ is a $C_{1-4}$ alkyl group substituted with a $C_{6-10}$ aryl group. The "$C_{6-10}$ aryl group" has the same meaning as described above. The "$C_{1-4}$ alkyl group" is a straight or branched chain alkyl group having 1 to 4 carbons, for example, a methyl, ethyl, propyl, isopropyl, butyl, isobutyl, or t-butyl group; preferably a methyl or ethyl group and most preferably a methyl group. The "$C_{7-14}$ aralkyl group" is, for example, a benzyl, phenethyl, phenylpropyl, phenylbutyl, naphthylmethyl, naphthylethyl, or naphthylbutyl group; preferably a benzyl or phenethyl group and more preferably a benzyl group.

In addition the aryl ring of the "$C_{6-10}$ aryl group" and the "$C_{7-14}$ aralkyl group" in the definition of $R^3$ is optionally substituted with 1 to 5 substituents selected from substituent group A and the "heteroaryl group" in the definition of $R^3$ is optionally substituted with 1 or 2 substituents selected from substituent group A.

The "$C_{1-6}$ alkyl group" in the definition of substituent group A (with the proviso that the "$C_{1-6}$ alkyl group" in the definition of $R^4$ is not included) is a straight or branched chain alkyl group having 1 to 6 carbons, for example, a methyl, ethyl, propyl, isopropyl, butyl, isobutyl, s-butyl, t-butyl, pentyl or hexyl group; preferably a $C_{1-3}$ alkyl group; and more preferably a methyl group.

The "$C_{1-6}$ alkyl group substituted with 1 to 5 substituents (said substituents are selected from a halogen atom, a hydroxyl group, a cyano group and a $C_{1-6}$ alkoxy group)" in the definition of substituent group A is a straight or branched chain alkyl group having 1 to 6 carbons substituted with 1 to 5 substituents, said substituents being selected from a halogen atom, a hydroxyl group, a cyano group and a $C_{1-6}$ alkoxy group, for example, a chloromethyl, dichloromethyl, trichloromethyl, chloroethyl, dichloroethyl, trichloroethyl, tetrachloroethyl, chloropropyl, chlorobutyl, chloropentyl, chlorohexyl, fluoromethyl, difluoromethyl, trifluoromethyl, fluoroethyl, difluoroethyl, trifluoroethyl, tetrafluoroethyl, pentafluoroethyl, fluoropropyl, difluoropropyl, trifluoropropyl, tetrafluoropropyl, pentafluoropropyl, pentafluorobutyl, pentafluoropentyl, pentafluorohexyl, bromomethyl, bromoethyl, dibromoethyl, bromopropyl, hydroxymethyl, hydroxyethyl, dihydroxyethyl, hydroxyprbpyl, dihydroxypropyl, hydroxybutyl, hydroxypentyl, hydroxyhexyl, hydroxydifluoromethyl, hydroxydifluoroethyl, hydroxytetrafluoropropyl, hydroxytetrafluorobutyl, hydroxytetrafluoropentyl, hydroxytetrafluorohexyl, hydroxychloroethyl, hydroxychloropropyl, cyanomethyl, cyanoethyl, cyanopropyl, cyanobutyl, cyanopentyl, cyanohexyl, cyanodifluoromethyl, cyanodifluoroethyl, cyanotetrafluoropropyl, cyanotetrafluorobutyl, cyanotetrafluoropentyl, cyanotetrafluorohexyl, cyanohydroxyethyl, cyanohydroxypropyl, cyanohydroxybutyl, cyanohydroxypentyl, cyanohydroxyhexyl, methoxymethyl, methoxyethyl or the like.

A preferred "$C_{1-6}$ alkyl group substituted with 1 to 5 substituents (said substituents are selected from a halogen atom, a hydroxyl group, a cyano group and a $C_{1-6}$ alkoxy group)" is an alkyl group having 1 to 6 carbons substituted with 1 to 4 substituents (said substituents being selected from a halogen atom, a hydroxyl group and a cyano group). An alkyl group having 1 to 4 carbons substituted with 1 to 4 substituents (said substituents being selected from a fluorine atom, a chlorine atom, a hydroxyl group and a cyano group), for example, a fluoromethyl, difluoromethyl, trifluoromethyl, 2-fluoroethyl, 2,2,2-trifluoroethyl, 1,1,2,2-tetrafluoroethyl, pentafluoroethyl, 3-fluoropropyl, trichloromethyl, 2-chloroethyl, 3-chloropropyl, 2-hydroxyethyl, 3-hydroxypropyl, 2,3-dihydroxypropyl, 1-hydroxy-1-methylethyl, 1-methyl-3-hydroxypropyl, 1-methyl-2-hydroxypropyl, 1-methyl-1-hydroxypropyl, or cyanomethyl group is more preferred. A trifluoromethyl or cyanomethyl group is most preferred.

The "$C_{1-6}$ alkoxy group" in the definitions of substituent group A and a substituent moiety of the substituent group A is a straight or branched chain alkoxy group having 1 to 6 carbons, for example, a methoxy, ethoxy, propoxy, isopropoxy, butoxy, isobutoxy, s-butoxy, t-butoxy, pentyloxy or hexyloxy group. A preferred "$C_{1-6}$ alkoxy group" is an alkoxy group having 1 to 3 carbons and a methoxy or ethoxy group is more preferred.

The "$C_{1-6}$ alkoxy group substituted with 1 to 5 substituents (said substituents are selected from a halogen atom, a hydroxyl group, a cyano group and a $C_{1-6}$ alkoxy group)" is a straight or branched chain alkoxy group having 1 to 6 carbons substituted with 1 to 5 substituents, said substituents being selected from a halogen atom, a hydroxyl group and a cyano group, for example, a chloromethoxy, dichloromethoxy, trichloromethoxy, chloroethoxy, dichloroethoxy, trichloroethoxy, chloropentyloxy, chlorohexyloxy, fluoromethoxy, difluoromethoxy, trifluoromethoxy, fluoroethoxy, difluoroethoxy, trifluoroethoxy, tetrafluoroethoxy, pentafluoroethoxy, fluoropropoxy, tetrafluoropropoxy, fluoropentyloxy, fluorohexyloxy, trifluoropropoxy, tetrafluoropropoxy, bromomethoxy, bromoethoxy, bromopropoxy, bromobutoxy, bromopentyloxy, bromohexyloxy, hydroxyethyloxy, hydroxypropyloxy, dihydroxypropyloxy, hydroxybutyloxy, hydroxypentyloxy, hydroxyhexyloxy, hydroxyfluoroethoxy, hydroxydifluoroethoxy, hydroxyfluoropropoxy, hydroxytetrafluoropropoxy, hydroxytetrafluorobutoxy, hydroxytetrafluoropentyloxy, hydroxychloroethoxy, hydroxydichloroethoxy, cyanofluoroethoxy, cyanodifluoroethoxy, cyanofluoropropoxy, cyanotetrafluoropropoxy, cyanotetrafluorobutoxy, cyanotetrafluoropentyloxy, (hydroxymethyl)hydroxyethoxy, methoxymethoxy, or t-butoxymethoxy group.

A preferred "$C_{1-6}$ alkoxy group substituted with 1 to 5 substituents (said substituents are selected from a halogen atom, a hydroxyl group, a cyano group and a $C_{1-6}$ alkoxy group)" is an alkoxy group having 1 to 4 carbons substituted with 1 to 5 substituents (said substituents are selected from a halogen atom, a hydroxyl group and a cyano group). An alkoxy group having 1 to 4 carbons substituted with 1 to 5 substituents (said substituents being selected from a fluorine atom, a chlorine atom and a hydroxyl group), for example, a chloromethoxy, dichloromethoxy, trichloromethoxy, 2-chloroethoxy, 2,2-dichloroethoxy, 2,2,2-trichloroethoxy, 3-chloropropoxy, fluoromethoxy, difluoromethoxy, trifluoromethoxy, 2-fluoroethoxy, 2,2-difluoroethoxy, 2,2,2-trifluoroethoxy, 1,1,2,2-tetrafluoroethoxy, pentafluoroethoxy, 3-fluoropropoxy, 2,2,3,3-tetrafluoropropoxy, 2-hydroxyethyloxy, 3-hydroxypropyloxy, 4-hydroxybutyloxy, (1-ethyl-3- hydroxypropyl)oxy, (1-ethyl-2-hydroxypropyl)oxy, 2-hydroxy-1,1-difluoroethoxy, 4-hydroxy-2,2,3,3-tetrafluorobutoxy, or 1-(hydroxymethyl)-2-hydroxyethoxy group is more preferred. A trifluoromethoxy or tetrafluoropropoxy group is most preferred.

The "$C_{1-6}$ alkanoyl group" in the definition of substituent group A represents a straight or branched chain alkanoyl group having 1 to 6 carbons, for example, a formyl, acetyl, propionyl, butyryl, isobutyryl, valeryl, isovaleryl, pivaloyl or hexanoyl group. A preferred "$C_{1-6}$ alkanoyl group" is an alkanoyl group-having 1 to 3 carbons, and an acetyl group is more preferred.

The "$C_{2-6}$ alkanoyl group substituted with 1 to 5 substituents (said substituents are selected from a halogen atom, a hydroxyl group, a cyano group and a $C_{1-6}$ alkoxy group)" in the definition of substituent group A is a straight or branched chain alkanoyl group having 2 to 6 carbons substituted with 1 to 5 substituents, said substituents being selected from a halogen atom, a hydroxyl group, a cyano group and a $C_{1-6}$ alkoxy group, for example, a hydroxyacetyl, fluoroacetyl, difluoroacetyl, trifluoroacetyl, cyanoacetyl, hydroxypropionyl, fluoropropionyl, difluoropropionyl, trifluoropropionyl, chloropropionyl, bromopropionyl, chlorobutyryl, fluorobutyryl, difluorobutyryl, trifluorobutyryl, fluorohydroxybutyryl, difluorohydroxybutyryl, cyanobutyryl, (hydroxymethyl)methylpropionyl, hydroxyvaleryl, cyanovaleryl, fluorovaleryl, hydroxyhexanoyl, or methoxyacetyl group.

A preferred "$C_{2-6}$ alkanoyl group substituted with 1 to 5 substituents (said substituents are selected from a halogen atom, a hydroxyl group, a cyano group and a $C_{1-6}$ alkoxy group)" is an alkanoyl group having 2 to 6 carbons substituted with 1 to 4 substituents (said substituents are selected from a halogen atom, a hydroxyl group and a cyano group). An alkanoyl group having 2 to 4 carbons substituted with 1 to 3 substituents (said substituents are selected from a fluorine atom and a hydroxyl group), for example, a hydroxyacetyl, fluoroacetyl, difluoroacetyl, trifluoroacetyl, 2-hydroxypropionyl, 3-hydroxypropionyl, 2-hydroxybutyryl, 3-hydroxybutyryl, 4-hydroxybutyryl, or 2-methyl-2-hydroxypropionyl group is more preferred. A trifluoroacetyl group is most preferred.

The "$C_{1-6}$ alkanoyloxy group" in the definition of substituent group A is a straight or branched chain alkanoyloxy group having 1 to 6 carbons, for example, a formyloxy, acetoxy, propionyloxy, butyryloxy, isobutyryloxy, valeryloxy, isovaleryloxy, pivaloyloxy or hexanoyloxy group. A preferred "$C_{1-6}$ alkanoyloxy group" is an alkanoyloxy group having 1 to 3 carbons. A more preferred group is an acetoxy group.

The "$C_{2-6}$ alkanoyloxy group substituted with 1 to 5 substituents (said substituents are selected from a halogen atom, a hydroxyl group, a cyano group and a $C_{1-6}$ alkoxy group)" in the definition of substituent group A is a straight or branched chain alkanoyloxy group having 2 to 6 carbons substituted with 1 to 5 substituents, said substituents being selected from a halogen atom, a hydroxyl group, a cyano group and a $C_{1-6}$ alkoxy group, for example, a hydroxyacetoxy, fluoroacetoxy, difluoroacetoxy, trifluoroacetoxy, cyanoacetoxy, hydroxypropionyloxy, fluoropropionyloxy, difluoropropionyloxy, trifluoropropionyloxy, chloropropionyloxy, bromopropionyloxy, hydroxybutyryloxy, chlorobutyryloxy, fluorobutyryloxy, difluorobutyryloxy, trifluorobutyryloxy, fluorohydroxybutyryloxy, difluorohydroxybutyryloxy, cyanobutyryloxy, (hydroxymethyl)methylpropionyloxy, hydroxyvaleryloxy, cyanovaleryloxy, fluorovaleryloxy, hydroxyhexanoyloxy or methoxyacetyloxy group.

A preferred "$C_{2-6}$ alkanoyloxy group substituted with 1 to 5 substituents (said substituents are selected from a halogen atom, a hydroxyl group, a cyano group and a $C_{1-6}$ alkoxy group)" is an alkanoyloxy group having 2 to 6 carbons substituted with 1 to 4 substituents (said substituents are selected from a halogen atom, a hydroxyl group and a cyano group). An alkanoyloxy group having 2 to 6 carbons substituted with 1 to 4 substituents (said substituents are hydroxyl groups), for example, a hydroxyacetoxy, hydroxypropionyloxy, hydroxybutyryloxy, hydroxyvaleryloxy, or hydroxyhexanoyloxy group is more preferred. A hydroxyacetoxy or hydroxypropionyloxy group is most preferred.

The "$C_{1-6}$ alkyl group" in the definition of $R^4$ represents a straight or branched chain alkyl group having 1 to 6 carbons and the "$C_{1-6}$ alkyl group substituted with 1 to 5 substituents" in the definition of $R^4$ represents a straight or branched chain alkyl group having 1 to 6 carbons substituted with 1 to 5 substituents which are the same or different halogen atoms. $R^4$ is, for example, a methyl, ethyl, propyl, isopropyl, butyl, isobutyl, s-butyl, t-butyl, pentyl, hexyl, chloromethyl, dichloromethyl, trichloromethyl, chloroethyl, dichloroethyl, trichloroethyl, tetrachloroethyl, chloropropyl, chlorobutyl, chloropentyl, chlorohexyl, fluoromethyl, difluoromethyl, trifluoromethyl, fluoroethyl, difluoroethyl, trifluoroethyl, tetrafluoroethyl, pentafluoroethyl, fluoropropyl, difluoropropyl, trifluoropropyl, tetrafluoropropyl, bromomethyl, bromoethyl, dibromoethyl, bromopropyl, or the like. Preferably $R^4$ is an alkyl group having 1 to 3 carbon atoms or an alkyl group having 1 to 3 carbon atoms substituted with 1 to 5 substituents (said substituents are fluorine atoms), for example methyl, ethyl, propyl, isopropyl, fluoromethyl, difluoromethyl, trifluoromethyl, 2-fluoroethyl, 2,2,2-trifluoroethyl, pentafluoroethyl or the like. A methyl or trifluoromethyl group is more preferred.

The "$C_{2-6}$ alkenyl group" in the definition of substituent group A is a straight or branched chain alkenyl group having 2 to 6 carbons and one double bond, for example ethenyl, propenyl, methylpropenyl, ethylpropenyl, butenyl, methylbutenyl, ethylbutenyl, pentenyl, methylpentenyl, hexenyl or the like.

The "$C_{2-6}$ alkynyl group" in the definition of substituent group A is a straight or branched chain alkynyl group having 2 to 6 carbons and one triple bond, for example ethynyl, propynyl, methylpropynyl, ethylpropynyl, butynyl, methylbutynyl, ethylbutynyl, pentynyl, methylpentynyl, hexynyl, or the like.

The "$C_{3-6}$ cycloalkyl group" in the definition of substituent group A is a saturated aliphatic cyclic hydrocarbon group having 3 to 6 carbons, for example cyclopropyl, cyclobutyl, cyclopentyl, cyclohexyl or the like.

The "($C_{3-6}$ cycloalkyl)$C_{1-6}$ alkyl group" in the definition of substituent group A is a $C_{1-6}$ alkyl group substituted with one $C_{3-6}$ cycloalkyl group, for example, a cyclopropylmethyl, cyclobutylmethyl, cyclopentylmethyl, cyclopentylethyl, cyclopentylbutyl, cyclohexylmethyl, cyclohexylethyl, cyclohexylpropyl, cyclohexylbutyl, cyclohexylhexyl group or the like.

Preferably, substituent group A is substituent group Al which comprises a $C_{1-6}$ alkyl group, a $C_{1-6}$ alkyl group substituted with 1 to 4 substituents (said substituents are selected from a halogen atom, a hydroxyl group and a cyano group), a $C_{1-6}$ alkoxy group, a $C_{1-6}$ alkoxy group substituted with 1 to 5 substituents (said substituents are selected from a halogen atom, a hydroxyl group and a cyano group), a $C_{1-6}$ alkanoyl group, a $C_{2-6}$ alkanoyl group substituted with 1 to 4 substituents (said substituents are selected from a halogen atom, a hydroxyl group and a cyano group), a $C_{1-6}$ alkanoyloxy group, a $C_{2-6}$ alkanoyloxy group substituted with 1 to 4 substituents (said substituents are selected from a halogen atom, a hydroxyl group and a cyano group), a halogen atom, a hydroxyl group, a carbamoyl group, a nitro group, a cyano group, a carboxyl group, and a group of formula —S(O)$_n$R$^4$ (wherein R$^4$ represents a $C_{1-6}$ alkyl group or a $C_{1-6}$ alkyl group substituted with 1 to 5 substituents (said substituents are selected from halogen atoms), and n represents 0, 1 or 2).

More preferably, substituent group A is substituent group A2 which comprises a $C_{1-3}$ alkyl group, a $C_{1-4}$ alkyl group substituted with 1 to 4 substituents (said substituents are selected from a fluorine atom, a chlorine atom, a hydroxyl group and a cyano group), a $C_{1-3}$ alkoxy group, a $C_{1-4}$ alkoxy group substituted with 1 to 5 substituents (said substituents are selected from a fluorine atom, a chlorine atom and a hydroxyl group), a $C_{1-3}$ alkanoyl group, a $C_{2-4}$ alkanoyl group substituted with 1 to 3 substituents (said substituents are selected from a fluorine atom and a hydroxyl group), a $C_{1-3}$ alkanoyloxy group, a $C_{2-4}$ alkanoyloxy group substituted with 1 to 4 substituents (said substituents are hydroxyl groups), a halogen atom, a hydroxyl group, a carbamoyl group, a nitro group, a cyano group, a carboxyl group, and a group of formula —S(O)$_n$R$^4$ (wherein R$^4$ represents a $C_{1-3}$ alkyl group, or a $C_{1-3}$ alkyl group substituted with 1 to 5 substututients (said substituents are fluorine atoms); and n represents 0, 1 or 2).

Most preferably, substituent group A is substituent group A3 which comprises a methyl group, a trifluoromethyl group, a cyanomethyl group, a trifluoromethoxy group, a tetrafluoropropoxy group, an acetyl group, an acetoxy group, a fluorine atom, a chlorine atom, a bromine atom, an iodine atom, a hydroxyl group, a carbamoyl group, a nitro group, a cyano group, a carboxyl group, a trifluoromethylthio group, a methanesulfonyl group and a trifluoromethanesulfonyl group.

When a moiety selected from substituent group A to A3 has substituents, a preferred number of substituents is 1 or 2.

Ar$^1$ is, for example, a phenyl, fluorophenyl, chlorophenyl, bromophenyl, iodophenyl, (trifluoromethyl)phenyl, chlorofluorophenyl, bromofluorophenyl, fluoroiodophenyl, fluoro-(trifluoromethyl)phenyl, bromochlorophenyl, chloroiodophenyl, chloro(trifluoromethyl)phenyl, bromoiodophenyl, bromo-(trifluoromethyl)phenyl, iodo(trifluoromethyl)phenyl, dichlorophenyl, difluorophenyl, dibromophenyl, trifluorophenyl, or trichlorophenyl group.

Preferably, Ar$^1$ is a phenyl group substituted with 1 to 3 substituents (said substituent is a fluorine atom, a chlorine atom or a trifluoromethyl group), for example, a 2-fluorophenyl, 2-chlorophenyl, 3-fluorophenyl, 3-chlorophenyl, 4-fluorophenyl, 4-chlorophenyl, 4-(trifluoromethyl)phenyl, 2,3-difluorophenyl, 2-fluoro-3-chlorophenyl, 2,3-dichlorophenyl, 2,4-difluorophenyl, 2-fluoro-4-chlorophenyl, 2,4-dichlorophenyl, 2-fluoro-4-(trifluoromethyl)phenyl, 2,5-difluorophenyl, 2-fluoro-5-chlorophenyl, 2,5-dichlorophenyl, 2,6-difluorophenyl, 2,3,4-trifluorophenyl, or 2,3,5-trifluorophenyl group.

More preferably, Ar$^1$ is a phenyl group substituted with 1 or 2 substituents (said substituent is a fluorine atom, a chlorine atom or a trifluoromethyl group), for example, a 2-fluorophenyl, 4-fluorophenyl, 2-chlorophenyl, 4-chlorophenyl, 4-(trifluoromethyl)phenyl, 2,4-dichlorophenyl, 2,4-difluorophenyl, or 2-fluoro-4-(trifluoromethyl)phenyl group.

Still more preferably, Ar$^1$ is a 2-fluorophenyl, 4-fluorophenyl, 4-chlorophenyl, 2,4-dichlorophenyl, or 2,4-difluorophenyl group.

Most preferably, Ar$^1$ is a 2,4-difluorophenyl group.

Ar$^2$ is, for example, a 1,2-phenylene, 1,3-phenylene, 1,4-phenylene, 1,2-naphthylene, 1,3-naphthylene, 1,4-naphthylene, 1,5-naphthylene, 1,6-naphthylene, 1,7-naphthylene, 1,8-naphthylene, 2,3-naphthylene, 2,4-naphthylene, 2,5-naphthylene, 2,6-naphthylene, 2-fluoro-1,4-phenylene, 3-chloro-1,4-phenylene, 2-chloro-1,4-phenylene, 3-chloro-1,4-phenylene, 2,6-difluoro-1,4-phenylene, or 2,6-dichloro-1,4-phenylene group.

Preferably, Ar$^2$ is 1,4-phenylene, 1,4-phenylene substituted with 1 or 2 substituents, 2,6-naphthylene, or 2,6-naphthylene substituted with 1 or 2 substituents (said substituent is a fluorine atom or a chlorine atom). A 1,4-phenylene, or 1,4-phenylene group substituted with 1 or 2 substituents (said substituent is a fluorine atom or a chlorine atom) is more preferred and a 1,4-phenylene group is most preferred.

Preferably, X is a sulfur atom or a methylene group, and more preferably X is a sulfur atom.

R$^1$ is, for example, a hydrogen atom, a methyl group or an ethyl group, preferably a $C_{1-3}$ alkyl group, and most preferably a methyl group.

R$^2$ is, for example, a hydrogen atom, a methyl group or an ethyl group, preferably a hydrogen atom or a methyl group, and most preferably a hydrogen atom.

R$^3$ is, for example, a benzyl, chlorobenzyl, fluorobenzyl, cyanobenzyl, nitrobenzyl, (trifluoromethyl)benzyl, naphthylmethyl, bromonaphthylmethyl, phenyl, tolyl, (trifluoromethyl)phenyl, hydroxymethylphenyl, hydroxyethylphenyl, cyanomethylphenyl, fluorophenyl, chlorophenyl, difluorophenyl, dichlorophenyl, pentafluorophenyl, bromophenyl, iodophenyl, hydroxyphenyl, cyanophenyl, carboxyphenyl, dicyanophenyl, chlorocyanophenyl, cyanofluorophenyl, nitrophenyl, (trifluoromethoxy)phenyl, (tetrafluoropropoxy)phenyl, acetylphenyl, (trifluoroacetyl)phenyl, carbamoylphenyl, methylthiophenyl, methylsulfinylphenyl, methylsulfonylphenyl, (trifluoromethyl)thiophenyl, (trifluoromethylsulfinyl)phenyl, (trifluoromethylsulfonyl) phenyl, carboxyphenyl, naphthyl, fluoronaphthyl, chloronaphthyl, bromonaphthyl, cyanonaphthyl, (tetrafluoropropoxy)naphthyl, imidazolyl, pyrazolyl, triazolyl, pyridyl, methoxypyridyl, oxazolyl, isoxazolyl or thiazolyl group.

Preferably, R$^3$ is a 6- to 10-membered aryl group, a 6- to 10-membered aryl group substituted with 1 to 5 substituents selected from substituent group A, a 5- or 6-membered heteroaryl group, or a 5- or 6-membered heteroaryl group substituted with 1 or 2 substituents selected from substituent group A. More preferably, R$^3$ is a 6- to 10-membered aryl group, or a 6- to 10-membered aryl group substituted with 1 to 5 substituents selected from substituent group A. Yet more preferably R$^3$ is a phenyl group substituted with 1 to 5 substituents selected from substituent group A or an unsubstituted phenyl group. Yet more and particularly preferably, R$^3$ is a phenyl group substituted with 1 to 5 substituents selected from substituent group A1 or an unsubstituted phenyl group. Yet more and more particularly preferably, R$^3$ is a phenyl group substituted with 1 to 5 substituents selected from substituent group A2 or an unsubstituted phenyl group. Still more preferably, R$^3$ is a phenyl group substituted with 1 or 2 substituents selected from substituent group A3. Most preferably, R$^3$ is a (tetrafluoropropoxy)phenyl, cyanophenyl, cyanomethylphenyl, fluorophenyl, chlorophenyl, bromophenyl, iodophenyl, (trifluoromethyl)phenyl, (trifluoromethoxy)phenyl, (trifluoromethylthio)phenyl, methylphenyl, chlorocyanophenyl, nitrophenyl, tetrafluorocyanophenyl, dicyanophenyl, acetylphenyl, acetoxyphenyl, fluorocyanophenyl, carbamoylphenyl, carboxyphenyl, hydroxyphenyl, (methanesulfonyl)phenyl, or (trifluoromethanesulfonyl)phenyl group.

The term "pharmaceutically acceptable prodrug" of compound (I) denotes a derivative of compound (I) having a protected hydroxyl group or the like which is capable of being cleaved by a chemical or biological process (e.g. by hydrolysis) on administration of the derivative to the body of a live animal to give the parent compound (I) or a salt thereof. Whether the derivative of compound (I) is such a prodrug can be easily determined. The derivative of compound (I) having a protected hydroxyl group or the like under investigation is administered orally or intravenously to a test animal such as a mouse or a rat and the body fluids of the test animal are thereafter studied. If the parent compound (I) or a salt thereof is detected in the body fluids of the test animal, the derivative under investigation is judged to be a prodrug of the compound (I). The compound (I) of this invention has a hydroxyl group and a triazole group, and an NH group when $R^2$ of the compound (I) is a hydrogen atom.

It is possible to obtain a pharmaceutically acceptable prodrug using these functional groups. Examples of such prodrugs include, for example, prodrugs of which a hydroxyl or NH group is modified by an acyl group.

As used herein, the term "acyl group" includes, for example an aliphatic acyl group, an aromatic acyl group, an alkoxycarbonyl group, an aralkyloxycarbonyl group, an aminoacyl group, phosphonyl group, or the like.

The "aliphatic acyl group" includes an alkanoyl group having 1 to 20 carbons, for example, formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, and icosanoyl. These aliphatic acyl groups may optionally have 1 to 3 multiple bonds and substituents such as a hydroxy group, a phosphoric group or a carboxyl group.

The "aromatic acyl group" includes an arylcarbonyl group having 7 to 11 carbons, for example, benzoyl, α-naphthoyl or β-naphthoyl. The aryl rings of these aromatic acyl groups may optionally have one or more substituents such as an alkyl group having 1 to 4 carbons, a halogen atom, an alkoxy group, a hydroxyl group, a carboxyl group, an alkoxycarbonyl group having 1 to 4 carbons, a hydroxyalkyl group having 1 to 4 carbons, an alkylphosphonyl group having 1 to 4 carbons, or a carboxyalkyl group having 2 to 5 carbons.

The "alkoxycarbonyl group or aralkyloxycarbonyl group" includes an alkoxycarbonyl group having 2 to 20 carbons, for example, methoxycarbonyl, ethoxycarbonyl, t-butoxycarbonyl, or isobutoxycarbonyl; and includes an aralkyloxycarbonyl group having 8 to 20 carbons, for example benzyloxycarbonyl. These alkoxycarbonyl groups or the aryl ring of these aralkyloxycarbonyl groups may optionally have one or more substituents such as an alkyl group having 1 to 4 carbons, a halogen atom, an alkoxy group having 1 to 4 carbons, a hydroxyl group, a phosphoric group, a carboxyl group, an alkoxycarbonyl group having 1 to 4 carbons, a hydroxyalkyl group having 1 to 4 carbons, an alkylphosphonyl group having 1 to 4 carbons, or a carboxyalkyl group having 2 to 5 carbons.

The "amino acyl group" includes an amino acid group, for example, glycyl, alanyl, leucyl, phenylalanyl, glutamyl and asparaginyl; an aminoalkanoyl group having 1 to 10 carbons, for example, β-alanyl, aminobutyryl or aminooctanoyl.

The "phosphonyl group" includes phosphonyl, a monoalkylphosphonyl group wherein the alkyl part has 1 to 20 carbons, for example, methylphosphonyl, ethylphosphonyl, propylphosphonyl, butylphosphonyl, decylphosphonyl, or octadecylphosphonyl; a dialkylphosphonyl group wherein each alkyl part has 1 to 20 carbons, for example, dimethylphosphonyl, diethylphosphonyl, dipropylphosphonyl, dibutylphosphonyl, didecylphosphonyl, or dioctadecylphosphonyl; or the like.

A compound (I) or a pharmaceutically acceptable prodrug thereof has a basic triazole group and may form an acid addition salt. When $R^3$ has a carboxyl group, a compound (I) or a pharmaceutically acceptable prodrug thereof may form a base addition salt. The term "pharmaceutically acceptable salt" denotes these salts which are pharmaceutically acceptable.

The acid addition salts include inorganic acid salts, for example hydrochlorides, hydrobromides, sulfates, nitrates and phosphates; carboxylic acid salts, for example acetates, fumarates, maleates, oxalates, malonates, succinates, citrates and malates; sulfonate salts, for example methanesulfonates, ethanesulfonates, benzenesulfonates and toluenesulfonates; amino acid salts, for example glutamates and aspartates; and the like. Preferred salts are inorganic acid salts or carboxylic acid salts. More preferred salts are hydrochlorides, nitrates, fumarates, maleates or oxalates.

The base addition salts include alkali metal salts, for example lithium salts, sodium salts and potassium salts; alkaline earth metal salts, for example calcium salts and magnesium salts; ammonium salts; organic base salts, for example triethylamine salts, diisopropylamine salts and cyclohexylamine salts; and the like. Preferred salts are alkali metal salts and more preferred salts are sodium salts.

When a compound (I), a pharmaceutically acceptable prodrug thereof or a salt thereof is allowed to stand so that it is open to the atomosphere it may absorb water to form a hydrate. A compound (I), or a pharmaceutically acceptable prodrug thereof or a salt thereof may also absorb a solvent to give a solvate. The present invention encompasses these hydrates and solvates.

The carbon atom attached to $Ar^1$ of the compound (I) is an asymmetric carbon, and optical isomers having this asymmetric carbon in S- and R-configuration therefore exist. When $R^1$ is an alkyl group, the carbon atom attached to $R^1$ is also an asymmetric carbon. The compound (I) can exist as diastereomers due to these asymmetric carbons. In addition, cis and trans isomers, based on the configuration of the two substituents of 1.3-dioxane ring of compound (I), also exist.

The formula (I) includes one of above described isomers as well as mixtures thereof.

The optical isomer described above can be isolated by a conventional optical resolution procedure or can be obtained by an asymmetric synthesis. A diastereomer and a cis or trans isomer can be isolated by a conventional isolation procedure such as fractional recrystallization or chromatography. Of these isolated isomers, preferred compounds (I) have the following formula (I').

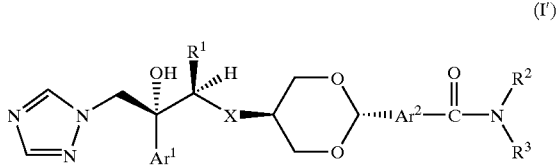

(I')

Preferred compounds of formula (I) of the present invention comprise:

(1) a compound wherein $Ar^1$ is a phenyl group substituted with 1 or 2 substituents (said substituents are selected from a fluorine atom, a chlorine atom and a trifluoromethyl group).

(2) a compound wherein $Ar^1$ is a 2-fluorophenyl, 4-fluorophenyl, 4-chlorophenyl, 2,4-dichlorophenyl or 2,4-difluorophenyl group.

(3) a compound wherein $Ar^1$ is a 2,4-difluorophenyl group.

(4) a compound wherein $Ar^2$ is a 1,4-phenylene group or a 1,4-phenylene group which is substituted with 1 or 2 substituents (said substituents are selected from a fluorine atom and a chlorine atom), a 2,6-naphthylene group, or a 2,6-naphthylene group substituted with 1 or 2 substituents (said substituents are selected from a fluorine atom and a chlorine atom).

(5) a compound wherein $Ar^2$ is a 1,4-phenylene group or a 1,4-phenylene group substituted with 1 or 2 substituents.

(6) a compound wherein $Ar^2$ is a 1,4-phenylene group.

(7) a compound wherein X is a sulfur atom.

(8) a compound wherein X is a methylene group.

(9) a compound wherein $R^1$ is a $C_{1-3}$ alkyl group.

(10) a compound wherein $R^1$ is a methyl group.

(11) a compound wherein $R^2$ is a hydrogen atom.

(12) a compound wherein $R^3$ is a $C_{6-10}$ aryl group, a $C_{6-10}$ aryl group substituted with 1 to 5 substituents selected from substituent group A, a 5- or 6-membered heteroaryl group, or a 5- or 6-membered heteroaryl group substituted with 1 or 2 substituents selected from substituent group A.

(13) a compound wherein $R^3$ is a $C_{6-10}$ aryl group or a $C_{6-10}$ aryl group substituted with 1 to 5 substituents selected from substituent group A.

(14) a compound wherein $R^3$ is a phenyl group substituted with 1 to 5 substituents selected from substituent group A or an unsubstituted phenyl group.

(15) a compound wherein $R^3$ is a heteroaryl group or a heteroaryl group substituted with 1 or 2 substituents selected from substituent group A.

(16) a compound wherein $R^3$ is a benzyl group or a benzyl group substituted with 1 or 2 substituents selected from substituent group A.

(17) a compound wherein $R^3$ is a 4-(2,2,3,3-tetrafluoropropoxy)phenyl, 4-cyanophenyl, 4-cyanomethylphenyl, 4-fluorophenyl, 4-chlorophenyl, 4-bromophenyl, 4-iodophenyl, 4-(trifluoromethyl)phenyl, 4-(trifluoromethoxy)phenyl, 4-(trifluoromethylthio)phenyl, 4-methylphenyl, 3-chloro-4-cyanophenyl, 4-nitrophenyl, 2,3,5,6-tetrafluoro-4-cyanophenyl, 3,4-dicyanophenyl, 4-acetylphenyl, 4-acetoxyphenyl, 2-fluoro-4-cyanophenyl, 4-carbamoylphenyl, 4-carboxyphenyl, 4-hydroxyphenyl, 4-(methanesulfonyl)phenyl or 4-(trifluoromethanesulfonyl)phenyl group.

(18) a compound wherein substituent group A is substituent group A1 which comprises a $C_{1-6}$ alkyl group, a $C_{1-6}$ alkyl group substituted with 1 to 4 substituents (said substituents are selected from a halogen atom, a hydroxyl group and a cyano group), a $C_{1-6}$ alkoxy group, a $C_{1-6}$ alkoxy group substituted with 1 to 5 substituents (said substituents are selected from a halogen atom, a hydroxyl group and a cyano group), a $C_{1-6}$ alkanoyl group, a $C_{2-6}$ alkanoyl group substituted with 1 to 4 substituents (said substituents are selected from a halogen atom, a hydroxyl group and a cyano group), a $C_{1-6}$ alkanoyloxy group, a $C_{2-6}$ alkanoyloxy group substituted with 1 to 4 substituents (said substituents are selected from a halogen atom, a hydroxyl group and a cyano group), a halogen atom, a hydroxyl group, a carbamoyl group, a nitro group, a cyano group, a carboxyl group and a group of formula —$S(O)_nR^4$ (wherein $R^4$ represents a $C_{1-6}$ alkyl group or a $C_{1-6}$ alkyl group substituted with 1 to 5 substituents (said substituents are selected from halogen atoms), and n represents 0, 1, or 2). (19) a compound wherein substituent group A is substituent group A2 which comprises a $C_{1-3}$ alkyl group, a $C_{1-4}$ alkyl group substituted with 1 to 4 substituents (said substituents are selected from a fluorine atom, a chlorine atom, a hydroxyl group and a cyano group), a $C_{1-3}$ alkoxy group, a $C_{1-4}$ alkoxy group substituted with 1 to 5 substituents (said substituents are selected from a fluorine atom, a chlorine atom and a hydroxyl group), a $C_{1-3}$ alkanoyl group, a $C_{2-4}$ alkanoyl group substituted with 1 to 3 substituents (said substituents are selected from a fluorine atom and a hydroxyl group), a $C_{1-3}$ alkanoyloxy group, a $C_{2-6}$ alkanoyloxy group substituted with 1 to 4 substituents (said substituents are hydroxyl groups), a halogen atom, a hydroxyl group, a carbamoyl group, a nitro group, a cyano group, a carboxyl group and a group of formula —$S(O)_nR^4$ (wherein $R^4$ represents a $C_{1-3}$ alkyl group, or a $C_{1-3}$ alkyl group substituted with 1 to 5 substituents (said substituents are fluorine atoms), and n represents 0, 1, or 2).

(20) a compound wherein substituent group A is substituent group A3 which comprises a methyl group, a trifluoromethyl group, a cyanomethyl group, a trifluoromethoxy group, a tetrafluoropropoxy group, an acetyl group, an acetoxy group, a fluorine atom, a chlorine atom, a bromine atom, an iodine atom, a hydroxyl group, a carbamoyl group, a nitro group, a cyano group, a carboxyl group, a trifluoromethylthio group, a methanesulfonyl group and a trifluoromethanesulfonyl group.

Among compounds described in (1) to (20), a compound of which each substituent is optionally selected the groups specified in (1) to (20) is also preferred. Such preferred compounds are described in the following statements (21) and (22):

(21) a compound wherein $Ar^1$ is a 2,4-difluorophenyl group; $Ar^2$ is a 1,4-phenylene group; X is a sulfur atom; $R^3$ is a $C_{1-3}$ alkyl group; $R^2$ is a hydrogen atom; $R^1$ is a phenyl group substituted with 1 or 2 substituents selected from substituent group A3.

(22) a compound wherein $Ar^1$ is a 2,4-difluorophenyl group; $Ar^2$ is a 1,4-phenylene group; X is a sulfur atom; $R^1$ is a methyl group; $R^2$ is a hydrogen atom; $R^3$ is a 4-(2,2,3,3-tetrafluoropropoxy)phenyl, 4-cyanophenyl, 4-cyanomethylphenyl, 4-fluorophenyl, 4-chlorophenyl, 4-bromophenyl, 4-iodophenyl, 4-(trifluoromethyl)phenyl, 4-(trifluoromethoxy)phenyl, 4-(trifluoromethylthio)phenyl, 4-methylphenyl, 3-chloro-4-cyanophenyl, 4-nitrophenyl, 2,3,5,6-tetrafluoro-4-cyanophenyl, 3,4-dicyanophenyl, 4-acetylphenyl, 4-acetoxyphenyl, 2-fluoro-4-cyanophenyl, 4-carbamoylphenyl, 4-carboxyphenyl, 4-hydroxyphenyl, 4-(methanesulfonyl)phenyl or 4-(trifluoromethanesulfonyl) phenyl group.

When a compound (I) has two or more substituents selected from substituent groups A to A3, these substituents may be the same or different.

Examples of compound (I) of the present invention are exemplified in table 1. The present invention is not limited to these compounds.

TABLE 1

| No. | Ar¹ | R¹ | X | Ar² | R² | R³ |
|---|---|---|---|---|---|---|
| 1-1 | 2,4-diFPh | Me | S | 1,4-Ph | H | 4-CHF$_2$CF$_2$CH$_2$O—Ph |
| 1-2 | 2,4-diFPh | Me | S | 2,6-Np | H | 4-CHF$_2$CF$_2$CH$_2$O—Ph |
| 1-3 | 2,4-diFPh | Me | CH$_2$ | 1,4-Ph | H | 4-CHF$_2$CF$_2$CH$_2$O—Ph |
| 1-4 | 2,4-diFPh | Me | CH$_2$ | 2,6-Np | H | 4-CHF$_2$CF$_2$CH$_2$O—Ph |
| 1-5 | 4-FPh | Me | S | 1,4-Ph | H | 4-CHF$_2$CF$_2$CH$_2$O—Ph |
| 1-6 | 4-FPh | Me | S | 2,6-Np | H | 4-CHF$_2$CF$_2$CH$_2$O—Ph |
| 1-7 | 4-FPh | Me | CH$_2$ | 1,4-Ph | H | 4-CHF$_2$CF$_2$CH$_2$O—Ph |
| 1-8 | 4-FPh | Me | CH$_2$ | 2,6-Np | H | 4-CHF$_2$CF$_2$CH$_2$O—Ph |
| 1-9 | 2-FPh | Me | S | 1,4-Ph | H | 4-CHF$_2$CF$_2$CH$_2$O—Ph |
| 1-10 | 2-FPh | Me | S | 2,6-Np | H | 4-CHF$_2$CF$_2$CH$_2$O—Ph |
| 1-11 | 2-FPh | Me | CH$_2$ | 1,4-Ph | H | 4-CHF$_2$CF$_2$CH$_2$O—Ph |
| 1-12 | 2-FPh | Me | CH$_2$ | 2,6-Np | H | 4-CHF$_2$CF$_2$CH$_2$O—Ph |
| 1-13 | 2,4-diClPh | Me | S | 1,4-Ph | H | 4-CHF$_2$CF$_2$CH$_2$O—Ph |
| 1-14 | 2,4-diClPh | Me | S | 2,6-Np | H | 4-CHF$_2$CF$_2$CH$_2$O—Ph |
| 1-15 | 2,4-diClPh | Me | CH$_2$ | 1,4-Ph | H | 4-CHF$_2$CF$_2$CH$_2$O—Ph |
| 1-16 | 2,4-diClPh | Me | CH$_2$ | 2,6-Np | H | 4-CHF$_2$CF$_2$CH$_2$O—Ph |
| 1-17 | 4-(CF$_3$)Ph | Me | S | 1,4-Ph | H | 4-CHF$_2$CF$_2$CH$_2$O—Ph |
| 1-18 | 4-(CF$_3$)Ph | Me | S | 2,6-Np | H | 4-CHF$_2$CF$_2$CH$_2$O—Ph |
| 1-19 | 4-(CF$_3$)Ph | Me | CH$_2$ | 1,4-Ph | H | 4-CHF$_2$CF$_2$CH$_2$O—Ph |
| 1-20 | 4-(CF$_3$)Ph | Me | CH$_2$ | 2,6-Np | H | 4-CHF$_2$CF$_2$CH$_2$O—Ph |
| 1-21 | 2,4-diFPh | Me | S | 2-F-1,4-Ph | H | 4-CHF$_2$CF$_2$CH$_2$O—Ph |
| 1-22 | 2,4-diFPh | Me | CH$_2$ | 2-F-1,4-Ph | H | 4-CHF$_2$CF$_2$CH$_2$O—Ph |
| 1-23 | 2,4-diFPh | H | S | 1,4-Ph | H | 4-CHF$_2$CF$_2$CH$_2$O—Ph |
| 1-24 | 2,4-diFPh | Et | S | 1,4-Ph | H | 4-CHF$_2$CF$_2$CH$_2$O—Ph |
| 1-25 | 2,4-diFPh | Me | S | 1,4-Ph | Me | 4-CHF$_2$CF$_2$CH$_2$O—Ph |
| 1-26 | 2,4-diFPh | Me | CH$_2$ | 1,4-Ph | Me | 4-CHF$_2$CF$_2$CH$_2$O—Ph |
| 2-1 | 2,4-diFPh | Me | S | 1,4-Ph | H | 4-CN—Ph |
| 2-2 | 2,4-diFPh | Me | S | 2,6-Np | H | 4-CN—Ph |
| 2-3 | 2,4-diFPh | Me | CH$_2$ | 1,4-Ph | H | 4-CN—Ph |
| 2-4 | 2,4-diFPh | Me | CH$_2$ | 2,6-Np | H | 4-CN—Ph |
| 2-5 | 4-FPh | Me | S | 1,4-Ph | H | 4-CN—Ph |
| 2-6 | 4-FPh | Me | S | 2,6-Np | H | 4-CN—Ph |
| 2-7 | 4-FPh | Me | CH$_2$ | 1,4-Ph | H | 4-CN—Ph |
| 2-8 | 4-FPh | Me | CH$_2$ | 2,6-Np | H | 4-CN—Ph |
| 2-9 | 2-FPh | Me | S | 1,4-Ph | H | 4-CN—Ph |
| 2-10 | 2-FPh | Me | S | 2,6-Np | H | 4-CN—Ph |
| 2-11 | 2-FPh | Me | CH$_2$ | 1,4-Ph | H | 4-CN—Ph |
| 2-12 | 2-FPh | Me | CH$_2$ | 2,6-Np | H | 4-CN—Ph |
| 2-13 | 2,4-diClPh | Me | S | 1,4-Ph | H | 4-CN—Ph |
| 2-14 | 2,4-diClPh | Me | S | 2,6-Np | H | 4-CN—Ph |
| 2-15 | 2,4-diClPh | Me | CH$_2$ | 1,4-Ph | H | 4-CN—Ph |
| 2-16 | 2,4-diClPh | Me | CH$_2$ | 2,6-Np | H | 4-CN—Ph |
| 2-17 | 4-(CF$_3$)Ph | Me | S | 1,4-Ph | H | 4-CN—Ph |
| 2-18 | 4-(CF$_3$)Ph | Me | S | 2,6-Np | H | 4-CN—Ph |
| 2-19 | 4-(CF$_3$)Ph | Me | CH$_2$ | 1,4-Ph | H | 4-CN—Ph |
| 2-20 | 4-(CF$_3$)Ph | Me | CH$_2$ | 2,6-Np | H | 4-CN—Ph |
| 2-21 | 2,4-diFPh | Me | S | 2-F-1,4-Ph | H | 4-CN—Ph |
| 2-22 | 2,4-diFPh | Me | CH$_2$ | 2-F-1,4-Ph | H | 4-CN—Ph |
| 2-23 | 2,4-diFPh | H | S | 1,4-Ph | H | 4-CN—Ph |
| 2-24 | 2,4-diFPh | Et | S | 1,4-Ph | H | 4-CN—Ph |
| 2-25 | 2,4-diFPh | Me | S | 1,3-Ph | H | 4-CN—Ph |
| 2-26 | 2,4-diFPh | Me | CH$_2$ | 1,3-Ph | H | 4-CN—Ph |
| 2-27 | 2,4-diFPh | Me | S | 1,4-Ph | Me | 4-CN—Ph |
| 2-28 | 2,4-diFPh | Me | CH$_2$ | 1,4-Ph | Me | 4-CN—Ph |
| 3-1 | 2,4-diFPh | Me | S | 1,4-Ph | H | 4-CNCH$_2$—Ph |
| 3-2 | 2,4-diFPh | Me | S | 2,6-Np | H | 4-CNCH$_2$—Ph |
| 3-3 | 2,4-diFPh | Me | CH$_2$ | 1,4-Ph | H | 4-CNCH$_2$—Ph |
| 3-4 | 2,4-diFPh | Me | CH$_2$ | 2,6-Np | H | 4-CNCH$_2$—Ph |
| 3-5 | 4-FPh | Me | S | 1,4-Ph | H | 4-CNCH$_2$—Ph |
| 3-6 | 4-FPh | Me | S | 2,6-Np | H | 4-CNCH$_2$—Ph |
| 3-7 | 4-FPh | Me | CH$_2$ | 1,4-Ph | H | 4-CNCH$_2$—Ph |
| 3-8 | 4-FPh | Me | CH$_2$ | 2,6-Np | H | 4-CNCH$_2$—Ph |
| 3-9 | 2-FPh | Me | S | 1,4-Ph | H | 4-CNCH$_2$—Ph |
| 3-10 | 2-FPh | Me | S | 2,6-Np | H | 4-CNCH$_2$—Ph |
| 3-11 | 2-FPh | Me | CH$_2$ | 1,4-Ph | H | 4-CNCH$_2$—Ph |
| 3-12 | 2-FPh | Me | CH$_2$ | 2,6-Np | H | 4-CNCH$_2$—Ph |
| 3-13 | 2,4-diClPh | Me | S | 1,4-Ph | H | 4-CNCH$_2$—Ph |
| 3-14 | 2,4-diClPh | Me | S | 2,6-Np | H | 4-CNCH$_2$—Ph |
| 3-15 | 2,4-diClPh | Me | CH$_2$ | 1,4-Ph | H | 4-CNCH$_2$—Ph |
| 3-16 | 2,4-diClPh | Me | CH$_2$ | 2,6-Np | H | 4-CNCH$_2$—Ph |
| 3-17 | 4-(CF$_3$)Ph | Me | S | 1,4-Ph | H | 4-CNCH$_2$—Ph |
| 3-18 | 4-(CF$_3$)Ph | Me | S | 2,6-Np | H | 4-CNCH$_2$—Ph |
| 3-19 | 4-(CF$_3$)Ph | Me | CH$_2$ | 1,4-Ph | H | 4-CNCH$_2$—Ph |
| 3-20 | 4-(CF$_3$)Ph | Me | CH$_2$ | 2,6-Np | H | 4-CNCH$_2$—Ph |
| 3-21 | 2,4-diFPh | Me | S | 2-F-1,4-Ph | H | 4-CNCH$_2$—Ph |
| 3-22 | 2,4-diFPh | Me | CH$_2$ | 2-F-1,4-Ph | H | 4-CNCH$_2$—Ph |
| 3-23 | 2,4-diFPh | H | S | 1,4-Ph | H | 4-CNCH$_2$—Ph |

TABLE 1-continued

| No. | Ar¹ | R¹ | X | Ar² | R² | R³ |
|---|---|---|---|---|---|---|
| 3-24 | 2,4-diFPh | Et | S | 1,4-Ph | H | 4-CNCH$_2$—Ph |
| 3-25 | 2,4-diFPh | Me | S | 1,4-Ph | Me | 4-CNCH$_2$—Ph |
| 3-26 | 2,4-diFPh | Me | CH$_2$ | 1,4-Ph | Me | 4-CNCH$_2$—Ph |
| 4-1 | 2,4-diFPh | Me | S | 1,4-Ph | H | 4-Cl—Ph |
| 4-2 | 2,4-diFPh | Me | S | 2,6-Np | H | 4-Cl—Ph |
| 4-3 | 2,4-diFPh | Me | CH$_2$ | 1,4-Ph | H | 4-Cl—Ph |
| 4-4 | 2,4-diFPh | Me | CH$_2$ | 2,6-Np | H | 4-Cl—Ph |
| 4-5 | 4-FPh | Me | S | 1,4-Ph | H | 4-Cl—Ph |
| 4-6 | 4-FPh | Me | S | 2,6-Np | H | 4-Cl—Ph |
| 4-7 | 4-FPh | Me | CH$_2$ | 1,4-Ph | H | 4-Cl—Ph |
| 4-8 | 4-FPh | Me | CH$_2$ | 2,6-Np | H | 4-Cl—Ph |
| 4-9 | 2-FPh | Me | S | 1,4-Ph | H | 4-Cl—Ph |
| 4-10 | 2-FPh | Me | S | 2,6-Np | H | 4-Cl—Ph |
| 4-11 | 2-FPh | Me | CH$_2$ | 1,4-Ph | H | 4-Cl—Ph |
| 4-12 | 2-FPh | Me | CH$_2$ | 2,6-Np | H | 4-Cl—Ph |
| 4-13 | 2,4-diClPh | Me | S | 1,4-Ph | H | 4-Cl—Ph |
| 4-14 | 2,4-diClPh | Me | S | 2,6-Np | H | 4-Cl—Ph |
| 4-15 | 2,4-diClPh | Me | CH$_2$ | 1,4-Ph | H | 4-Cl—Ph |
| 4-16 | 2,4-diClPh | Me | CH$_2$ | 2,6-Np | H | 4-Cl—Ph |
| 4-17 | 4-(CF$_3$)Ph | Me | S | 1,4-Ph | H | 4-Cl—Ph |
| 4-18 | 4-(CF$_3$)Ph | Me | S | 2,6-Np | H | 4-Cl—Ph |
| 4-19 | 4-(CF$_3$)Ph | Me | CH$_2$ | 1,4-Ph | H | 4-Cl—Ph |
| 4-20 | 4-(CF$_3$)Ph | Me | CH$_2$ | 2,6-Np | H | 4-Cl—Ph |
| 4-21 | 2,4-diFPh | Me | S | 2-F-1,4-Ph | H | 4-Cl—Ph |
| 4-22 | 2,4-diFPh | Me | CH$_2$ | 2-F-1,4-Ph | H | 4-Cl—Ph |
| 4-23 | 2,4-diFPh | H | S | 1,4-Ph | H | 4-Cl—Ph |
| 4-24 | 2,4-diFPh | Et | S | 1,4-Ph | H | 4-Cl—Ph |
| 4-25 | 2,4-diFPh | Me | S | 1,3-Ph | H | 4-Cl—Ph |
| 4-26 | 2,4-diFPh | Me | CH$_2$ | 1,3-Ph | H | 4-Cl—Ph |
| 4-27 | 2,4-diFPh | Me | S | 1,4-Ph | Me | 4-Cl—Ph |
| 4-28 | 2,4-diFPh | Me | CH$_2$ | 1,4-Ph | Me | 4-Cl—Ph |
| 5-1 | 2,4-diFPh | Me | S | 1,4-Ph | H | 4-F—Ph |
| 5-2 | 2,4-diFPh | Me | S | 2,6-Np | H | 4-F—Ph |
| 5-3 | 2,4-diFPh | Me | CH$_2$ | 1,4-Ph | H | 4-F—Ph |
| 5-4 | 2,4-diFPh | Me | CH$_2$ | 2,6-Np | H | 4-F—Ph |
| 5-5 | 4-FPh | Me | S | 1,4-Ph | H | 4-F—Ph |
| 5-6 | 4-FPh | Me | S | 2,6-Np | H | 4-F—Ph |
| 5-7 | 4-FPh | Me | CH$_2$ | 1,4-Ph | H | 4-F—Ph |
| 5-8 | 4-FPh | Me | CH$_2$ | 2,6-Np | H | 4-F—Ph |
| 5-9 | 2-FPh | Me | S | 1,4-Ph | H | 4-F—Ph |
| 5-10 | 2-FPh | Me | S | 2,6-Np | H | 4-F—Ph |
| 5-11 | 2-FPh | Me | CH$_2$ | 1,4-Ph | H | 4-F—Ph |
| 5-12 | 2-FPh | Me | CH$_2$ | 2,6-Np | H | 4-F—Ph |
| 5-13 | 2,4-diClPh | Me | S | 1,4-Ph | H | 4-F—Ph |
| 5-14 | 2,4-diClPh | Me | S | 2,6-Np | H | 4-F—Ph |
| 5-15 | 2,4-diClPh | Me | CH$_2$ | 1,4-Ph | H | 4-F—Ph |
| 5-16 | 2,4-diClPh | Me | CH$_2$ | 2,6-Np | H | 4-F—Ph |
| 5-17 | 4-(CF$_3$)Ph | Me | S | 1,4-Ph | H | 4-F—Ph |
| 5-18 | 4-(CF$_3$)Ph | Me | S | 2,6-Np | H | 4-F—Ph |
| 5-19 | 4-(CF$_3$)Ph | Me | CH$_2$ | 1,4-Ph | H | 4-F—Ph |
| 5-20 | 4-(CF$_3$)Ph | Me | CH$_2$ | 2,6-Np | H | 4-F—Ph |
| 5-21 | 2,4-diFPh | Me | S | 2-F-1,4-Ph | H | 4-F—Ph |
| 5-22 | 2,4-diFPh | Me | CH$_2$ | 2-F-1,4-Ph | H | 4-F—Ph |
| 5-23 | 2,4-diFPh | H | S | 1,4-Ph | H | 4-F—Ph |
| 5-24 | 2,4-diFPh | Et | S | 1,4-Ph | H | 4-F—Ph |
| 5-25 | 2,4-diFPh | Me | S | 1,4-Ph | Me | 4-F—Ph |
| 5-26 | 2,4-diFPh | Me | CH$_2$ | 1,4-Ph | Me | 4-F—Ph |
| 6-1 | 2,4-diFPh | Me | S | 1,4-Ph | H | 4-CF$_3$—Ph |
| 6-2 | 2,4-diFPh | Me | S | 2,6-Np | H | 4-CF$_3$—Ph |
| 6-3 | 2,4-diFPh | Me | CH$_2$ | 1,4-Ph | H | 4-CF$_3$—Ph |
| 6-4 | 2,4-diFPh | Me | CH$_2$ | 2,6-Np | H | 4-CF$_3$—Ph |
| 6-5 | 4-FPh | Me | S | 1,4-Ph | H | 4-CF$_3$—Ph |
| 6-6 | 4-FPh | Me | S | 2,6-Np | H | 4-CF$_3$—Ph |
| 6-7 | 4-FPh | Me | CH$_2$ | 1,4-Ph | H | 4-CF$_3$—Ph |
| 6-8 | 4-FPh | Me | CH$_2$ | 2,6-Np | H | 4-CF$_3$—Ph |
| 6-9 | 2-FPh | Me | S | 1,4-Ph | H | 4-CF$_3$—Ph |
| 6-10 | 2-FPh | Me | S | 2,6-Np | H | 4-CF$_3$—Ph |
| 6-11 | 2-FPh | Me | CH$_2$ | 1,4-Ph | H | 4-CF$_3$—Ph |
| 6-12 | 2-FPh | Me | CH$_2$ | 2,6-Np | H | 4-CF$_3$—Ph |
| 6-13 | 2,4-diClPh | Me | S | 1,4-Ph | H | 4-CF$_3$—Ph |
| 6-14 | 2,4-diClPh | Me | S | 2,6-Np | H | 4-CF$_3$—Ph |
| 6-15 | 2,4-diClPh | Me | CH$_2$ | 1,4-Ph | H | 4-CF$_3$—Ph |
| 6-16 | 2,4-diClPh | Me | CH$_2$ | 2,6-Np | H | 4-CF$_3$—Ph |
| 6-17 | 4-(CF$_3$)Ph | Me | S | 1,4-Ph | H | 4-CF$_3$—Ph |
| 6-18 | 4-(CF$_3$)Ph | Me | S | 2,6-Np | H | 4-CF$_3$—Ph |
| 6-19 | 4-(CF$_3$)Ph | Me | CH$_2$ | 1,4-Ph | H | 4-CF$_3$—Ph |
| 6-20 | 4-(CF$_3$)Ph | Me | CH$_2$ | 2,6-Np | H | 4-CF$_3$—Ph |

TABLE 1-continued

| No. | Ar¹ | R¹ | X | Ar² | R² | R³ |
|---|---|---|---|---|---|---|
| 6-21 | 2,4-diFPh | Me | S | 2-F-1,4-Ph | H | 4-CF$_3$—Ph |
| 6-22 | 2,4-diFPh | Me | CH$_2$ | 2-F-1,4-Ph | H | 4-CF$_3$—Ph |
| 6-23 | 2,4-diFPh | H | S | 1,4-Ph | H | 4-CF$_3$—Ph |
| 6-24 | 2,4-diFPh | Et | S | 1,4-Ph | H | 4-CF$_3$—Ph |
| 6-25 | 2,4-diFPh | Me | S | 1,4-Ph | Me | 4-CF$_3$—Ph |
| 6-26 | 2,4-diFPh | Me | CH$_2$ | 1,4-Ph | Me | 4-CF$_3$—Ph |
| 7-1 | 2,4-diFPh | Me | S | 1,4-Ph | H | 4-CF$_3$O—Ph |
| 7-2 | 2,4-diFPh | Me | S | 2,6-Np | H | 4-CF$_3$O—Ph |
| 7-3 | 2,4-diFPh | Me | CH$_2$ | 1,4-Ph | H | 4-CF$_3$O—Ph |
| 7-4 | 2,4-diFPh | Me | CH$_2$ | 2,6-Np | H | 4-CF$_3$O—Ph |
| 7-5 | 4-FPh | Me | S | 1,4-Ph | H | 4-CF$_3$O—Ph |
| 7-6 | 4-FPh | Me | S | 2,6-Np | H | 4-CF$_3$O—Ph |
| 7-7 | 4-FPh | Me | CH$_2$ | 1,4-Ph | H | 4-CF$_3$O—Ph |
| 7-8 | 4-FPh | Me | CH$_2$ | 2,6-Np | H | 4-CF$_3$O—Ph |
| 7-9 | 2-FPh | Me | S | 1,4-Ph | H | 4-CF$_3$O—Ph |
| 7-10 | 2-FPh | Me | S | 2,6-Np | H | 4-CF$_3$O—Ph |
| 7-11 | 2-FPh | Me | CH$_2$ | 1,4-Ph | H | 4-CF$_3$O—Ph |
| 7-12 | 2-FPh | Me | CH$_2$ | 2,6-Np | H | 4-CF$_3$O—Ph |
| 7-13 | 2,4-diClPh | Me | S | 1,4-Ph | H | 4-CF$_3$O—Ph |
| 7-14 | 2,4-diClPh | Me | S | 2,6-Np | H | 4-CF$_3$O—Ph |
| 7-15 | 2,4-diClPh | Me | CH$_2$ | 1,4-Ph | H | 4-CF$_3$O—Ph |
| 7-16 | 2,4-diClPh | Me | CH$_2$ | 2,6-Np | H | 4-CF$_3$O—Ph |
| 7-17 | 4-(CF$_3$)Ph | Me | S | 1,4-Ph | H | 4-CF$_3$O—Ph |
| 7-18 | 4-(CF$_3$)Ph | Me | S | 2,6-Np | H | 4-CF$_3$O—Ph |
| 7-19 | 4-(CF$_3$)Ph | Me | CH$_2$ | 1,4-Ph | H | 4-CF$_3$O—Ph |
| 7-20 | 4-(CF$_3$)Ph | Me | CH$_2$ | 2,6-Np | H | 4-CF$_3$O—Ph |
| 7-21 | 2,4-diFPh | Me | S | 2-F-1,4-Ph | H | 4-CF$_3$O—Ph |
| 7-22 | 2,4-diFPh | Me | CH$_2$ | 2-F-1,4-Ph | H | 4-CF$_3$O—Ph |
| 7-23 | 2,4-diFPh | H | S | 1,4-Ph | H | 4-CF$_3$O—Ph |
| 7-24 | 2,4-diFPh | Et | S | 1,4-Ph | H | 4-CF$_3$O—Ph |
| 7-25 | 2,4-diFPh | Me | S | 1,4-Ph | Me | 4-CF$_3$O—Ph |
| 7-26 | 2,4-diFPh | Me | CH$_2$ | 1,4-Ph | Me | 4-CF$_3$O—Ph |
| 8-1 | 2,4-diFPh | Me | S | 1,4-Ph | H | 4-CF$_3$S—Ph |
| 8-2 | 2,4-diFPh | Me | S | 2,6-Np | H | 4-CF$_3$S—Ph |
| 8-3 | 2,4-diFPh | Me | CH$_2$ | 1,4-Ph | H | 4-CF$_3$S—Ph |
| 8-4 | 2,4-diFPh | Me | CH$_2$ | 2,6-Np | H | 4-CF$_3$S—Ph |
| 8-5 | 4-FPh | Me | S | 1,4-Ph | H | 4-CF$_3$S—Ph |
| 8-6 | 4-FPh | Me | S | 2,6-Np | H | 4-CF$_3$S—Ph |
| 8-7 | 4-FPh | Me | CH$_2$ | 1,4-Ph | H | 4-CF$_3$S—Ph |
| 8-8 | 4-FPh | Me | CH$_2$ | 2,6-Np | H | 4-CF$_3$S—Ph |
| 8-9 | 2-FPh | Me | S | 1,4-Ph | H | 4-CF$_3$S—Ph |
| 8-10 | 2-FPh | Me | S | 2,6-Np | H | 4-CF$_3$S—Ph |
| 8-11 | 2-FPh | Me | CH$_2$ | 1,4-Ph | H | 4-CF$_3$S—Ph |
| 8-12 | 2-FPh | Me | CH$_2$ | 2,6-Np | H | 4-CF$_3$S—Ph |
| 8-13 | 2,4-diClPh | Me | S | 1,4-Ph | H | 4-CF$_3$S—Ph |
| 8-14 | 2,4-diClPh | Me | S | 2,6-Np | H | 4-CF$_3$S—Ph |
| 8-15 | 2,4-diClPh | Me | CH$_2$ | 1,4-Ph | H | 4-CF$_3$S—Ph |
| 8-16 | 2,4-diClPh | Me | CH$_2$ | 2,6-Np | H | 4-CF$_3$S—Ph |
| 8-17 | 4-(CF$_3$)Ph | Me | S | 1,4-Ph | H | 4-CF$_3$S—Ph |
| 8-18 | 4-(CF$_3$)Ph | Me | S | 2,6-Np | H | 4-CF$_3$S—Ph |
| 8-19 | 4-(CF$_3$)Ph | Me | CH$_2$ | 1,4-Ph | H | 4-CF$_3$S—Ph |
| 8-20 | 4-(CF$_3$)Ph | Me | CH$_2$ | 2,6-Np | H | 4-CF$_3$S—Ph |
| 8-21 | 2,4-diFPh | Me | S | 2-F-1,4-Ph | H | 4-CF$_3$S—Ph |
| 8-22 | 2,4-diFPh | Me | CH$_2$ | 2-F-1,4-Ph | H | 4-CF$_3$S—Ph |
| 8-23 | 2,4-diFPh | H | S | 1,4-Ph | H | 4-CF$_3$S—Ph |
| 8-24 | 2,4-diFPh | Et | S | 1,4-Ph | H | 4-CF$_3$S—Ph |
| 8-25 | 2,4-diFPh | Me | S | 1,4-Ph | Me | 4-CF$_3$S—Ph |
| 8-26 | 2,4-diFPh | Me | CH$_2$ | 1,4-Ph | Me | 4-CF$_3$S—Ph |
| 9-1 | 2,4-diFPh | Me | S | 1,4-Ph | H | 4-CH$_3$—Ph |
| 9-2 | 2,4-diFPh | Me | S | 2,6-Np | H | 4-CH$_3$—Ph |
| 9-3 | 2,4-diFPh | Me | CH$_2$ | 1,4-Ph | H | 4-CH$_3$—Ph |
| 9-4 | 2,4-diFPh | Me | CH$_2$ | 2,6-Np | H | 4-CH$_3$—Ph |
| 9-5 | 4-FPh | Me | S | 1,4-Ph | H | 4-CH$_3$—Ph |
| 9-6 | 4-FPh | Me | S | 2,6-Np | H | 4-CH$_3$—Ph |
| 9-7 | 4-FPh | Me | CH$_2$ | 1,4-Ph | H | 4-CH$_3$—Ph |
| 9-8 | 4-FPh | Me | CH$_2$ | 2,6-Np | H | 4-CH$_3$—Ph |
| 9-9 | 2-FPh | Me | S | 1,4-Ph | H | 4-CH$_3$—Ph |
| 9-10 | 2-FPh | Me | S | 2,6-Np | H | 4-CH$_3$—Ph |
| 9-11 | 2-FPh | Me | CH$_2$ | 1,4-Ph | H | 4-CH$_3$—Ph |
| 9-12 | 2-FPh | Me | CH$_2$ | 2,6-Np | H | 4-CH$_3$—Ph |
| 9-13 | 2,4-diClPh | Me | S | 1,4-Ph | H | 4-CH$_3$—Ph |
| 9-14 | 2,4-diClPh | Me | S | 2,6-Np | H | 4-CH$_3$—Ph |
| 9-15 | 2,4-diClPh | Me | CH$_2$ | 1,4-Ph | H | 4-CH$_3$—Ph |
| 9-16 | 2,4-diClPh | Me | CH$_2$ | 2,6-Np | H | 4-CH$_3$—Ph |
| 9-17 | 4-(CF$_3$)Ph | Me | S | 1,4-Ph | H | 4-CH$_3$—Ph |
| 9-18 | 4-(CF$_3$)Ph | Me | S | 2,6-Np | H | 4-CH$_3$—Ph |
| 9-19 | 4-(CF$_3$)Ph | Me | CH$_2$ | 1,4-Ph | H | 4-CH$_3$—Ph |

TABLE 1-continued

| No. | Ar¹ | R¹ | X | Ar² | R² | R³ |
|---|---|---|---|---|---|---|
| 9-20 | 4-(CF₃)Ph | Me | CH₂ | 2,6-Np | H | 4-CH₃—Ph |
| 9-21 | 2,4-diFPh | Me | S | 2-F-1,4-Ph | H | 4-CH₃—Ph |
| 9-22 | 2,4-diFPh | Me | CH₂ | 2-F-1,4-Ph | H | 4-CH₃—Ph |
| 9-23 | 2,4-diFPh | H | S | 1,4-Ph | H | 4-CH₃—Ph |
| 9-24 | 2,4-diFPh | Et | S | 1,4-Ph | H | 4-CH₃—Ph |
| 9-25 | 2,4-diFPh | Me | S | 1,4-Ph | Me | 4-CH₃—Ph |
| 9-26 | 2,4-diFPh | Me | CH₂ | 1,4-Ph | Me | 4-CH₃—Ph |
| 10-1 | 2,4-diFPh | Me | S | 1,4-Ph | H | 4-Br—Ph |
| 10-2 | 2,4-diFPh | Me | S | 2,6-Np | H | 4-Br—Ph |
| 10-3 | 2,4-diFPh | Me | CH₂ | 1,4-Ph | H | 4-Br—Ph |
| 10-4 | 2,4-diFPh | Me | CH₂ | 2,6-Np | H | 4-Br—Ph |
| 10-5 | 4-FPh | Me | S | 1,4-Ph | H | 4-Br—Ph |
| 10-6 | 4-FPh | Me | S | 2,6-Np | H | 4-Br—Ph |
| 10-7 | 4-FPh | Me | CH₂ | 1,4-Ph | H | 4-Br—Ph |
| 10-8 | 4-FPh | Me | CH₂ | 2,6-Np | H | 4-Br—Ph |
| 10-9 | 2-FPh | Me | S | 1,4-Ph | H | 4-Br—Ph |
| 10-10 | 2-FPh | Me | S | 2,6-Np | H | 4-Br—Ph |
| 10-11 | 2-FPh | Me | CH₂ | 1,4-Ph | H | 4-Br—Ph |
| 10-12 | 2-FPh | Me | CH₂ | 2,6-Np | H | 4-Br—Ph |
| 10-13 | 2,4-diClPh | Me | S | 1,4-Ph | H | 4-Br—Ph |
| 10-14 | 2,4-diClPh | Me | S | 2,6-Np | H | 4-Br—Ph |
| 10-15 | 2,4-diClPh | Me | CH₂ | 1,4-Ph | H | 4-Br—Ph |
| 10-16 | 2,4-diClPh | Me | CH₂ | 2,6-Np | H | 4-Br—Ph |
| 10-17 | 4-(CF₃)Ph | Me | S | 1,4-Ph | H | 4-Br—Ph |
| 10-18 | 4-(CF₃)Ph | Me | S | 2,6-Np | H | 4-Br—Ph |
| 10-19 | 4-(CF₃)Ph | Me | CH₂ | 1,4-Ph | H | 4-Br—Ph |
| 10-20 | 4-(CF₃)Ph | Me | CH₂ | 2,6-Np | H | 4-Br—Ph |
| 10-21 | 2,4-diFPh | Me | S | 2-F-1,4-Ph | H | 4-Br—Ph |
| 10-22 | 2,4-diFPh | Me | CH₂ | 2-F-1,4-Ph | H | 4-Br—Ph |
| 10-23 | 2,4-diFPh | H | S | 1,4-Ph | H | 4-Br—Ph |
| 10-24 | 2,4-diFPh | Et | S | 1,4-Ph | H | 4-Br—Ph |
| 10-25 | 2,4-diFPh | Me | S | 1,4-Ph | Me | 4-Br—Ph |
| 10-26 | 2,4-diFPh | Me | CH₂ | 1,4-Ph | Me | 4-Br—Ph |
| 11-1 | 2,4-diFPh | Me | S | 1,4-Ph | H | 3-Cl-4-CN—Ph |
| 11-2 | 2,4-diFPh | Me | S | 2,6-Np | H | 3-Cl-4-CN—Ph |
| 11-3 | 2,4-diFPh | Me | CH₂ | 1,4-Ph | H | 3-Cl-4-CN—Ph |
| 11-4 | 2,4-diFPh | Me | CH₂ | 2,6-Np | H | 3-Cl-4-CN—Ph |
| 11-5 | 4-FPh | Me | S | 1,4-Ph | H | 3-Cl-4-CN—Ph |
| 11-6 | 4-FPh | Me | S | 2,6-Np | H | 3-Cl-4-CN—Ph |
| 11-7 | 4-FPh | Me | CH₂ | 1,4-Ph | H | 3-Cl-4-CN—Ph |
| 11-8 | 4-FPh | Me | CH₂ | 2,6-Np | H | 3-Cl-4-CN—Ph |
| 11-9 | 2-FPh | Me | S | 1,4-Ph | H | 3-Cl-4-CN—Ph |
| 11-10 | 2-FPh | Me | S | 2,6-Np | H | 3-Cl-4-CN—Ph |
| 11-11 | 2-FPh | Me | CH₂ | 1,4-Ph | H | 3-Cl-4-CN—Ph |
| 11-12 | 2-FPh | Me | CH₂ | 2,6-Np | H | 3-Cl-4-CN—Ph |
| 11-13 | 2,4-diClPh | Me | S | 1,4-Ph | H | 3-Cl-4-CN—Ph |
| 11-14 | 2,4-diClPh | Me | S | 2,6-Np | H | 3-Cl-4-CN—Ph |
| 11-15 | 2,4-diClPh | Me | CH₂ | 1,4-Ph | H | 3-Cl-4-CN—Ph |
| 11-16 | 2,4-diClPh | Me | CH₂ | 2,6-Np | H | 3-Cl-4-CN—Ph |
| 11-17 | 4-(CF₃)Ph | Me | S | 1,4-Ph | H | 3-Cl-4-CN—Ph |
| 11-18 | 4-(CF₃)Ph | Me | S | 2,6-Np | H | 3-Cl-4-CN—Ph |
| 11-19 | 4-(CF₃)Ph | Me | CH₂ | 1,4-Ph | H | 3-Cl-4-CN—Ph |
| 11-20 | 4-(CF₃)Ph | Me | CH₂ | 2,6-Np | H | 3-Cl-4-CN—Ph |
| 11-21 | 2,4-diFPh | Me | S | 2-F-1,4-Ph | H | 3-Cl-4-CN—Ph |
| 11-22 | 2,4-diFPh | Me | CH₂ | 2-F-1,4-Ph | H | 3-Cl-4-CN—Ph |
| 11-23 | 2,4-diFPh | H | S | 1,4-Ph | H | 3-Cl-4-CN—Ph |
| 11-24 | 2,4-diFPh | Et | S | 1,4-Ph | H | 3-Cl-4-CN—Ph |
| 11-25 | 2,4-diFPh | Me | S | 1,4-Ph | Me | 3-Cl-4-CN—Ph |
| 11-26 | 2,4-diFPh | Me | CH₂ | 1,4-Ph | Me | 3-Cl-4-CN—Ph |
| 12-1 | 2,4-diFPh | Me | S | 1,4-Ph | H | 4-Pyr |
| 12-2 | 2,4-diFPh | Me | S | 2,6-Np | H | 4-Pyr |
| 12-3 | 2,4-diFPh | Me | CH₂ | 1,4-Ph | H | 4-Pyr |
| 12-4 | 2,4-diFPh | Me | CH₂ | 2,6-Np | H | 4-Pyr |
| 12-5 | 4-FPh | Me | S | 1,4-Ph | H | 4-Pyr |
| 12-6 | 4-FPh | Me | S | 2,6-Np | H | 4-Pyr |
| 12-7 | 4-FPh | Me | CH₂ | 1,4-Ph | H | 4-Pyr |
| 12-8 | 4-FPh | Me | CH₂ | 2,6-Np | H | 4-Pyr |
| 12-9 | 2-FPh | Me | S | 1,4-Ph | H | 4-Pyr |
| 12-10 | 2-FPh | Me | S | 2,6-Np | H | 4-Pyr |
| 12-11 | 2-FPh | Me | CH₂ | 1,4-Ph | H | 4-Pyr |
| 12-12 | 2-FPh | Me | CH₂ | 2,6-Np | H | 4-Pyr |
| 12-13 | 2,4-diClPh | Me | S | 1,4-Ph | H | 4-Pyr |
| 12-14 | 2,4-diClPh | Me | S | 2,6-Np | H | 4-Pyr |
| 12-15 | 2,4-diClPh | Me | CH₂ | 1,4-Ph | H | 4-Pyr |
| 12-16 | 2,4-diClPh | Me | CH₂ | 2,6-Np | H | 4-Pyr |
| 12-17 | 4-(CF₃)Ph | Me | S | 1,4-Ph | H | 4-Pyr |
| 12-18 | 4-(CF₃)Ph | Me | S | 2,6-Np | H | 4-Pyr |

TABLE 1-continued

| No. | Ar¹ | R¹ | X | Ar² | R² | R³ |
|---|---|---|---|---|---|---|
| 12-19 | 4-(CF$_3$)Ph | Me | CH$_2$ | 1,4-Ph | H | 4-Pyr |
| 12-20 | 4-(CF$_3$)Ph | Me | CH$_2$ | 2,6-Np | H | 4-Pyr |
| 12-21 | 2,4-diFPh | Me | S | 2-F-1,4-Ph | H | 4-Pyr |
| 12-22 | 2,4-diFPh | Me | CH$_2$ | 2-F-1,4-Ph | H | 4-Pyr |
| 12-23 | 2,4-diFPh | H | S | 1,4-Ph | H | 4-Pyr |
| 12-24 | 2,4-diFPh | Et | S | 1,4-Ph | H | 4-Pyr |
| 12-25 | 2,4-diFPh | Me | S | 1,4-Ph | Me | 4-Pyr |
| 12-26 | 2,4-diFPh | Me | CH$_2$ | 1,4-Ph | Me | 4-Pyr |
| 13-1 | 2,4-diFPh | Me | S | 1,4-Ph | H | 4-NO$_2$—Ph |
| 13-2 | 2,4-diFPh | Me | S | 2,6-Np | H | 4-NO$_2$—Ph |
| 13-3 | 2,4-diFPh | Me | CH$_2$ | 1,4-Ph | H | 4-NO$_2$—Ph |
| 13-4 | 2,4-diFPh | Me | CH$_2$ | 2,6-Np | H | 4-NO$_2$—Ph |
| 13-5 | 4-FPh | Me | S | 1,4-Ph | H | 4-NO$_2$—Ph |
| 13-6 | 4-FPh | Me | S | 2,6-Np | H | 4-NO$_2$—Ph |
| 13-7 | 4-FPh | Me | CH$_2$ | 1,4-Ph | H | 4-NO$_2$—Ph |
| 13-8 | 4-FPh | Me | CH$_2$ | 2,6-Np | H | 4-NO$_2$—Ph |
| 13-9 | 2-FPh | Me | S | 1,4-Ph | H | 4-NO$_2$—Ph |
| 13-10 | 2-FPh | Me | S | 2,6-Np | H | 4-NO$_2$—Ph |
| 13-11 | 2-FPh | Me | CH$_2$ | 1,4-Ph | H | 4-NO$_2$—Ph |
| 13-12 | 2-FPh | Me | CH$_2$ | 2,6-Np | H | 4-NO$_2$—Ph |
| 13-13 | 2,4-diClPh | Me | S | 1,4-Ph | H | 4-NO$_2$—Ph |
| 13-14 | 2,4-diClPh | Me | S | 2,6-Np | H | 4-NO$_2$—Ph |
| 13-15 | 2,4-diClPh | Me | CH$_2$ | 1,4-Ph | H | 4-NO$_2$—Ph |
| 13-16 | 2,4-diClPh | Me | CH$_2$ | 2,6-Np | H | 4-NO$_2$—Ph |
| 13-17 | 4-(CF$_3$)Ph | Me | S | 1,4-Ph | H | 4-NO$_2$—Ph |
| 13-18 | 4-(CF$_3$)Ph | Me | S | 2,6-Np | H | 4-NO$_2$—Ph |
| 13-19 | 4-(CF$_3$)Ph | Me | CH$_2$ | 1,4-Ph | H | 4-NO$_2$—Ph |
| 13-20 | 4-(CF$_3$)Ph | Me | CH$_2$ | 2,6-Np | H | 4-NO$_2$—Ph |
| 13-21 | 2,4-diFPh | Me | S | 2-F-1,4-Ph | H | 4-NO$_2$—Ph |
| 13-22 | 2,4-diFPh | Me | CH$_2$ | 2-F-1,4-Ph | H | 4-NO$_2$—Ph |
| 13-23 | 2,4-diFPh | H | S | 1,4-Ph | H | 4-NO$_2$—Ph |
| 13-24 | 2,4-diFPh | Et | S | 1,4-Ph | H | 4-NO$_2$—Ph |
| 13-25 | 2,4-diFPh | Me | S | 1,4-Ph | Me | 4-NO$_2$—Ph |
| 13-26 | 2,4-diFPh | Me | CH$_2$ | 1,4-Ph | Me | 4-NO$_2$—Ph |
| 14-1 | 2,4-diFPh | Me | S | 1,4-Ph | H | 2,3,5,6-TetF-4-CN—Ph |
| 14-2 | 2,4-diFPh | Me | S | 2,6-Np | H | 2,3,5,6-TetF-4-CN—Ph |
| 14-3 | 2,4-diFPh | Me | CH$_2$ | 1,4-Ph | H | 2,3,5,6-TetF-4-CN—Ph |
| 14-4 | 2,4-diFPh | Me | CH$_2$ | 2,6-Np | H | 2,3,5,6-TetF-4-CN—Ph |
| 14-5 | 4-FPh | Me | S | 1,4-Ph | H | 2,3,5,6-TetF-4-CN—Ph |
| 14-6 | 4-FPh | Me | S | 2,6-Np | H | 2,3,5,6-TetF-4-CN—Ph |
| 14-7 | 4-FPh | Me | CH$_2$ | 1,4-Ph | H | 2,3,5,6-TetF-4-CN—Ph |
| 14-8 | 4-FPh | Me | CH$_2$ | 2,6-Np | H | 2,3,5,6-TetF-4-CN—Ph |
| 14-9 | 2-FPh | Me | S | 1,4-Ph | H | 2,3,5,6-TetF-4-CN—Ph |
| 14-10 | 2-FPh | Me | S | 2,6-Np | H | 2,3,5,6-TetF-4-CN—Ph |
| 14-11 | 2-FPh | Me | CH$_2$ | 1,4-Ph | H | 2,3,5,6-TetF-4-CN—Ph |
| 14-12 | 2-FPh | Me | CH$_2$ | 2,6-Np | H | 2,3,5,6-TetF-4-CN—Ph |
| 14-13 | 2,4-diClPh | Me | S | 1,4-Ph | H | 2,3,5,6-TetF-4-CN—Ph |
| 14-14 | 2,4-diClPh | Me | S | 2,6-Np | H | 2,3,5,6-TetF-4-CN—Ph |
| 14-15 | 2,4-diClPh | Me | CH$_2$ | 1,4-Ph | H | 2,3,5,6-TetF-4-CN—Ph |
| 14-16 | 2,4-diClPh | Me | CH$_2$ | 2,6-Np | H | 2,3,5,6-TetF-4-CN—Ph |
| 14-17 | 4-(CF$_3$)Ph | Me | S | 1,4-Ph | H | 2,3,5,6-TetF-4-CN—Ph |
| 14-18 | 4-(CF$_3$)Ph | Me | S | 2,6-Np | H | 2,3,5,6-TetF-4-CN—Ph |
| 14-19 | 4-(CF$_3$)Ph | Me | CH$_2$ | 1,4-Ph | H | 2,3,5,6-TetF-4-CN—Ph |
| 14-20 | 4-(CF$_3$)Ph | Me | CH$_2$ | 2,6-Np | H | 2,3,5,6-TetF-4-CN—Ph |
| 14-21 | 2,4-diFPh | Me | S | 2-F-1,4-Ph | H | 2,3,5,6-TetF-4-CN—Ph |
| 14-22 | 2,4-diFPh | Me | CH$_2$ | 2-F-1,4-Ph | H | 2,3,5,6-TetF-4-CN—Ph |
| 14-23 | 2,4-diFPh | H | S | 1,4-Ph | H | 2,3,5,6-TetF-4-CN—Ph |
| 14-24 | 2,4-diFPh | Et | S | 1,4-Ph | H | 2,3,5,6-TetF-4-CN—Ph |
| 14-25 | 2,4-diFPh | Me | S | 1,4-Ph | Me | 2,3,5,6-TetF-4-CN—Ph |
| 14-26 | 2,4-diFPh | Me | CH$_2$ | 1,4-Ph | Me | 2,3,5,6-TetF-4-CN—Ph |
| 15-1 | 2,4-diFPh | Me | S | 1,4-Ph | H | 3,4-diCN—Ph |
| 15-2 | 2,4-diFPh | Me | S | 2,6-Np | H | 3,4-diCN—Ph |
| 15-3 | 2,4-diFPh | Me | CH$_2$ | 1,4-Ph | H | 3,4-diCN—Ph |
| 15-4 | 2,4-diFPh | Me | CH$_2$ | 2,6-Np | H | 3,4-diCN—Ph |
| 15-5 | 4-FPh | Me | S | 1,4-Ph | H | 3,4-diCN—Ph |
| 15-6 | 4-FPh | Me | S | 2,6-Np | H | 3,4-diCN—Ph |
| 15-7 | 4-FPh | Me | CH$_2$ | 1,4-Ph | H | 3,4-diCN—Ph |
| 15-8 | 4-FPh | Me | CH$_2$ | 2,6-Np | H | 3,4-diCN—Ph |
| 15-9 | 2-FPh | Me | S | 1,4-Ph | H | 3,4-diCN—Ph |
| 15-10 | 2-FPh | Me | S | 2,6-Np | H | 3,4-diCN—Ph |
| 15-11 | 2-FPh | Me | CH$_2$ | 1,4-Ph | H | 3,4-diCN—Ph |
| 15-12 | 2-FPh | Me | CH$_2$ | 2,6-Np | H | 3,4-diCN—Ph |
| 15-13 | 2,4-diClPh | Me | S | 1,4-Ph | H | 3,4-diCN—Ph |
| 15-14 | 2,4-diClPh | Me | S | 2,6-Np | H | 3,4-diCN—Ph |
| 15-15 | 2,4-diClPh | Me | CH$_2$ | 1,4-Ph | H | 3,4-diCN—Ph |
| 15-16 | 2,4-diClPh | Me | CH$_2$ | 2,6-Np | H | 3,4-diCN—Ph |
| 15-17 | 4-(CF$_3$)Ph | Me | S | 1,4-Ph | H | 3,4-diCN—Ph |

TABLE 1-continued

| No. | Ar¹ | R¹ | X | Ar² | R² | R³ |
|---|---|---|---|---|---|---|
| 15-18 | 4-(CF₃)Ph | Me | S | 2,6-Np | H | 3,4-diCN—Ph |
| 15-19 | 4-(CF₃)Ph | Me | CH₂ | 1,4-Ph | H | 3,4-diCN—Ph |
| 15-20 | 4-(CF₃)Ph | Me | CH₂ | 2,6-Np | H | 3,4-diCN—Ph |
| 15-21 | 2,4-diFPh | Me | S | 2-F-1,4-Ph | H | 3,4-diCN—Ph |
| 15-22 | 2,4-diFPh | Me | CH₂ | 2-F-1,4-Ph | H | 3,4-diCN—Ph |
| 15-23 | 2,4-diFPh | H | S | 1,4-Ph | H | 3,4-diCN—Ph |
| 15-24 | 2,4-diFPh | Et | S | 1,4-Ph | H | 3,4-diCN—Ph |
| 15-25 | 2,4-diFPh | Me | S | 1,4-Ph | Me | 3,4-diCN—Ph |
| 15-26 | 2,4-diFPh | Me | CH₂ | 1,4-Ph | Me | 3,4-diCN—Ph |
| 16-1 | 2,4-diFPh | Me | S | 1,4-Ph | H | 4-CH₃CO—Ph |
| 16-2 | 2,4-diFPh | Me | S | 2,6-Np | H | 4-CH₃CO—Ph |
| 16-3 | 2,4-diFPh | Me | CH₂ | 1,4-Ph | H | 4-CH₃CO—Ph |
| 16-4 | 2,4-diFPh | Me | CH₂ | 2,6-Np | H | 4-CH₃CO—Ph |
| 16-5 | 4-FPh | Me | S | 1,4-Ph | H | 4-CH₃CO—Ph |
| 16-6 | 4-FPh | Me | S | 2,6-Np | H | 4-CH₃CO—Ph |
| 16-7 | 4-FPh | Me | CH₂ | 1,4-Ph | H | 4-CH₃CO—Ph |
| 16-8 | 4-FPh | Me | CH₂ | 2,6-Np | H | 4-CH₃CO—Ph |
| 16-9 | 2-FPh | Me | S | 1,4-Ph | H | 4-CH₃CO—Ph |
| 16-10 | 2-FPh | Me | S | 2,6-Np | H | 4-CH₃CO—Ph |
| 16-11 | 2-FPh | Me | CH₂ | 1,4-Ph | H | 4-CH₃CO—Ph |
| 16-12 | 2-FPh | Me | CH₂ | 2,6-Np | H | 4-CH₃CO—Ph |
| 16-13 | 2,4-diClPh | Me | S | 1,4-Ph | H | 4-CH₃CO—Ph |
| 16-14 | 2,4-diClPh | Me | S | 2,6-Np | H | 4-CH₃CO—Ph |
| 16-15 | 2,4-diClPh | Me | CH₂ | 1,4-Ph | H | 4-CH₃CO—Ph |
| 16-16 | 2,4-diClPh | Me | CH₂ | 2,6-Np | H | 4-CH₃CO—Ph |
| 16-17 | 4-(CF₃)Ph | Me | S | 1,4-Ph | H | 4-CH₃CO—Ph |
| 16-18 | 4-(CF₃)Ph | Me | S | 2,6-Np | H | 4-CH₃CO—Ph |
| 16-19 | 4-(CF₃)Ph | Me | CH₂ | 1,4-Ph | H | 4-CH₃CO—Ph |
| 16-20 | 4-(CF₃)Ph | Me | CH₂ | 2,6-Np | H | 4-CH₃CO—Ph |
| 16-21 | 2,4-diFPh | Me | S | 2-F-1,4-Ph | H | 4-CH₃CO—Ph |
| 16-22 | 2,4-diFPh | Me | CH₂ | 2-F-1,4-Ph | H | 4-CH₃CO—Ph |
| 16-23 | 2,4-diFPh | H | S | 1,4-Ph | H | 4-CH₃CO—Ph |
| 16-24 | 2,4-diFPh | Et | S | 1,4-Ph | H | 4-CH₃CO—Ph |
| 16-25 | 2,4-diFPh | Me | S | 1,4-Ph | Me | 4-CH₃CO—Ph |
| 16-26 | 2,4-diFPh | Me | CH₂ | 1,4-Ph | Me | 4-CH₃CO—Ph |
| 17-1 | 2,4-diFPh | Me | S | 1,4-Ph | H | 4-CH₃COO—Ph |
| 17-2 | 2,4-diFPh | Me | S | 2,6-Np | H | 4-CH₃COO—Ph |
| 17-3 | 2,4-diFPh | Me | CH₂ | 1,4-Ph | H | 4-CH₃COO—Ph |
| 17-4 | 2,4-diFPh | Me | CH₂ | 2,6-Np | H | 4-CH₃COO—Ph |
| 17-5 | 4-FPh | Me | S | 1,4-Ph | H | 4-CH₃COO—Ph |
| 17-6 | 4-FPh | Me | S | 2,6-Np | H | 4-CH₃COO—Ph |
| 17-7 | 4-FPh | Me | CH₂ | 1,4-Ph | H | 4-CH₃COO—Ph |
| 17-8 | 4-FPh | Me | CH₂ | 2,6-Np | H | 4-CH₃COO—Ph |
| 17-9 | 2-FPh | Me | S | 1,4-Ph | H | 4-CH₃COO—Ph |
| 17-10 | 2-FPh | Me | S | 2,6-Np | H | 4-CH₃COO—Ph |
| 17-11 | 2-FPh | Me | CH₂ | 1,4-Ph | H | 4-CH₃COO—Ph |
| 17-12 | 2-FPh | Me | CH₂ | 2,6-Np | H | 4-CH₃COO—Ph |
| 17-13 | 2,4-diClPh | Me | S | 1,4-Ph | H | 4-CH₃COO—Ph |
| 17-14 | 2,4-diClPh | Me | S | 2,6-Np | H | 4-CH₃COO—Ph |
| 17-15 | 2,4-diClPh | Me | CH₂ | 1,4-Ph | H | 4-CH₃COO—Ph |
| 17-16 | 2,4-diClPh | Me | CH₂ | 2,6-Np | H | 4-CH₃COO—Ph |
| 17-17 | 4-(CF₃)Ph | Me | S | 1,4-Ph | H | 4-CH₃COO—Ph |
| 17-18 | 4-(CF₃)Ph | Me | S | 2,6-Np | H | 4-CH₃COO—Ph |
| 17-19 | 4-(CF₃)Ph | Me | CH₂ | 1,4-Ph | H | 4-CH₃COO—Ph |
| 17-20 | 4-(CF₃)Ph | Me | CH₂ | 2,6-Np | H | 4-CH₃COO—Ph |
| 17-21 | 2,4-diFPh | Me | S | 2-F-1,4-Ph | H | 4-CH₃COO—Ph |
| 17-22 | 2,4-diFPh | Me | CH₂ | 2-F-1,4-Ph | H | 4-CH₃COO—Ph |
| 17-23 | 2,4-diFPh | H | S | 1,4-Ph | H | 4-CH₃COO—Ph |
| 17-24 | 2,4-diFPh | Et | S | 1,4-Ph | H | 4-CH₃COO—Ph |
| 17-25 | 2,4-diFPh | Me | S | 1,4-Ph | Me | 4-CH₃COO—Ph |
| 17-26 | 2,4-diFPh | Me | CH₂ | 1,4-Ph | Me | 4-CH₃COO—Ph |
| 18-1 | 2,4-diFPh | Me | S | 1,4-Ph | H | 2-F-4-CN—Ph |
| 18-2 | 2,4-diFPh | Me | S | 2,6-Np | H | 2-F-4-CN—Ph |
| 18-3 | 2,4-diFPh | Me | CH₂ | 1,4-Ph | H | 2-F-4-CN—Ph |
| 18-4 | 2,4-diFPh | Me | CH₂ | 2,6-Np | H | 2-F-4-CN—Ph |
| 18-5 | 4-FPh | Me | S | 1,4-Ph | H | 2-F-4-CN—Ph |
| 18-6 | 4-FPh | Me | S | 2,6-Np | H | 2-F-4-CN—Ph |
| 18-7 | 4-FPh | Me | CH₂ | 1,4-Ph | H | 2-F-4-CN—Ph |
| 18-8 | 4-FPh | Me | CH₂ | 2,6-Np | H | 2-F-4-CN—Ph |
| 18-9 | 2-FPh | Me | S | 1,4-Ph | H | 2-F-4-CN—Ph |
| 18-10 | 2-FPh | Me | S | 2,6-Np | H | 2-F-4-CN—Ph |
| 18-11 | 2-FPh | Me | CH₂ | 1,4-Ph | H | 2-F-4-CN—Ph |
| 18-12 | 2-FPh | Me | CH₂ | 2,6-Np | H | 2-F-4-CN—Ph |
| 18-13 | 2,4-diClPh | Me | S | 1,4-Ph | H | 2-F-4-CN—Ph |
| 18-14 | 2,4-diClPh | Me | S | 2,6-Np | H | 2-F-4-CN—Ph |
| 18-15 | 2,4-diClPh | Me | CH₂ | 1,4-Ph | H | 2-F-4-CN—Ph |
| 18-16 | 2,4-diClPh | Me | CH₂ | 2,6-Np | H | 2-F-4-CN—Ph |

TABLE 1-continued

| No. | Ar¹ | R¹ | X | Ar² | R² | R³ |
|---|---|---|---|---|---|---|
| 18-17 | 4-(CF₃)Ph | Me | S | 1,4-Ph | H | 2-F-4-CN—Ph |
| 18-18 | 4-(CF₃)Ph | Me | S | 2,6-Np | H | 2-F-4-CN—Ph |
| 18-19 | 4-(CF₃)Ph | Me | CH₂ | 1,4-Ph | H | 2-F-4-CN—Ph |
| 18-20 | 4-(CF₃)Ph | Me | CH₂ | 2,6-Np | H | 2-F-4-CN—Ph |
| 18-21 | 2,4-diFPh | Me | S | 2-F-1,4-Ph | H | 2-F-4-CN—Ph |
| 18-22 | 2,4-diFPh | Me | CH₂ | 2-F-1,4-Ph | H | 2-F-4-CN—Ph |
| 18-23 | 2,4-diFPh | H | S | 1,4-Ph | H | 2-F-4-CN—Ph |
| 18-24 | 2,4-diFPh | Et | S | 1,4-Ph | H | 2-F-4-CN—Ph |
| 18-25 | 2,4-diFPh | Me | S | 1,4-Ph | Me | 2-F-4-CN—Ph |
| 18-26 | 2,4-diFPh | Me | CH₂ | 1,4-Ph | Me | 2-F-4-CN—Ph |
| 19-1 | 2,4-diFPh | Me | S | 1,4-Ph | H | 4-CN—Ph—CH₂— |
| 19-2 | 2,4-diFPh | Me | CH₂ | 1,4-Ph | H | 4-CN—Ph—CH₂— |
| 19-3 | 4-FPh | Me | S | 1,4-Ph | H | 4-CN—Ph—CH₂— |
| 19-4 | 4-FPh | Me | CH₂ | 1,4-Ph | H | 4-CN—Ph—CH₂— |
| 19-5 | 2-FPh | Me | S | 1,4-Ph | H | 4-CN—Ph—CH₂— |
| 19-6 | 2-FPh | Me | CH₂ | 1,4-Ph | H | 4-CN—Ph—CH₂— |
| 20-1 | 2,4-diFPh | Me | S | 1,4-Ph | H | 2-Thz |
| 20-2 | 2,4-diFPh | Me | CH₂ | 1,4-Ph | H | 2-Thz |
| 20-3 | 4-FPh | Me | S | 1,4-Ph | H | 2-Thz |
| 20-4 | 4-FPh | Me | CH₂ | 1,4-Ph | H | 2-Thz |
| 20-5 | 2-FPh | Me | S | 1,4-Ph | H | 2-Thz |
| 20-6 | 2-FPh | Me | CH₂ | 1,4-Ph | H | 2-Thz |
| 21-1 | 2,4-diFPh | Me | S | 1,4-Ph | H | 1-Np—CH₂— |
| 21-2 | 2,4-diFPh | Me | CH₂ | 1,4-Ph | H | 1-Np—CH₂— |
| 21-3 | 4-FPh | Me | S | 1,4-Ph | H | 1-Np—CH₂— |
| 21-4 | 4-FPh | Me | CH₂ | 1,4-Ph | H | 1-Np—CH₂— |
| 21-5 | 2-FPh | Me | S | 1,4-Ph | H | 1-Np—CH₂— |
| 21-6 | 2-FPh | Me | CH₂ | 1,4-Ph | H | 1-Np—CH₂— |
| 22-1 | 2,4-diFPh | Me | S | 1,4-Ph | H | 3-Isoxazolyl |
| 22-2 | 2,4-diFPh | Me | CH₂ | 1,4-Ph | H | 3-Isoxazolyl |
| 22-3 | 4-FPh | Me | S | 1,4-Ph | H | 3-Isoxazolyl |
| 22-4 | 4-FPh | Me | CH₂ | 1,4-Ph | H | 3-Isoxazolyl |
| 22-5 | 2-FPh | Me | S | 1,4-Ph | H | 3-Isoxazolyl |
| 22-6 | 2-FPh | Me | CH₂ | 1,4-Ph | H | 3-Isoxazolyl |
| 23-1 | 2,4-diFPh | Me | S | 1,4-Ph | H | 2-Oxazolyl |
| 23-2 | 2,4-diFPh | Me | CH₂ | 1,4-Ph | H | 2-Oxazolyl |
| 23-3 | 4-FPh | Me | S | 1,4-Ph | H | 2-Oxazolyl |
| 23-4 | 4-FPh | Me | CH₂ | 1,4-Ph | H | 2-Oxazolyl |
| 23-5 | 2-FPh | Me | S | 1,4-Ph | H | 2-Oxazolyl |
| 23-6 | 2-FPh | Me | CH₂ | 1,4-Ph | H | 2-Oxazolyl |
| 24-1 | 2,4-diFPh | Me | S | 1,4-Ph | H | 4-NH₂CO—Ph |
| 24-2 | 2,4-diFPh | Me | CH₂ | 1,4-Ph | H | 4-NH₂CO—Ph |
| 24-3 | 4-FPh | Me | S | 1,4-Ph | H | 4-NH₂CO—Ph |
| 24-4 | 4-FPh | Me | CH₂ | 1,4-Ph | H | 4-NH₂CO—Ph |
| 24-5 | 2-FPh | Me | S | 1,4-Ph | H | 4-NH₂CO—Ph |
| 24-6 | 2-FPh | Me | CH₂ | 1,4-Ph | H | 4-NH₂CO—Ph |
| 25-1 | 2,4-diFPh | Me | S | 1,4-Ph | H | 4-I—Ph |
| 25-2 | 2,4-diFPh | Me | CH₂ | 1,4-Ph | H | 4-I—Ph |
| 26-1 | 2,4-diFPh | Me | S | 1,4-Ph | H | 4-COOH—Ph |
| 26-2 | 2,4-diFPh | Me | CH₂ | 1,4-Ph | H | 4-COOH—Ph |
| 27-1 | 2,4-diFPh | Me | S | 1,4-Ph | H | 4-OH—Ph |
| 27-2 | 2,4-diFPh | Me | S | 2,6-Np | H | 4-OH—Ph |
| 27-3 | 2,4-diFPh | Me | CH₂ | 1,4-Ph | H | 4-OH—Ph |
| 27-4 | 2,4-diFPh | Me | CH₂ | 2,6-Np | H | 4-OH—Ph |
| 27-5 | 4-FPh | Me | S | 1,4-Ph | H | 4-OH—Ph |
| 27-6 | 4-FPh | Me | S | 2,6-Np | H | 4-OH—Ph |
| 27-7 | 4-FPh | Me | CH₂ | 1,4-Ph | H | 4-OH—Ph |
| 27-8 | 4-FPh | Me | CH₂ | 2,6-Np | H | 4-OH—Ph |
| 27-9 | 2-FPh | Me | S | 1,4-Ph | H | 4-OH—Ph |
| 27-10 | 2-FPh | Me | S | 2,6-Np | H | 4-OH—Ph |
| 27-11 | 2-FPh | Me | CH₂ | 1,4-Ph | H | 4-OH—Ph |
| 27-12 | 2-FPh | Me | CH₂ | 2,6-Np | H | 4-OH—Ph |
| 27-13 | 2,4-diClPh | Me | S | 1,4-Ph | H | 4-OH—Ph |
| 27-14 | 2,4-diClPh | Me | S | 2,6-Np | H | 4-OH—Ph |
| 27-15 | 2,4-diClPh | Me | CH₂ | 1,4-Ph | H | 4-OH—Ph |
| 27-16 | 2,4-diClPh | Me | CH₂ | 2,6-Np | H | 4-OH—Ph |
| 27-17 | 4-(CF₃)Ph | Me | S | 1,4-Ph | H | 4-OH—Ph |
| 27-18 | 4-(CF₃)Ph | Me | S | 2,6-Np | H | 4-OH—Ph |
| 27-19 | 4-(CF₃)Ph | Me | CH₂ | 1,4-Ph | H | 4-OH—Ph |
| 27-20 | 4-(CF₃)Ph | Me | CH₂ | 2,6-Np | H | 4-OH—Ph |
| 27-21 | 2,4-diFPh | Me | S | 2-F-1,4-Ph | H | 4-OH—Ph |
| 27-22 | 2,4-diFPh | Me | CH₂ | 2-F-1,4-Ph | H | 4-OH—Ph |
| 27-23 | 2,4-diFPh | H | S | 1,4-Ph | H | 4-OH—Ph |
| 27-24 | 2,4-diFPh | Et | S | 1,4-Ph | H | 4-OH—Ph |
| 27-25 | 2,4-diFPh | Me | S | 1,4-Ph | Me | 4-OH—Ph |
| 27-26 | 2,4-diFPh | Me | CH₂ | 1,4-Ph | Me | 4-OH—Ph |
| 28-1 | 2,4-diFPh | Me | S | 1,4-Ph | H | 4-CH₃SO₂—Ph |

TABLE 1-continued

| No. | Ar¹ | R¹ | X | Ar² | R² | R³ |
|---|---|---|---|---|---|---|
| 28-2 | 2,4-diFPh | Me | S | 2,6-Np | H | 4-CH₃SO₂—Ph |
| 28-3 | 2,4-diFPh | Me | CH₂ | 1,4-Ph | H | 4-CH₃SO₂—Ph |
| 28-4 | 2,4-diFPh | Me | CH₂ | 2,6-Np | H | 4-CH₃SO₂—Ph |
| 28-5 | 4-FPh | Me | S | 1,4-Ph | H | 4-CH₃SO₂—Ph |
| 28-6 | 4-FPh | Me | S | 2,6-Np | H | 4-CH₃SO₂—Ph |
| 28-7 | 4-FPh | Me | CH₂ | 1,4-Ph | H | 4-CH₃SO₂—Ph |
| 28-8 | 4-FPh | Me | CH₂ | 2,6-Np | H | 4-CH₃SO₂—Ph |
| 28-9 | 2-FPh | Me | S | 1,4-Ph | H | 4-CH₃SO₂—Ph |
| 28-10 | 2-FPh | Me | S | 2,6-Np | H | 4-CH₃SO₂—Ph |
| 28-11 | 2-FPh | Me | CH₂ | 1,4-Ph | H | 4-CH₃SO₂—Ph |
| 28-12 | 2-FPh | Me | CH₂ | 2,6-Np | H | 4-CH₃SO₂—Ph |
| 28-13 | 2,4-diClPh | Me | S | 1,4-Ph | H | 4-CH₃SO₂—Ph |
| 28-14 | 2,4-diClPh | Me | S | 2,6-Np | H | 4-CH₃SO₂—Ph |
| 28-15 | 2,4-diClPh | Me | CH₂ | 1,4-Ph | H | 4-CH₃SO₂—Ph |
| 28-16 | 2,4-diClPh | Me | CH₂ | 2,6-Np | H | 4-CH₃SO₂—Ph |
| 28-17 | 4-(CF₃)Ph | Me | S | 1,4-Ph | H | 4-CH₃SO₂—Ph |
| 28-18 | 4-(CF₃)Ph | Me | S | 2,6-Np | H | 4-CH₃SO₂—Ph |
| 28-19 | 4-(CF₃)Ph | Me | CH₂ | 1,4-Ph | H | 4-CH₃SO₂—Ph |
| 28-20 | 4-(CF₃)Ph | Me | CH₂ | 2,6-Np | H | 4-CH₃SO₂—Ph |
| 28-21 | 2,4-diFPh | Me | S | 2-F-1,4-Ph | H | 4-CH₃SO₂—Ph |
| 28-22 | 2,4-diFPh | Me | CH₂ | 2-F-1,4-Ph | H | 4-CH₃SO₂—Ph |
| 28-23 | 2,4-diFPh | H | S | 1,4-Ph | H | 4-CH₃SO₂—Ph |
| 28-24 | 2,4-diFPh | Et | S | 1,4-Ph | H | 4-CH₃SO₂—Ph |
| 28-25 | 2,4-diFPh | Me | S | 1,4-Ph | Me | 4-CH₃SO₂—Ph |
| 28-26 | 2,4-diFPh | Me | CH₂ | 1,4-Ph | Me | 4-CH₃SO₂—Ph |
| 29-1 | 2,4-diFPh | Me | S | 1,4-Ph | H | 4-CF₃SO₂—Ph |
| 29-2 | 2,4-diFPh | Me | S | 2,6-Np | H | 4-CF₃SO₂—Ph |
| 29-3 | 2,4-diFPh | Me | CH₂ | 1,4-Ph | H | 4-CF₃SO₂—Ph |
| 29-4 | 2,4-diFPh | Me | CH₂ | 2,6-Np | H | 4-CF₃SO₂—Ph |
| 29-5 | 4-FPh | Me | S | 1,4-Ph | H | 4-CF₃SO₂—Ph |
| 29-6 | 4-FPh | Me | S | 2,6-Np | H | 4-CF₃SO₂—Ph |
| 29-7 | 4-FPh | Me | CH₂ | 1,4-Ph | H | 4-CF₃SO₂—Ph |
| 29-8 | 4-FPh | Me | CH₂ | 2,6-Np | H | 4-CF₃SO₂—Ph |
| 29-9 | 2-FPh | Me | S | 1,4-Ph | H | 4-CF₃SO₂—Ph |
| 29-10 | 2-FPh | Me | S | 2,6-Np | H | 4-CF₃SO₂—Ph |
| 29-11 | 2-FPh | Me | CH₂ | 1,4-Ph | H | 4-CF₃SO₂—Ph |
| 29-12 | 2-FPh | Me | CH₂ | 2,6-Np | H | 4-CF₃SO₂—Ph |
| 29-13 | 2,4-diClPh | Me | S | 1,4-Ph | H | 4-CF₃SO₂—Ph |
| 29-14 | 2,4-diClPh | Me | S | 2,6-Np | H | 4-CF₃SO₂—Ph |
| 29-15 | 2,4-diClPh | Me | CH₂ | 1,4-Ph | H | 4-CF₃SO₂—Ph |
| 29-16 | 2,4-diClPh | Me | CH₂ | 2,6-Np | H | 4-CF₃SO₂—Ph |
| 29-17 | 4-(CF₃)Ph | Me | S | 1,4-Ph | H | 4-CF₃SO₂—Ph |
| 29-18 | 4-(CF₃)Ph | Me | S | 2,6-Np | H | 4-CF₃SO₂—Ph |
| 29-19 | 4-(CF₃)Ph | Me | CH₂ | 1,4-Ph | H | 4-CF₃SO₂—Ph |
| 29-20 | 4-(CF₃)Ph | Me | CH₂ | 2,6-Np | H | 4-CF₃SO₂—Ph |
| 29-21 | 2,4-diFPh | Me | S | 2-F-1,4-Ph | H | 4-CF₃SO₂—Ph |
| 29-22 | 2,4-diFPh | Me | CH₂ | 2-F-1,4-Ph | H | 4-CF₃SO₂—Ph |
| 29-23 | 2,4-diFPh | H | S | 1,4-Ph | H | 4-CF₃SO₂—Ph |
| 29-24 | 2,4-diFPh | Et | S | 1,4-Ph | H | 4-CF₃SO₂—Ph |
| 29-25 | 2,4-diFPh | Me | S | 1,4-Ph | Me | 4-CF₃SO₂—Ph |
| 29-26 | 2,4-diFPh | Me | CH₂ | 1,4-Ph | Me | 4-CF₃SO₂—Ph |
| 30-1 | 2,4-diFPh | Me | S | 1,4-Ph | H | 2-CH₃O-5-Pyr |
| 30-2 | 2,4-diFPh | Me | CH₂ | 1,4-Ph | H | 2-CH₃O-5-Pyr |
| 31-1 | 2,4-diFPh | Me | S | 1,4-Ph | H | 2-CHF₂CF₂CH₂O-5-Pyr |
| 31-2 | 2,4-diFPh | Me | CH₂ | 1,4-Ph | H | 2-CHF₂CF₂CH₂O-5-Pyr |
| 32-1 | 2,4-diFPh | Me | S | 1,4-Ph | H | 4-(Me₂(HO)C)—Ph |
| 32-2 | 2,4-diFPh | Me | CH₂ | 1,4-Ph | H | 4-(Me₂(HO)C)—Ph |
| 33-1 | 2,4-diFPh | Me | S | 1,4-Ph | H | 4-CNCH₂CH₂—Ph |
| 33-2 | 2,4-diFPh | Me | CH₂ | 1,4-Ph | H | 4-CNCH₂CH₂—Ph |
| 34-1 | 2,4-diFPh | Me | S | 1,4-Ph | H | 4-SH—Ph |
| 34-2 | 2,4-diFPh | Me | CH₂ | 1,4-Ph | H | 4-SH—Ph |
| 35-1 | 2,4-diFPh | Me | S | 1,4-Ph | H | 4-CNCH₂O—Ph |
| 35-2 | 2,4-diFPh | Me | CH₂ | 1,4-Ph | H | 4-CNCH₂O—Ph |
| 36-1 | 2,4-diFPh | Me | S | 1,4-Ph | H | 4-CNCH₂CH₂O—Ph |
| 36-2 | 2,4-diFPh | Me | CH₂ | 1,4-Ph | H | 4-CNCH₂CH₂O—Ph |
| 37-1 | 2,4-diFPh | Me | S | 1,4-Ph | H | 4-CH₂OHCF₂CF₂CH₂O—Ph |
| 37-2 | 2,4-diFPh | Me | CH₂ | 1,4-Ph | H | 4-CH₂OHCF₂CF₂CH₂O—Ph |
| 38-1 | 2,4-diFPh | Me | S | 1,4-Ph | H | 4-CN-1-Np |
| 38-2 | 2,4-diFPh | Me | S | 2,6-Np | H | 4-CN-1-Np |
| 38-3 | 2,4-diFPh | Me | CH₂ | 1,4-Ph | H | 4-CN-1-Np |
| 38-4 | 2,4-diFPh | Me | CH₂ | 2,6-Np | H | 4-CN-1-Np |
| 38-5 | 4-FPh | Me | S | 1,4-Ph | H | 4-CN-1-Np |
| 38-6 | 4-FPh | Me | S | 2,6-Np | H | 4-CN-1-Np |
| 38-7 | 4-FPh | Me | CH₂ | 1,4-Ph | H | 4-CN-1-Np |
| 38-8 | 4-FPh | Me | CH₂ | 2,6-Np | H | 4-CN-1-Np |
| 38-9 | 2-FPh | Me | S | 1,4-Ph | H | 4-CN-1-Np |
| 38-10 | 2-FPh | Me | S | 2,6-Np | H | 4-CN-1-Np |

TABLE 1-continued

| No. | Ar¹ | R¹ | X | Ar² | R² | R³ |
|---|---|---|---|---|---|---|
| 38-11 | 2-FPh | Me | CH₂ | 1,4-Ph | H | 4-CN-1-Np |
| 38-12 | 2-FPh | Me | CH₂ | 2,6-Np | H | 4-CN-1-Np |
| 38-13 | 2,4-diClPh | Me | S | 1,4-Ph | H | 4-CN-1-Np |
| 38-14 | 2,4-diClPh | Me | S | 2,6-Np | H | 4-CN-1-Np |
| 38-15 | 2,4-diClPh | Me | CH₂ | 1,4-Ph | H | 4-CN-1-Np |
| 38-16 | 2,4-diClPh | Me | CH₂ | 2,6-Np | H | 4-CN-1-Np |
| 38-17 | 4-(CF₃)Ph | Me | S | 1,4-Ph | H | 4-CN-1-Np |
| 38-18 | 4-(CF₃)Ph | Me | S | 2,6-Np | H | 4-CN-1-Np |
| 38-19 | 4-(CF₃)Ph | Me | CH₂ | 1,4-Ph | H | 4-CN-1-Np |
| 38-20 | 4-(CF₃)Ph | Me | CH₂ | 2,6-Np | H | 4-CN-1-Np |
| 38-21 | 2,4-diFPh | Me | S | 2-F-1,4-h | H | 4-CN-1-Np |
| 38-22 | 2,4-diFPh | Me | CH₂ | 2-F-1,4-h | H | 4-CN-1-Np |
| 38-23 | 2,4-diFPh | H | S | 1,4-Ph | H | 4-CN-1-Np |
| 38-24 | 2,4-diFPh | Et | S | 1,4-Ph | H | 4-CN-1-Np |
| 38-25 | 2,4-diFPh | Me | S | 1,4-Ph | Me | 4-CN-1-Np |
| 38-26 | 2,4-diFPh | Me | CH₂ | 1,4-Ph | Me | 4-CN-1-Np |
| 39-1 | 2,4-diFPh | Me | S | 1,4-Ph | H | benzothiazol-2-yl |
| 39-2 | 2,4-diFPh | Me | CH₂ | 1,4-Ph | H | benzothiazol-2-yl |
| 40-1 | 2,4-diFPh | Me | S | 1,4-Ph | H | 2,4-diCl—Ph |
| 40-2 | 2,4-diFPh | Me | CH₂ | 1,4-Ph | H | 2,4-diCl—Ph |
| 41-1 | 2,4-diFPh | Me | S | 1,4-Ph | H | 2-Cl-4-CF₃—Ph |
| 41-2 | 2,4-diFPh | Me | CH₂ | 1,4-Ph | H | 2-Cl-4-CF₃—Ph |

In Table 1 the following abbreviations are used with the following meanings.

Me: methyl,

CN: cyano (attached via a carbon atom), Et: ethyl,

Ph: phenyl, 1,4-Ph: 1,4-phenylene, Np: naphthyl, 2,6-Np: 2,6-naphthylene, Pyr: pyridyl, Thz: thiazolyl, Tet: tetra.

For example, exemplification compound number 1-1 has the following formula (Ia);

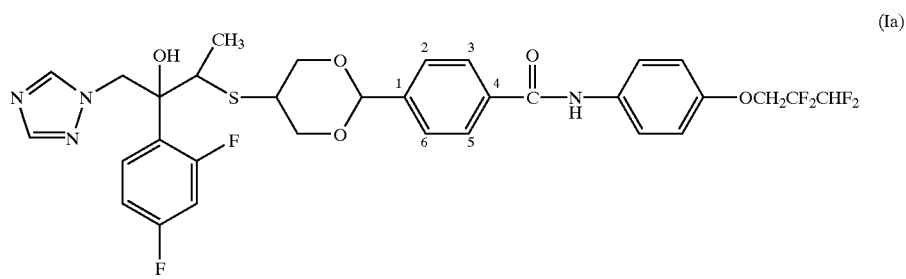

(Ia)

exemplification compound number 14-4 has the following formula (Ib);

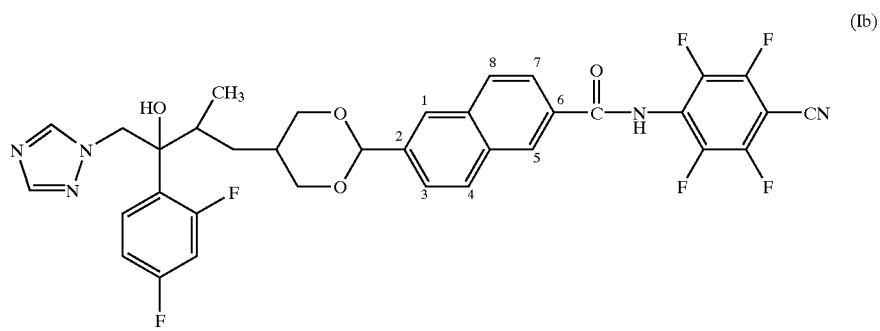

(Ib)

and;

exemplification compound number 1-21 has the following formula (Ic).

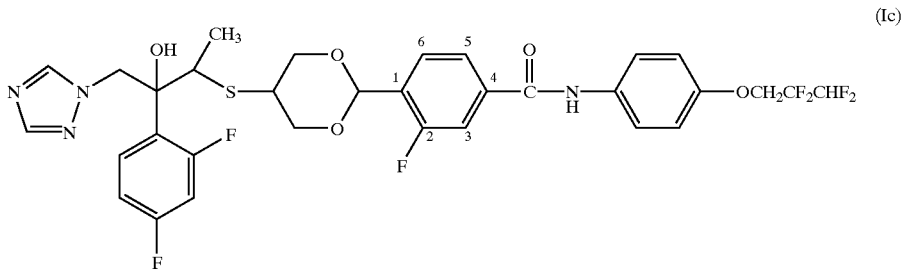

(Ic)

Of the exemplification compounds, preferred compounds are those of exemplification compound numbers:
1-1, 1-2, 1-3, 1-4, 1-9, 1-11, 1-21, 1-22, 2-1, 2-2, 2-3, 2-4, 2-9, 2-11, 2-21, 2-22, 2-25, 3-1, 3-2, 3-3, 3-4, 3-9, 3-11, 3-21, 3-22, 4-1, 4-2, 4-3, 4-4, 4-9, 4-11, 4-21, 4-22, 4-25, 5-1, 5-2, 5-3, 5-4, 5-9, 5-11, 5-21, 5-22, 6-1, 6-2, 6-3, 6-4, 6-9, 6-11, 6-21, 6-22, 7-1, 7-2, 7-3, 7-4, 7-9, 7-11, 7-21, 7-22, 8-1, 8-2, 8-3, 8-4, 8-9, 8-11, 8-21, 8-22, 9-1, 9-2, 9-3, 9-4, 9-9, 9-11, 9-21, 9-22, 10-1, 10-2, 10-3, 10-4, 10-9, 10-11, 10-21, 10-22, 11-1, 11-2, 11-3, 11-4, 11-9, 11-11, 11-21, 11-22, 13-1, 13-2, 13-3, 13-4, 13-9, 13-11, 13-21, 13-22, 14-1, 14-3, 15-1, 15-3, 16-1, 16-2, 16-3, 16-4, 16-9, 16-11, 16-21, 16-22, 17-1, 17-2, 17-3, 17-4, 17-9, 17-11, 17-21, 17-22, 18-1, 18-2, 18-3, 18-4, 18-9, 18-11, 18-21, 18-22, 19-1, 19-2, 24-1, 24-2, 25-1, 26-1, 27-1, 27-2, 27-3, 27-4, 27-9, 27-11, 27-21, 27-22, 28-1, 28-2, 28-3, 28-4, 28-9, 28-11, 28-21, 28-22, 29-1, 29-2, 29-3, 29-4, 29-9, 29-11, 29-21, 29-22, 40-1, 40-2, 41-1 and 41-2.

Of these compounds (I) more preferred compounds include:

4-[5-[[2-(2,4-difluorophenyl)-2-hydroxy-1-methyl-3-(1H-1,2,4-triazol-1-yl)propyl]thio]-1,3-dioxan-2-yl]-4'-(2,2,3,3-tetrafluoropropoxy)benzanilide (exemplification compound number 1-1), 6-[5-[[2-(2,4-difluorophenyl)-2-hydroxy-1-methyl-3-(1H-1,2,4-triazol-1-yl)propyl]thio]-1,3-dioxan-2-yl]-4'-(2,2,3,3-tetrafluoropropoxy)-2-naphthoanilide (exemplification compound number 1-2), 4-[5-[3-(2,4-difluorophenyl)-3-hydroxy-2-methyl-4-(1H-1,2,4-triazol-1-yl)butyl]-1,3-dioxan-2-yl]-4'-(2,2,3,3-tetrafluoropropoxy)benzanilide (exemplification compound number 1-3), 4'-cyano-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 2-1), 4'-cyano-6-[5-[[2-(2,4-difluorophenyl)-2-hydroxy-1-methyl-3-(1H-1,2,4-triazol-1-yl)propyl]thio]-1,3-dioxan-2-yl]-2-naphthoanilide (exemplification compound number 2-2), 4'-cyano-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 2-3), 4'-cyano-6-[5-[3-(2,4-difluorophenyl)-3-hydroxy-2-methyl-4-(1H-1,2,4-triazol-1-yl)butyl]-1,3-dioxan-2-yl]-2-naphthoanilide (exemplification compound number 2-4), 4'-cyano-4-[5-[[2-(2,4-difluorophenyl)-2-hydroxy-1-methyl-3-(1H-1,2,4-triazol-1-yl)propyl]thio]-1,3-dioxan-2-yl]-3-fluorobenzanilide (exemplification compound number 2-21), 4'-cyano-3-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 2-25), 4'-(cyanomethyl)-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 3-1), 4'-chloro-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 4-1), 4'-chloro-6-[5-[[2-(2,4-difluorophenyl)-2-hydroxy-1-methyl-3-(1H-1,2,4-triazol-1-yl)propyl]thio]-1,3-dioxan-2-yl]-2-naphthoanilide (exemplification compound number 4-2), 4'-chloro-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 4-3), 4'-chloro-6-[5-[3-(2,4-difluorophenyl)-3-hydroxy-2-methyl-4-(1H-1,2,4-triazol-1-yl)butyl]-1,3-dioxan-2-yl]-2-naphthoanilide (exemplification compound number 4-4), 4'-chloro-3-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 4-25), 4-[5-[[2-(2,4-difluorophenyl)-2-hydroxy-1-methyl-3-(1H-1,2,4-triazol-1-yl)propyl]thio]-1,3-dioxan-2-yl]-4'-fluorobenzanilide (exemplification compound number 5-1), 6-[5-[[2-(2,4-difluorophenyl)-2-hydroxy-1-methyl-3-(1H-1,2,4-triazol-1-yl)propyl]thio]-1,3-dioxan-2-yl]-4'-fluoro-2-naphthoanilide (exemplification compound number 5-2), 4-[5-[3-(2,4-difluorophenyl)-3-hydroxy-2-methyl-4-(1H-1,2,4-triazol-1-yl)butyl]-1,3-dioxan-2-yl]-4'-fluorobenzanilide (exemplification compound number 5-3), 6-[5-[3-(2,4-difluorophenyl)-3-hydroxy-2-methyl-4-(1H-1,2,4-triazol-1-yl)butyl]-1,3-dioxan-2-yl]-4'-fluoro-2-naphthoanilide (exemplification compound number 5-4), 4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethyl)benzanilide (exemplification compound number 6-1), 6-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethyl)-2-naphthoanilide (exemplification compound number 6-2), 4-[5-[3-(2,4-difluorophenyl)-3-hydroxy-2-methyl-4-(1H-1,2,4-triazol-1-yl)butyl]-1,3-dioxan-2-yl]-4'-(trifluoromethyl)benzanilide (exemplification compound number 6-3), 6-[5-[3-(2,4-difluorophenyl)-3-hydroxy-2-methyl-4-(1H-1,2,4-triazol-1-yl)butyl]-1,3-dioxan-2-yl]-4'-(trifluoromethyl)-2-naphthoanilide (exemplification compound number 6-4), 4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethoxy)benzanilide (exemplification compound number 7-1), 6-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethoxy)-2-naphthoanilide (exemplification compound number 7-2), 4-[5-[3-(2,4-difluorophenyl)-3-hydroxy-2-methyl-4-(1H-1,2,4-triazol-1-yl)butyl]-1,3-dioxan-2-yl]-4'-(trifluoromethoxy)benzanilide (exemplification compound number 7-3), 6-[5-[3-(2,4-difluorophenyl)-3-hydroxy-2-methyl-4-(1H-1,2,4-triazol-1-yl)butyl]-1,3-dioxan-2-yl]-4'-(trifluoromethoxy)-2-naphthoanilide (exemplification compound number 7-4), 4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethylthio)benzanilide (exemplification compound number 8-1), 6-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethylthio)-2-naphthoanilide (exemplification compound number 8-2), 4-[5-[3-(2,4-difluorophenyl)-3-hydroxy-2-methyl-4-(1H-1,2,4-triazol-1-yl)butyl]-1,3-dioxan-2-yl]-4'-(trifluoromethylthio)benzanilide (exemplification compound number 8-3), 6-[5-[3-(2,4-difluorophenyl)-3-hydroxy-2-methyl-4-(1H-1,2,4-triazol-1-yl)butyl]-1,3-dioxan-2-yl]-4'-(trifluoromethylthio)-2-naphthoanilide (exemplification compound number 8-4), 4-[5-[[2-(2,4-difluorophenyl)-2-hydroxy-1-methyl-3-(1H-1,2,4-triazol-1-yl)propyl]thio]-1,3-dioxan-2-yl]-4'-methylbenzanilide (exemplification compound number 9-1), 4-[5-[3-(2,4-difluorophenyl)-3-hydroxy-2-methyl-4-(1H-1,2,4-triazol-1-yl)butyl]-1,3-dioxan-2-yl]-4'-methylbenzanilide (exemplification compound number 9-3), 4'-bromo-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 10-1), 4'-bromo-6-[5-[[2-(2,4-difluorophenyl)-2-hydroxy-1-methyl-3-(1H-1,2,4-triazol-1-yl)propyl]thio]-1,3-dioxan-2-yl]-2-naphthoanilide (exemplification compound number 10-2), 4'-bromo-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 10-3), 4'-bromo-6-[5-[3.-(2,4-difluorophenyl)-3-hydroxy-2-methyl-4-(1H-1,2,4-triazol-1-yl)butyl]-1,3-dioxan-2-yl]-2-naphthoanilide (exemplification compound number 10-4), 3'-chloro-4'-cyano-4-[S-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 11-1), 3'-chloro-4'-cyano-6-[5-[[2-(2,4-difluorophenyl)-2-hydroxy-1-methyl-3-(1H-1,2,4-triazol-1-yl)propyl]thio]-1,3-dioxan-2-yl]-2-naphthoanilide (exemplification compound number 11-2), 3'-chloro-4'-cyano-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 11-3), 3'-chloro-4'-cyano-6-[5-[3-(2,4-difluorophenyl)-3-hydroxy-2-methyl-4-(1H-1,2,4-triazol-1-yl)butyl]-1,3-dioxan-2-yl]-2-naphthoanilide (exemplification compound number 11-4), 4-[5-[[2-(2,4-difluorophenyl)-2-hydroxy-1-methyl-3-(1H-1,2,4-triazol-1-yl)propyl]thio]-1,3-dioxan-2-yl]-4'-nitrobenzanilide (exemplification compound number 13-1), 4-[5-[3-(2,4-difluorophenyl)-3-hydroxy-2-methyl-4-(1H-1,2,4-triazol-1-yl)butyl]-1,3-dioxan-2-yl]-4'-nitrobenzanilide (exemplification compound number 13-3), 4'-cyano-4-[5-[[2-(2,4-difluorophenyl)-2-hydroxy-1-methyl-3-(1H-1,2,4-triazol-1-yl)propyl]thio)-1,3-dioxan-2-yl-2',3',5',6'-tetrafluoro]benzanilide (exemplification compound number 14-1), 4'-cyano-4-[5-[3-(2,4-difluorophenyl)-3-hydroxy-2-methyl-4-(1H-1,2,4-triazol-1-yl)butyl]-1,3-dioxan-2-yl]-2',3',5',6'-tetrafluorobenzanilide (exemplification compound number 14-3), 3',4'-dicyano-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 15-1), 3',4'-dicyano-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 15-3), 4'-acetyl-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 16-1), 4'-acetyl-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 16-3), 4'-acetoxy-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 17-1), 4'-acetoxy-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 17-3), 4'-cyano-2'-fluoro-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 18-1), 4'-cyano-2'-fluoro-6-[5-[[2-(2,4-difluorophenyl)-2-hydroxy-1-methyl-3-(1H-1,2,4-triazol-1-yl)propyl]thio]-1,3-dioxan-2-yl]-2-naphthoanilide (exemplification compound number 18-2), 4'-cyano-2'-fluoro-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 18-3), 4'-cyano-2'-fluoro-6-[5-[3-(2,4-difluorophenyl)-3-hydroxy-2-methyl-4-(1H-1,2,4-triazol-1-yl)butyl]-1,3-dioxan-2-yl]-2-naphthoanilide (exemplification compound number 18-4), 4'-carbamoyl-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 24-1), 4-[5-[[2-(2,4-difluorophenyl)-2-hydroxy-1-methyl-3-(1H-1,2,4-triazol-1-yl)propyl]thio]-1,3-dioxan-2-yl]-4'-iodobenzanilide (exemplification compound number 25-1), 4-[N-[4-[5-[[2-(2,4-difluorophenyl)-2-hydroxy-1-methyl-3-(1H-1,2,4-triazol-1-yl)propyl]thio]-1,3-dioxan-2-yl]benzoyl]amino]benzoic acid (exemplification compound number 26-1), 4-[5-[[2-(2,4-difluorophenyl)-2-hydroxy-1-methyl-3-(1H-1,2,4-triazol-1-yl)propyl]thio]-1,3-dioxan-2-yl]-4'-hydroxybenzanilide (exemplification compound number 27-1), 6-[5-[[2-(2,4-difluorophenyl)-2-hydroxy-1-methyl-3-(1H-1,2,4-triazol-1-yl)propyl]thio]-1,3-dioxan-2-yl]-4'-hydroxy-2-naphthoanilide (exemplification compound number 27-2), 4-[5-[3-(2,4-difluorophenyl)-3-hydroxy-2-methyl-4-(1H-1,2,4-triazol-1-yl)butyl]-1,3-dioxan-2-yl]-4'-hydroxybenzanilide (exemplification compound number 27-3), 6-[5-[3-(2,4-difluorophenyl)-3-hydroxy-2-methyl-4-(1H-1,2,4-triazol-1-yl)butyl]-1,3-dioxan-2-yl]-4'-hydroxy-2-naphthoanilide (exemplification compound number 27-4), 4-[5-[[2-(2,4-difluorophenyl)-2-hydroxy-1-methyl-3-(1H-1,2,4-triazol-1-yl)propyl]thio]-1,3-dioxan-2-yl]-4'-(methanesulfonyl)benzanilide (exemplification compound number 28-1), 6-[5-[[2-(2,4-difluorophenyl)-2-hydroxy-1-methyl-3-(1H-1,2,4-triazol-1-yl)propyl]thio]-1,3-dioxan-2-yl]-4'-(methanesulfonyl)-2-naphthoanilide (exemplification compound number 28-2), 4-[5-[3-(2,4-difluorophenyl)-3-hydroxy-2-methyl-4-(1H-1,2,4-triazol-1-yl)butyl]-1,3-dioxan-2-yl]-4'-(methanesulfonyl)benzanilide (exemplification compound number 28-3), 6-[5-[3-(2,4-difluorophenyl)-3-hydroxy-2-methyl-4-(1H-1,2,4-triazol-1-yl)butyl]-1,3-dioxan-2-yl]-4'-(methanesulfonyl)-2-naphthoanilide (exemplification compound number 28-4), 4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethanesulfonyl)benzanilide (exemplification compound number 29-1), 6-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethanesulfonyl)-2-naphthoanilide (exemplification compound number 29-2), 4-[5-[3-(2,4-difluorophenyl)-3-hydroxy-2-methyl-4-(1H-1,2,4-triazol-1-yl)butyl]-1,3-dioxan-2-yl]-4'-(trifluoromethanesulfonyl)benzanilide (exemplification compound number 29-3), 6-[5-[3-(2,4-difluorophenyl)-3-hydroxy-2-methyl-4-(1H-1,2,4-triazol-1-yl)butyl]-1,3-dioxan-2-yl]-4'-(trifluoromethanesulfonyl)-2-naphthoanilide (exemplification compound number 29-4), 2',4'-dichloro-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 40-1), 2',4'-dichloro-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 40-2), 2'-chloro-4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethyl)benzanilide (exemplification compound number 41-1), and 2'-chloro-4-[5-[3-(2,4-difluorophenyl)-3-hydroxy-2-methyl-4-(1H-1,2,4-triazol-1-yl)butyl]-1,3-dioxan-2-yl]-4'-(trifluoromethyl)benzanilide (exemplification compound number 41-2).

Of these compounds (I), still more preferred compounds include:

4-[5-[[2-(2,4-difluorophenyl)-2-hydroxy-1-methyl-3-(1H-1,2,4-triazol-1-yl)propyl]thio]-1,3-dioxan-2-yl]-4'-(2,2,3,3-tetrafluoropropoxy)benzanilide (exemplification compound number 1-1), 4-[5-[3-(2,4-difluorophenyl)-3-hydroxy-2-methyl-4-(1H-1,2,4-triazol-1-yl)butyl]-1,3-dioxan-2-yl]-4'-(2,2,3,3-tetrafluoropropoxy)benzanilide (exemplification compound number 1-3), 4'-cyano-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 2-1), 4'-cyano-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 2-3), 4'-chloro-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 4-1), 4'-chloro-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 4-3), 4-[5-[[2-(2,4-difluorophenyl)-2-hydroxy-1-methyl-3-(1H-1,2,4-triazol-1-yl)propyl]thio]-1,3-dioxan-2-yl]-4'-fluorobenzanilide (exemplification compound number 5-1), 4-[5-[3-(2,4-difluorophenyl)-3-hydroxy-2-methyl-4-(1H-1,2,4-triazol-1-yl)butyl]-1,3-dioxan-2-yl]-4'-fluorobenzanilide (exemplification compound number 5-3), 4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethyl)benzanilide (exemplification compound number 6-1), 4-[5-[3-(2,4-difluorophenyl)-3-hydroxy-2-methyl-4-(1H-1,2,4-triazol-1-yl)butyl]-1,3-dioxan-2-yl]-4'-

(trifluoromethyl)benzanilide (exemplification compound number 6-3),

4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethoxy)benzanilide (exemplification compound number 7-1), 4-[5-[3-(2,4-difluorophenyl)-3-hydroxy-2-methyl-4-(1H-1,2,4-triazol-1-yl)butyl]-1,3-dioxan-2-yl]-4'-(trifluoromethoxy)benzanilide (exemplification compound number 7-3), 4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethylthio)benzanilide (exemplification compound number 8-1), 4-[5-[3-(2,4-difluorophenyl)-3-hydroxy-2-methyl-4-(1H-1,2,4-triazol-1-yl)butyl]-1,3-dioxan-2-yl]-4'-(trifluoromethylthio)benzanilide (exemplification compound number 8-3), 4-[5-[[2-(2,4-difluorophenyl)-2-hydroxy-1-methyl-3-(1H-1,2,4-triazol-1-yl)propyl]thio]-1,3-dioxan-2-yl]-4'-methylbenzanilide (exemplification compound number 9-1), 4-[5-[3-(2,4-difluorophenyl)-3-hydroxy-2-methyl-4-(1H-1,2,4-triazol-1-yl)butyl]-1,3-dioxan-2-yl]-4'-methylbenzanilide (exemplification compound number 9-3), 3'-chloro-4'-cyano-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 11-1), 3'-chloro-4'-cyano-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 11-3), 4'-cyano-2'-fluoro-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 18-1), 4'-cyano-2'-fluoro-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 18-3), 4-[5-[[2-(2,4-difluorophenyl)-2-hydroxy-1-methyl-3-(1H-1,2,4-triazol-1-yl)propyl]thio]-1,3-dioxan-2-yl]-4'-hydroxybenzanilide (exemplification compound number 27-1), 4-[5-[3-(2,4-difluorophenyl)-3-hydroxy-2-methyl-4-(1H-1,2,4-triazol-1-yl)butyl]-1,3-dioxan-2-yl]-4'-hydroxybenzanilide (exemplification compound number 27-3), 4-[5-[[2-(2,4-difluorophenyl)-2-hydroxy-1-methyl-3-(1H-1,2,4-triazol-1-yl)propyl]thio]-1,3-dioxan-2-yl]-4'-(methanesulfonyl)benzanilide (exemplification compound number 28-1), 4-[5-[3-(2,4-difluorophenyl)-3-hydroxy-2-methyl-4-(1H-1,2,4-triazol-1-yl)butyl]-1,3-dioxan-2-yl]-4'-(methanesulfonyl)benzanilide (exemplification compound number 28-3), 4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethanesulfonyl)benzanilide (exemplification compound number 29-1), 4-[5-[3-(2,4-difluorophenyl)-3-hydroxy-2-methyl-4-(1H-1,2,4-triazol-1-yl)butyl]-1,3-dioxan-2-yl]-4'-(trifluoromethanesulfonyl)benzanilide (exemplification compound number 29-3), 2',4'-dichloro-4-[5-[[2-(2,4-difluorophenyl)-2-hydroxy-1-methyl-3-(1H-1,2,4-triazol-1-yl)propyl]thio]-1,3-dioxan-2-yl]benzanilide (exemplification compound number 40-1), 2',4'-dichloro-4-[5-[3-(2,4-difluorophenyl)-3-hydroxy-2-methyl-4-(1H-1,2,4-triazol-1-yl)butyl]-1,3-dioxan-2-yl]benzanilide (exemplification compound number 40-2), 2'-chloro-4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethyl)benzanilide (exemplification compound number 41-1), and 2'-chloro-4-[5-[3-(2,4-difluorophenyl)-3-hydroxy-2-methyl-4-(1H-1,2,4-triazol-1-yl)butyl]-1,3-dioxan-2-yl]-4'-(trifluoromethyl)benzanilide (exemplification compound number 41-2).

Of these compounds (I) particularly preferred compounds include:

4'-cyano-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide (exemplification compound number 2-1), 4'-cyano-4-[trans-5-[(2S,3R)-3-(2,4-difluorophenyl)-3-hydroxy-2-methyl-4-(1H-1,2,4-triazol-1-yl)butyl]-1,3-dioxan-2-yl]benzanilide (exemplification compound number 2-3), 4'-chloro-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide (exemplification compound number 4-1), and 4'-chloro-4-[trans-5-[(2S,3R)-3-(2,4-difluorophenyl)-3-hydroxy-2-methyl-4-(1H-1,2,4-triazol-1-yl)butyl]-1,3-dioxan-2-yl]benzanilide (exemplification compound number 4-3), The compound (I) of the present invention can be easily prepared by Method A or B illustrated below.

[Method A]

Method A is a process for preparation of compound (I) and is illustrated by the following reaction scheme.

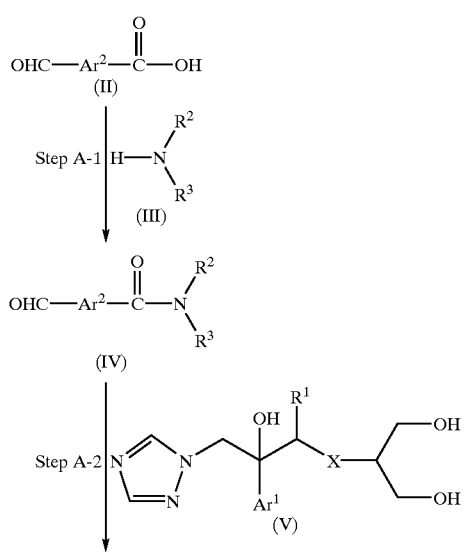

-continued

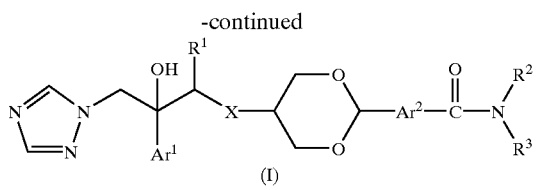

(I)

In the above reaction scheme $Ar^1$, $Ar^2$, X, $R^1$, $R^2$ and $R^3$ have the same meanings as described above.

In Method A, the reaction of a carboxylic acid compound of formula (II) or a reactive derivative thereof with an amine compound of formula (III) to give an amide compound of formula (IV) (Step A-1) is followed by the reaction of the compound of formula (IV) with a compound of formula (V) to afford a compound of formula (I) (Step A-2). Each step of Method A is described below.

Step A-1 is a process for preparation of an amide compound of formula (IV) and comprises the reaction of a carboxylic acid compound of formula (II) or a reactive derivative thereof with an amine compound of formula (III) in an inert solvent.

The carboxylic acid compound of formula (II) is commercially available or can be prepared by techniques well known to those skilled in the art. A carboxylic acid compound of formula (II), for example, can be obtained by methyl-esterification reaction of a dicarboxylic acid compound $(Ar^2(CO_2H)_2)$, reduction of one ester group of the esterified compound $(Ar^2(CO_2CH_3)_2)$ with Red-Al or the like, oxidation of the product with activated manganese dioxide, followed by hydrolysis of the formyl-ester compound $(Ar^2(CO_2CH_3)(CHO))$.

The amine compound of formula (III) is also commercially available or can be prepared by techniques known to those skilled in the art.

The solvent used in Step A-1 is not particularly limited provided that it has no adverse effect on the reaction and that it dissolves the starting materials to some extent. Such solvents include aprotic solvents, for example, halogenated hydrocarbons such as dichloromethane, chloroform or 1,2-dichloroethane; aromatic hydrocarbons such as benzene, toluene or xylene; ethers such as diethyl ether or tetrahydrofuran; nitriles such as acetonitrile; heteroaryl bases containing one or more nitrogen atoms such as pyridine; or mixtures thereof. Of these solvents, preferred solvents include halogenated hydrocarbons, ethers and heteroaryl bases containing one or more nitrogen atoms. Dichloromethane, tetrahydrofuran or pyridine is particularly preferred.

When the carboxylic acid compound of formula (II) is used in Step A-1, a coupling reagent can be used. Said coupling reagent is not particularly limited provided that it can usually be used as a coupling reagent in organic synthesis. Examples of such reagents include carbodiimides such as dicyclohexylcarbodiimide.

When the reactive derivative of the carboxylic acid compound is used in Step A-1, said carboxylic acid compound of formula (II) is converted to a reactive compound of formula OHC-$Ar^2$-COZ (wherein Z represents a leaving group, for example, a halogen atom, an azido group, a cyano group, a $C_{1-6}$ alkylsulfonyloxy group such as a methanesulfonyloxy group, a halogeno-$C_{1-6}$-alkylsulfonyloxy group such as a trifluoromethanesulfonyloxy group, a $C_{1-6}$ alkanoyloxy group such as a pivaloyloxy group, or a heteroaryl group such as an imidazolyl group or a triazolyl group) or a compound of formula (OHC-$Ar^2$-CO)$_2$O. The reaction of Step A-1 can be accomplished by the reaction of said reactive derivative of the carboxylic acid compound of formula (II) with a compound of formula (III) in the presence of a base such as triethylamine, diisopropylethylamine, pyridine or 4-(N,N-dimethylamino)pyridine.

Reagents leading to a reactive derivative of a carboxylic acid compound of formula (II) include, for example, thionyl halides such as thionyl chloride; reactive phosphoric acid derivatives such as phosphorus oxychloride or diphenylphosphoryl azide; acid chlorides such as pivaloyl chloride, oxalyl chloride and the like; reactive sulfonic acid derivatives such as methanesulfonyl chloride or trifluoromethanesulfonic acid anhydride; reactive carbonate derivatives such as phosgene, trichloromethyl chloroformate, triphosgene or 1,1'-carbonyldiimidazole; reactive oxalic acid derivatives such as oxalyl chloride; preferably thionyl chloride or oxalyl chloride. The amount of the reagent is in the range of from 1 to 10 equivalents of the amount of the carboxylic acid compound of formula (II), preferably in the range of 1 to 2 equivalents.

The amount of the amine compound of formula (III) is in the range from 0.5 to 2 molar equivalents of the amount of the carboxylic acid compound of formula (II) or the reactive derivative thereof, preferably in the range of 0.9 to 1.2 molar equivalents.

The reaction temperature of Step A-1 depends on various factors such as the starting material, the reagent and the solvent and is usually between −20° C. and the boiling point of the reaction solvent, preferably between 0° C. and room temperature.

The reaction time of Step A-1 depends on various factors such as the starting material, the reagent, the solvent and the reaction temperature. It is usually from 10 minutes to 24 hours, preferably from 1 to 2 hours.

After the reaction of Step A-1, the desired compound (IV) is isolated from the reaction mixture according to conventional techniques. For example, the reaction mixture, or the residue obtained by concentration of the reaction mixture, is partitioned between water and an organic solvent immiscible with water; the organic layer is then washed with water and then concentrated to afford the desired compound.

Step A-2 can be accomplished by the reaction of an aldehyde compound of formula (IV) with an alcohol compound of formula (V) in the presence of an acetalization reagent in an inert solvent, water produced during the reaction of Step A-2 being removed from the reaction mixture during said reaction.

In Step A-2, a salt of alcohol compound (V) or a compound of formula (VI) (wherein $Ar^1$, $R^1$ and X have the same meanings as described above; and $R^7$ represents a $C_{1-6}$ alkyl group or a $C_{6-14}$ aryl group) can be also used as a starting material instead of an alcohol compound of formula (V).

(VI)

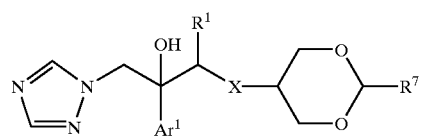

The "$C_{1-6}$ alkyl group" in the definition of $R^7$ includes a straight or branched chain alkyl group having 1 to 6 carbons, for example, a methyl, ethyl, propyl, isopropyl, butyl, isobutyl, s-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group, preferably a straight or branched chain alkyl group having 1 to 4 carbons.

The "$C_{6-14}$ aryl group" includes an aromatic hydrocarbon group having 6 to 14 carbons, for example a phenyl group, an indenyl group, a naphthyl group or an anthracenyl group, preferably a phenyl group. Said "aryl group" may optionally be fused to a cycloalkyl group having 3 to 10 carbons, for example a 2-indanyl group.

Of these groups, $R^7$ is preferably a phenyl group.

The alcohol compound of formula (V) can be prepared by the same procedure as or a similar procedure to that disclosed in the specifications of Japanese Patent Application Publication Nos. Hei-8-333350 and Hei-11-80135.

The compound of formula (VI) can be obtained as an intermediate in the process for preparation of the alcohol compound of formula (V) described in the above specifications. A salt of the alcohol compound of formula (V) can be obtained by removal of the protecting group of the compound of formula (VI).

The two primary hydroxyl groups of the alcohol compound of formula (V) may be optionally protected with a tri($C_{1-6}$ alkyl)silyl group, which consists of a silicon atom substituted with three $C_{1-6}$ alkyl groups, for example, trimethylsilyl, triethylsilyl, triisopropylsilyl, dimethylisopropylsilyl, diethylisopropylsilyl or t-butyldimethylsilyl, and a trimethylsilyl group is a preferred group.

The amount of the alcohol compound of formula (V) is in the range from 0.5 to 2 molar equivalents of the amount of the aldehyde compound of formula (IV), preferably from 0.9 to 1.2 molar equivalents.

The solvent used in Step A-2 is not particularly limited provided that it has no adverse effect on the reaction and that it dissolves the starting materials to some extent. Such solvents include aprotic solvents, for example, halogenated hydrocarbons such as dichloromethane, chloroform or 1,2-dichloroethane; aromatic hydrocarbons such as benzene, toluene or xylene; ethers such as diethyl ether or tetrahydrofuran; and the like. Preferred solvents include halogenated hydrocarbons or ethers, and dichloromethane or tetrahydrofuran is particularly preferred.

Examples of the acetalization reagent used in Step A-2 include inorganic acids such as hydrogen chloride, sulfuric acid or nitric acid; Lewis acids such as boron trifluoride, zinc chloride, magnesium bromide, titanium tetrachloride or aluminum chloride; sulfonic acids such as methanesulfonic acid, benzenesulfonic acid, p-toluenesulfonic acid, camphorsulfonic acid or trifluoromethanesulfonic acid; carboxylic acids such as formic acid, acetic acid, trifluoroacetic acid, oxalic acid or citric acid; and silylating reagents such as chlorotrimethylsilane or trimethylsilyl trifluoromethanesulfonate; preferably sulfonic acids; and most preferably p-toluenesulfonic acid.

The amount of the acetalization reagent is in the range from 1 to 3 molar equivalents of the amount of the alcohol compound of formula (V). When an aldehyde compound has a basic group, it is required to use an acid, the amount of which is an equal equivalent of the amount of said basic group.

The water produced during the reaction is removed by azeotropic distillation of the reaction solvent, by evaporation under reduced pressure, or by using a dehydrating reagent such as molecular sieves.

The reaction temperature of Step A-2 depends on various factors such as the acetalization reagent, the starting material and the solvent. It is usually between 0° C. and the boiling point of the reaction solvent, preferably between 5° C. and 40° C.

The reaction time of Step A-2 depends on various factors such as the acetalization reagent, the starting material, the solvent and the reaction temperature. It is usually from 0.5 to 24 hours, preferably from 1 to 5 hours.

After the reaction of Step A-2, the reaction mixture is neutralized with aqueous sodium bicarbonate solution or the like and then the desired compound of formula (I) is isolated from the reaction mixture according to conventional techniques. For example, the reaction mixture, or the residue obtained by concentration of the reaction mixture, is partitioned between water and an organic solvent immiscible with water, and the organic layer is then washed with water and then concentrated to afford the desired product.

The desired product (I) obtained thus, if necessary, can be further purified by conventional procedures such as recrystallization, reprecipitation or chromatography.

In addition, when the product of Step A-2 has a protecting group, said product can be converted to the desired compound (I) by removal of the protecting group.

The reaction conditions for the removal of the protecting group depend on the protecting group. The removal reaction can be carried out by conventional procedures known to those skilled in the art (see, "Protective Groups in Organic Synthesis", $2^{nd}$ Edition, Ed. by T. W. Greene & P. G. M. Wuts, 1991, John Wiley & Sons, Inc. or the like).

[Method B]

Method B is another process for preparation of compound (I) and is illustrated by the following reaction scheme.

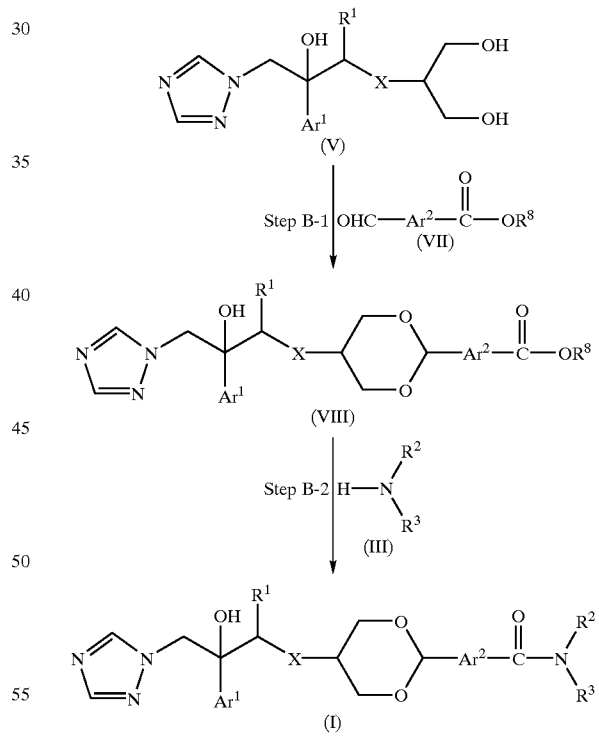

In the above reaction scheme, $Ar^1$, $Ar^2$, X, $R^1$, $R^2$ and $R^3$ have the same meanings as described above; and $R^8$ represents a $C_{1-6}$ alkyl group or a $C_{6-14}$ aryl group.

The "$C_{1-6}$ alkyl group" in the definition of $R^8$ includes a straight or branched chain alkyl group having 1 to 6 carbons, for example, a methyl, ethyl, propyl, isopropyl, butyl, isobutyl, s-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3- dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group, preferably a straight or branched chain alkyl group having 1 to 4 carbons.

The "$C_{6-14}$ aryl group" includes an aromatic hydrocarbon group having 6 to 14 carbons, for example a phenyl group, an indenyl group, a naphthyl group or an anthracenyl group, preferably a phenyl group.

Of these groups, $R^8$ is preferably a methyl group.

In Method B, reaction of the alcohol compound of formula (V) with the compound of formula (VII) in the presence of an acetalization reagent in an inert solvent, using a similar procedure to that described in Step A-2, where water produced during the reaction is removed from the reaction mixture to give the compound of formula (VIII) (Step B-1), is followed by reaction of the compound of formula (VIII) with the amine compound of formula (III) in the presence of an activating agent in an inert solvent to afford the compound of formula (I) (Step B-2).

Step B-1 is a process for preparation of the dioxane compound of formula (VIII) and is accomplished by the reaction of the alcohol compound of formula (V) with the aldehyde compound of formula (VII) in the presence of an acetalization reagent in an inert solvent, water produced during the reaction being removed from the reaction mixture during said reaction.

The aldehyde compound of formula (VII) is commercially available or can be prepared by techniques well known to those skilled in the art. The aldehyde compound of formula (VII) can, for example, be obtained by methyl esterification of a dicarboxylic acid compound ($Ar^2(CO_2H)_2$), reduction of one ester group of the esterified compound ($Ar^2(CO_2CH_3)_2$) with Red-Al or the like, followed by oxidation of the product with activated manganese dioxide.

This step can be accomplished using a similar procedure to that described in Step A-2.

Step B-2 can be accomplished by reaction of the compound of formula (VIII) with the amine compound of formula (III) in the presence of an activating reagent in an inert solvent.

The solvent used in Step B-2 is not particularly limited provided that it has no adverse effect on the reaction and that it dissolves the starting materials to some extent. Such solvents include aprotic solvents, for example, halogenated hydrocarbons such as dichloromethane, chloroform or 1,2-dichloroethane; aromatic hydrocarbons such as benzene, toluene or xylene; ethers such as diethyl ether or tetrahydrofuran; or mixtures thereof. Of these solvents, preferred solvents include aromatic hydrocarbons or halogenated hydrocarbons, and toluene is particularly preferred.

The activating reagent used in Step B-2 is not particularly limited provided that it can usually be used as a reagent for converting an ester to an amide in organic synthesis. Examples of such activating reagents include (lower alkyl) aluminiums such as trimethylaluminium or triethylaluminium; alkali metal cyanides such as sodium cyanide; hydroxy aromatic heterocyclic compounds containing one or more nitrogen atoms such as 2-hydroxypyridine; bases such as sodium methoxide or butyllithium; or halogenated borons such as boron tribromide. Of these activating agents, (lower alkyl)aluminiums are preferred and trimethylaluminium is particularly preferred.

The amount of the activating reagent used in Step B-2 is in the range from 1 to 5 molar equivalents of the amount of the ester compound of formula (VIII) and preferably from 1.5 to 3.0 molar equivalents.

The amount of the amine compound of formula (III) is in the range of from 0.5 to 5 molar equivalents of the amount of ester compound of formula (VIII), preferably from 0.9 to 2.5 molar equivalents.

The reaction temperature of Step B-2 depends on various factors such as the activating reagent, the starting material and the solvent. It is usually between room temperature and the boiling point of the reaction solvent, preferably between 50° C. and 90° C.

The reaction time of Step B-2 depends on various factors such as the activating reagent, the starting material, the solvent and the reaction temperature. It is usually from 0.5 to 24 hours, preferably from 1 to 5 hours.

After the reaction of Step B-2, to the reaction mixture is added aqueous sodium bicarbonate solution or the like in order to decompose the activating reagent, and then the desired compound (I) is isolated from the reaction mixture according to conventional techniques. For example, the reaction mixture, or the residue obtained by concentration of the reaction mixture, is partitioned between water and an organic solvent immiscible with water, and the organic layer is washed with water and then concentrated to afford the desired product.

The desired product of formula (I) thus obtained can, if necessary, be further purified by conventional procedures such as recrystallization, reprecipitation or chromatography.

In addition, when the product of Step B-2 has a protecting group, said product can be converted to the desired compound (I) by removal of the protecting group using a similar technique to that described in Method A.

Pharmaceutically acceptable prodrugs of compound (I) can be prepared by conventional techniques known to those skilled in the art. Of these pharmaceutically acceptable prodrugs, various acyl derivatives can be obtained by acylation of the hydroxyl group of compound (I) using conventional procedures.

The compound (I) or the pharmaceutically acceptable prodrug obtained above can be converted to a pharmaceutically acceptable salt by treating with an acid or a base in a solvent.

The solvents employed are not particularly limited and include, for example, aromatic hydrocarbons such as benzene; halogenated hydrocarbons such as dichloromethane or chloroform; ethers such as ether, tetrahydrofuran or dioxane; esters such as ethyl acetate; alcohols such as methanol or ethanol; ketones such as acetone; nitriles such as acetonitrile; hydrocarbons such as hexane or cyclohexane; or mixtures thereof.

The acids employed are not particularly limited provided that they are pharmaceutically acceptable acids. Examples of such acids include inorganic acids such as hydrochloric acid, hydrobromic acid, sulfuric acid or nitric acid; carboxylic acids such as acetic acid, fumaric acid, maleic acid, oxalic acid, malonic acid, succinic acid, citric acid or malic acid; sulfonic acids such as methanesulfonic acid, ethanesulfonic acid, benzenesulfonic acid or toluenesulfonic acid; or amino acids such as glutamic acid or aspartic acid.

The bases employed are not particularly limited provided that they are pharmaceutically acceptable bases. Examples of such bases include alkali metal (such as lithium, sodium or potassium) hydroxides or carbonates; alkaline earth metal (such as calcium or magnesium) hydroxides or carbonates; ammonia; organic amines such as triethylamine, diisopropylamine or cyclohexylamine.

The desired salt can usually be isolated from the solution of the compound (I) and the acid or the base as crystals or a powder, by adding a solvent which does not dissolve said salt to the solution containing said salt as a precipitate or by evaporation of the solvent of the solution containing said salt.

The compounds (I) and pharmaceutically acceptable salts thereof exhibit excellent antifungal activity against many eumycetes. Examples of eumycetes include Candida species, Aspergillus species, Cryptococcus species, Mucor species, Histoplasma species, Blastomyces species, Coccidioides species, Paracoccidioides species, Trichophyton species, Epidermophyton species, Microsporum species, Malassezia species, Psuedallescheria species, Sporothrix species, Rhinosporidium species, Fonsecaea species, Wangiella species, Phialophora species, Exophiala species, Cladosporium species, Alternaria species, Aureobasidium species, Chaetomium species, Curvularia species, Drechslera species, Mycocentrospora species, Phoma species, Hendersonula species, Scytalidium species, Corynespora species, Leptospheria species, Madurella species, Neotestudina species, Scedosporium species, Pyrenochaeta species, Geotrichum species, Trichosporon species, Chrysosporium species, Coprinus species, Schizophylum species, Pneumocystis species, Conidiobolus species, Basidiobolus species, Paecilomyces species, Penicillium species, Acremonium species, Fusarium species, Scopulariopsis species, Saccharomyces species, Cephalosporium species, Loboa species, Rhizopus species, Rhizomucor species or Absidia species.

The pharmaceutically acceptable prodrug of compound (I) produces the compound (I) or a salt thereof, which exhibits excellent antifungal activity, by a chemical or biological cleavage reaction (hydrolysis or the like) in the body of a human or animal. The compounds (I), pharmaceutically acceptable prodrugs thereof and pharmaceutically acceptable salts thereof can be used as a medicament, preferably as an antifungal agent. The compound (I), pharmaceutically acceptable prodrug thereof or salt thereof can be administered by itself or as a mixture of it with pharmaceutically acceptable carrier(s) including excipient(s), diluent(s), and the like in dosage forms such as tablets, capsules, granules, powders, syrups or the like for oral administration or in dosage forms such as injections or the like for parenteral administration and in ointments for topical administration.

The pharmaceutical formulations can be prepared in a known procedure using carriers such as excipients, binders, disintegrants, lubricants, stabilizers, corrigents, suspending agents, diluents, and solvents for formulation.

Examples of excipients include sugar derivatives such as lactose, sucrose, glucose, mannitol or sorbitol; starch derivatives such as corn starch, potato starch, α-starch, dextrin or carboxymethylstarch, cellulose derivatives such as crystalline cellulose, low-substituted hydroxypropylcellulose, hydroxypropylmethylcellulose, carboxymethylcellulose, internally cross-linked sodium carboxymethylcellulose; gum arabic; dextran; pullulan; silicate derivatives such as light silicic acid anhydride, synthetic aluminum silicate or magnesium aluminate metasilicate; phosphate derivatives such as calcium phosphate; carbonate derivatives such as calcium carbonate, sulfates such as calcium sulfate, and the like.

Examples of binders include excipients such as those described above; gelatin; polyvinylpyrrolidone; macrogol; and the like.

Examples of disintegrants include excipients such as those described above, chemically modified starch or cellulose derivatives such as sodium cross-carmellose, sodium carboxymethylstarch, cross-linked polyvinylpyrrolidone and the like.

Example of lubricants include talc; stearic acid; metal stearate derivatives such as calcium stearate or magnesium stearate; colloidal silica; veegum; waxes such as beeswax or spermaceti; boric acid; glycol; carboxylic acids such as fumaric acid or adipic acid; sodium carboxylates such as sodium benzoate; sulfates such as sodium sulfate; leucine; lauryl sulfates such as sodium lauryl sulfate or magnesium lauryl sulfate; silicic acid derivatives such as silicic acid anhydride or silicic acid hydrate; starch derivatives such as those described above in relation to excipients, and the like.

Examples of stabilizers include para-hydroxybenzoic acid ester derivatives such as methylparaben or propylparaben; alcohol derivatives such as chlorobutanol, benzyl alcohol or phenethyl alcohol; benzalkonium chloride; phenol derivatives such as phenol or cresol; thimerosal; acetic anhydride, sorbic acid and the like.

Examples of corrigents include sweeteners, souring agents, flavoring agents and the like commonly used for the purpose.

Examples of suspending agents include polysorbate 80, sodium carboxymethylcellulose and the like.

Examples of solvents for formulation include water, ethanol, glycerin and the like.

The dose of the compound (I), pharmaceutically acceptable prodrug thereof or pharmaceutically acceptable salt thereof will vary depending on a variety of factors such as the age, symptoms and the like of the patient. A suitable (i.e. effective) dosage level for oral administration is from 1 mg (preferably 5 mg) per day and per time as a lower limit to 2000 mg (preferably 1000 mg) per day and per time as an upper limit for an adult. A suitable dosage level for intravenous administration is from 0.1 mg (preferably 0.5 mg) per day per time as a lower limit to 600 mg (preferably 500 mg) per day and per time as an upper limit for an adult. The compound (I), pharmaceutically acceptable prodrug thereof or pharmaceutically acceptable salt thereof can be administered either a single unit dosage, or if desired, the dosage may be divided into convenient subunits administered from one to six times throughout the day depending on the symptoms of the patient, (human or animal).

The following Examples, Test Examples and Formulation Examples are intended to further illustrate the present invention and are not intended to limit the scope of the invention in any way.

Example 1

4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-4'-(2,2,3,3-tetrafluoropropoxy)benzanilide and cis isomer Thereof (Exemplification Compound Number 1-1)

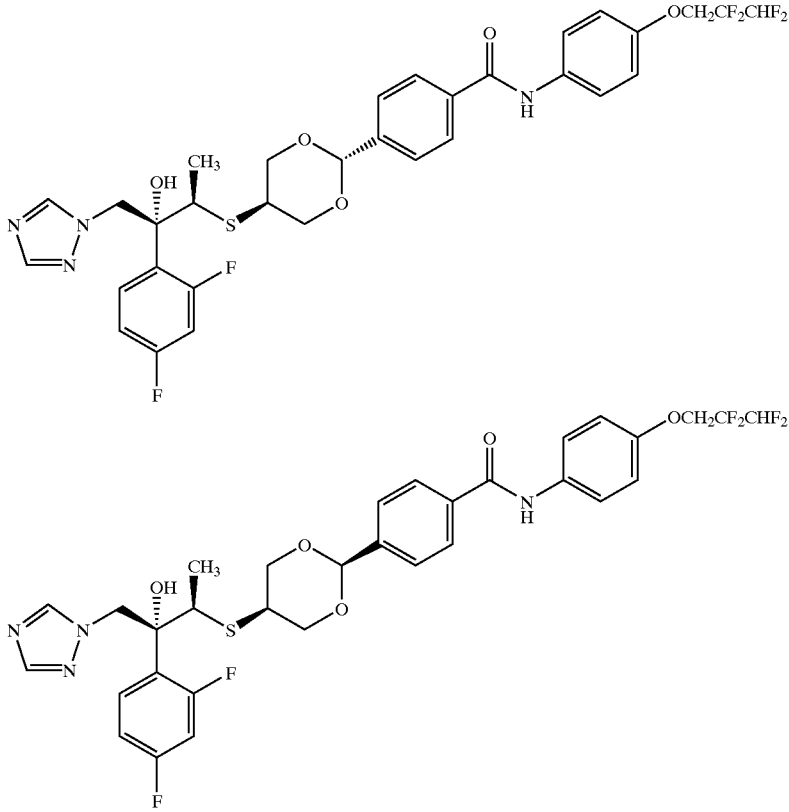

(1) Commercially available 4-formylbenzoic acid (5.0 g, 33.3 mmol) was dissolved in a mixture of anhydrous tetrahydrofuran (100 ml) and anhydrous N,N-dimethylformamide (1 ml) and the mixture was cooled with stirring to 0° C. To the resulting mixture was added dropwise oxalyl chloride (3.8 ml, 43.3 mmol). The mixture was stirred at room temperature for 30 minutes and then at 40° C. for 20 minutes. The reaction mixture was concentrated under reduced pressure and then in vacuo to afford 4-formylbenzoyl chloride. 4-(2,2,3,3-Tetrafluoropropoxy)aniline (646 mg, 2.9 mmol), described in Chem. Pharm. Bull., 44 (2), 314 (1996), and N,N-diisopropylethylamine (1.21 ml, 7.0 mmol) were dissolved in anhydrous tetrahydrofuran (8 ml) and the mixture was cooled to 0° C. with stirring. To the resulting mixture was added dropwise a solution of 4-formylbenzoyl chloride (561 mg, 3.33 mmol) obtained above in anhydrous tetrahydrofuran (2 ml). This mixture was stirred at room temperature for 17 hours and then at 40° C. for 20 minutes. At the end of this time, saturated aqueous sodium hydrogencarbonate solution was added to the reaction mixture in an ice bath and the mixture was partitioned between ethyl acetate and water. The organic layer was washed sequentially with 0.5N hydrochloric acid, saturated aqueous sodium hydrogencarbonate solution, water, and saturated aqueous sodium chloride solution, dried over anhydrous magnesium sulfate and concentrated under reduced pressure. The crystalline residue was recrystallized from a mixture of ethyl acetate and hexane to give 4-formyl-4'-(2,2,3,3-tetrafluoropropoxy)benzanilide (634 mg, yield 62%) as pale yellow crystals.

Melting point: 152° C. NMR spectrum (400 MHz, $CDCl_3$) δ ppm: 4.37 (2H, t, J=12 Hz), 6.07 (1H, tt, J=53, 5 Hz), 6.97 (2H, d, J=9 Hz), 7.61 (2H, d, J=9 Hz), 7.77 (1H, s), 8.03 (4H, s), 10.12 (1H, s). IR spectrum ν max (KBr) $cm^{-1}$: 3329, 1699, 1649, 1256, 1108. Mass spectrum m/z (EI): 355 ($M^+$), 133 (100%), 105.

(2) Molecular sieve 4A (3 g) was added to a mixture of 4-formyl-4'-(2,2,3,3-tetrafluoropropoxy)benzanilide (300 mg, 0.84 mmol) obtained in example 1 (1), (2R,3R)-2-(2,4-difluorophenyl)-3-[[1-(hydroxymethyl)-2-hydroxyethyl]thio]-1-(1H-1,2,4-triazol-1-yl)-2-butanol (disclosed in Japanese Patent Application Publication No. Hei-8-333350; 253 mg, 0.70 mmol), p-toluenesulfonic acid monohydrate (160 mg, 0.84 mmol) in anhydrous tetrahydrofuran (10 ml) and anhydrous dichloromethane (5 ml). The resulting mixture was stirred at room temperature for two days. Aqueous sodium hydrogencarbonate solution was added to the reaction mixture at 0° C., and the mixture was filtered to remove the molecular sieve. The filtrate was partitioned between ethyl acetate and water. The organic layer was washed with saturated aqueous sodium chloride solution, dried over anhydrous magnesium sulfate and then concentrated under reduced pressure. The resulting oily residue was chromatographed on a silica gel column using ethyl acetate-hexane (2:1) as the eluant to afford the trans isomer of the title compound (87 mg, yield 18%) as a white solid and then using ethyl acetate-hexane (4:1) as the eluant to give the cis isomer (55 mg, yield 11%) as a colorless oil. The trans isomer was recrystallized from ethyl acetate-isopropyl ether to give white powdery crystals.

Trans isomer: Melting point: 156° C. NMR spectrum (400 MHz, CDCl$_3$) δ ppm: 1.21 (3H, d, J=7 Hz), 3.36 (1H, q, J=7 Hz), 3.4–3.6 (1H, m), 3.76 (1H, t, J=11 Hz), 3.78 (1H, t, J=11 Hz), 4.36 (2H, t, J=12 Hz), 4.42 (1H, ddd, J=11, 5, 2 Hz), 4.55 (1H, ddd, J=11, 5, 2 Hz), 4.85 (1H, d, J=14 Hz), 5.05 (1H, d, J=1 Hz), 5.06 (1H, d, J=14 Hz), 5.54 (1H, s), 6.07 (1H, tt, J=53, 5 Hz), 6.7–6.8 (2H, m), 6.95 (2H, d, J=9 Hz), 7.3–7.4 (1H, m), 7.59 (2H, d, J=9 Hz), 7.62 (2H, d, J=9 Hz), 7.74 (1H, s), 7.80 (2H, s), 7.88 (2H, d, J=9 Hz) IR spectrum ν max (KBr) cm$^{-1}$: 3322, 1656, 1512, 1251, 1139. Mass spectrum m/z (FAB): 697 (M$^+$+1). Specific rotation: [α]$_D^{25}$ −59° (c=0.57, CHCl$_3$).

Cis isomer: NMR spectrum (400 MHz, CDCl$_3$) δ ppm: 1.23 (3H, d, J=7 Hz), 3.22 (1H, t, J=2 Hz), 3.44 (1H, q, J=7 Hz), 4.2–4.5 (4H, m), 4.35 (2H, t, J=12 Hz), 4.87 (1H, d, J=14 Hz), 4.97 (1H, s), 5.15 (1H, d, J=14 Hz), 5.66 (1H, s), 6.07 (1H, tt, J=53, 5 Hz), 6.7–6.8 (2H, m), 6.95 (2H, d, J=8 Hz), 7.3–7.5 (1H, m), 7.59 (2H, d, J=8 Hz), 7.64 (2H, d, J=8 Hz), 7.77 (1H, s), 7.78 (1H, s), 7.79 (1H, s), 7.88 (2H, d, J=8 Hz). Mass spectrum m/z (FAB): 697 (M$^+$+1)

Example 2

4'-Cyano-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide and cis isomer Thereof (Exemplification Compound Number 2-1)

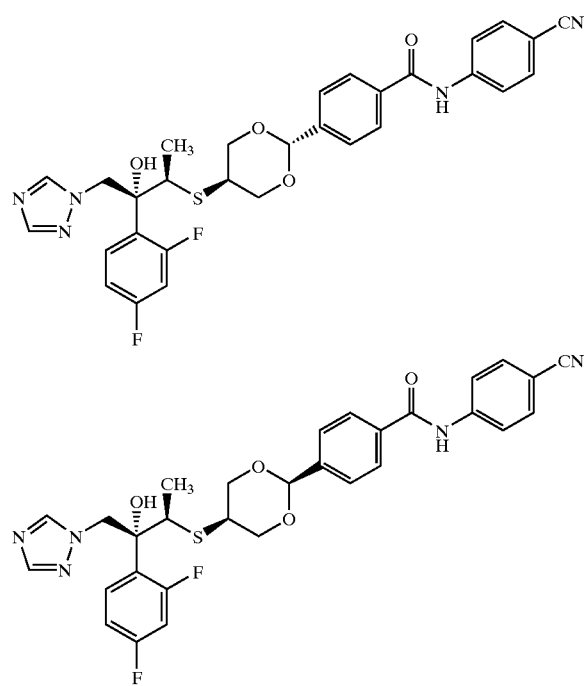

(1) In the same manner as that described in Example 1(1), a reaction was carried out using commercially available 4-aminobenzonitrile (343 mg, 2.9 mmol), N,N-diisopropylethylamine (1.21 ml, 7.0 mmol), 4-formylbenzoyl chloride (561 mg, 3.33 mmol) and 4-(dimethylamino)pyridine (a catalytic amount) and the reaction mixture was treated according to a similar procedure to that described in Example 1(1) to afford an oily residue. The residue was chromatographed on a silica gel column using ethyl acetate-hexane (2:1) as the eluant to obtain 4'-cyano-4-formylbenzanilide (81 mg, yield 11%) as a pale yellow solid which was recrystallized from ethyl acetate to give pale yellow powdery crystals.

Melting point: 236° C. NMR spectrum (270 MHz, DMSO-d$_6$) δ ppm: 7.85 (2H, d, J=8 Hz), 8.00 (2H, d, J=8 Hz), 8.08 (2H, d, J=8 Hz), 8.15 (2H, d, J=8 Hz), 10.13 (1H, s), 10.85 (1H, s). IR spectrum ν max (Knr) cm$^{-1}$: 3368, 2223, 1685, 1518. Mass spectrum m/z (EI): 250 (M$^+$), 133 (100%), 105.

(2) In the same manner as that described in Example 1(2), a reaction was carried out using 4'-cyano-4-formylbenzanilide (75 mg, 0.30 mmol) obtained in Example 2(1), (2R,3R)-2-(2,4-difluorophenyl)-3-[[1-(hydroxymethyl)-2-hydroxyethyl]thio]-1-(1H-1,2,4-triazol-1-yl)butanol (98 mg, 0.27 mmol) and p-toluenesulfonic acid monohydrate (62 mg, 0.32 mmol) and the reaction mixture was treated using a similar procedure to that described in Example 1(2) to give the trans isomer of the title compound (30 mg, yield 19%) as a white solid and the cis isomer (20 mg, yield 12%) as a white solid. The trans isomer was recrystallized from ethyl acetate-hexane to give white powdery crystals.

Trans isomer: Melting point: 176° C. NMR spectrum (270 MHz, CDCl$_3$) δ ppm: 1.22 (3H, d, J=7 Hz), 3.36 (1H, q, J=7 Hz), 3.4–3.6 (1H, m), 3.76 (1H, t, J=11 Hz), 3.79 (1H, t, J=11 Hz), 4.42 (1H, ddd, J=11, 5, 2 Hz), 4.55 (1H, ddd, J=11, 5, 2 Hz), 4.85 (1H, d, J=14 Hz), 5.05 (1H, d, J=1 Hz), 5.05 (1H, d, J=14 Hz), 5.55 (1H, s), 6.7–6.8 (2H, m), 7.3–7.4 (1H, m), 7.65 (2H, d, J=8 Hz), 7.68 (2H, d, J=8 Hz), 7.80 (2H, s), 7.80 (2H, d, J=8 Hz), 7.89 (2H, d, J=8 Hz), 7.93 (1H, s). IR spectrum ν max (KBr) cm$^{-1}$: 3371, 2225, 1679, 1512, 1319, 1139. Mass spectrum m/z (FAB): 592 (M$^+$+1) Specific rotation: [α]$_D^{25}$−52° (c=0.60, AcOEt).

Cis isomer: NMR spectrum (270 MHz, CDCl$_3$) δ ppm: 1.23 (3H, d, J=7 Hz) 3.22 (1H, t, J=2 Hz), 3.44 (1H, q, J=7 Hz), 4.2–4.5 (4H, m), 4.86 (1H, d, J=14 Hz), 4.97 (1H, s), 5.15 (1H, d, J=14 Hz), 5.67 (1H, s), 6.6–6.8 (2H, m), 7.3–7.5 (1H, m), 7.67 (2H, d, J=8 Hz), 7.67 (2H, d, J=8 Hz), 7.78 (1H, s), 7.79 (1H, s), 7.80 (2H, d, J=8 Hz), 7.88 (2H, d, J=8 Hz), 8.02 (1H, bs). Mass spectrum m/z (FAB): 592 (M$^+$+1)

Example 3

4'-Cyano-6-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-2-naphthoanilide (Exemplification Compound Number 2-2)

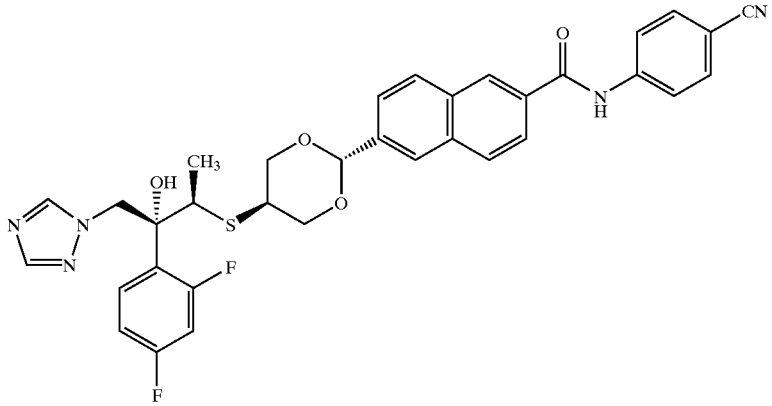

(1) Red-Al (0.61 ml of a 65% toluene solution, a product of Aldrich, 2.1 mmol) was added dropwise to a solution of commercially available dimethyl 2,6-naphthalenedicarboxylate (500 mg, 2.1 mmol) in anhydrous tetrahydrofuran (120 ml) cooled to −50° C. The resulting mixture was stirred at −50° C. for 1 hour and then at room temperature for 1.5 hours. To the reaction mixture were added sequentially ethyl acetate, water, 0.5N aqueous sodium potassium (+)-tartrate solution and the mixture was partitioned between ethyl acetate and water. The organic layer was washed with saturated aqueous sodium chloride solution, dried over anhydrous magnesium sulfate and then concentrated under reduced pressure. The resulting residue was chromatographed on a silica gel column using ethyl acetate-hexane (2:1) as the eluant to obtain methyl 6-hydroxymethyl-2-naphthalenecarboxylate (288 mg, yield 65%) as a white solid which was recrystallized from ethyl acetate-hexane to give white powdery crystals.

Melting point: 122° C. NMR spectrum (400 MHz, CDCl$_3$) δ ppm: 1.80 (1H, t, J=6 Hz), 3.99 (3H, s), 4.90 (2H, d, J=6 Hz), 7.55 (1H, d, J=9 Hz), 7.8–7.9 (2H, m), 7.96 (1H, d, J=9 Hz), 8.07 (1H, d, J=9 Hz), 8.61 (1H, s). IR spectrum ν max (KBr) cm$^{-1}$: 3252, 1716. Mass spectrum m/z (EI): 216 (M$^+$, 100%).

| Elemental analysis: | | | |
|---|---|---|---|
| Calculated for C$_{13}$H$_{12}$O$_3$ | C: 72.21 | H: 5.59 | N: 0.00 |
| Found | C: 72.11 | H: 5.39 | N: 0.00 |

(2) Activated manganese dioxide (2.1 g) was added to a solution of methyl 6-hydroxymethyl-2-naphthalenecarboxylate (266 mg, 1.23 mmol) obtained in example 3 (1) in dichloromethane (30 ml). The resulting mixture was stirred at room temperature for 1.5 hours. At the end of this time the reaction mixture was chromatographed on a silica gel column using ethyl acetate-hexane (1:2) as the eluant to obtain methyl 6-formyl-2-naphthalenecarboxylate (237 mg, yield 90%) as a white solid which was recrystallized from ethyl acetate-hexane to give white fluffy crystals.

Melting point: 127° C. NMR spectrum (400 MHz, CDCl$_3$) δ ppm: 3.97 (3H, s), 7.98 (1H, dd, J=8, 1 Hz), 8.0–8.1 (2H, m), 8.13 (1H, dd, J=8, 1 Hz), 8.34 (1H, s), 8.62 (1H, s), 10.16 (1H, s). IR spectrum ν max (KBr) cm$^{-1}$: 1718, 1696, 1682. Mass spectrum m/z (EI): 214 (M$^+$), 183 (100%)

| Elemental analysis: | | | |
|---|---|---|---|
| Calculated for C$_{13}$H$_{10}$O$_3$ | C: 72.89 | H: 4.71 | N: 0.00 |
| Found | C: 72.60 | H: 4.53 | N: 0.00 |

(3) A solution of methyl 6-formyl-2-naphthalenecarboxylate (227 mg, 1.06 mmol) obtained in example 3 (2), (2R,3R)-2-(2,4-difluorophenyl)-3-[[1-(hydroxymethyl)-2-hydroxyethyl]thio]-1-(1H-1,2,4-triazol-1-yl)-2-butanol (381 mg, 1.06 mmol) and p-toluenesulfonic acid monohydrate (363 mg, 1.91 mmol) in anhydrous tetrahydrofuran (50 ml) was concentrated at room temperature using a rotary evaporator under reduced pressure and then using a vacuum pump. A solution of the residue in anhydrous tetrahydrofuran (40 ml) was concentrated according to the procedure described above. The same procedure was repeated twice. A solution of the resulting residue in tetrahydrofuran (50 ml) was poured into a saturated aqueous sodium hydrogencarbonate solution cooled to 0° C. with stirring. The mixture was extracted with ethyl acetate and the organic layer was washed with aqueous sodium chloride solution, dried over anhydrous magnesium sulfate and then concentrated under reduced pressure. The oily residue was chromatographed on a silica gel column using ethyl acetate-hexane (1:2) as the eluant to afford methyl 6-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-2-naphthalenecarboxylate (trans isomer, 331 mg, yield 56%) as a white solid, and then using ethyl acetate-hexane (3:1) as the eluant to afford methyl 6-[cis-5-[[(1R,2R)-2-(2,4-difluorophenyl)-2-hydroxy-1-methyl-3-(1H-1,2,4-triazol-1-yl)propyl]thio]-1,3-dioxan-2-yl]-2-naphthalenecarboxylate (cis isomer, 77 mg, yield 14%) as a colorless oil. The trans isomer was recrystallized from ethyl acetate-hexane to give white fluffy crystals.

trans isomer: Melting point: 153° C. NMR spectrum (400 MHz, CDCl₃) δ ppm: 1.22 (3H, d, J=7 Hz), 3.37 (1H, q, J=7 Hz), 3.5–3.6 (1H, m), 3.81 (1H, t, J=11 Hz), 3.83 (1H, t, J=11 Hz), 3.99 (3H, s), 4.46 (1H, ddd, J=11, 5, 2 Hz), 4.58 (1H, ddd, J=11, 5, 2 Hz), 4.86 (1H, d, J=14 Hz), 5.05 (1H, s), 5.06 (1H, d, J=14 Hz), 5.66 (1H, s), 6.7–6.8 (2H, m) 7.3–7.4 (1H, m), 7.66 (1H, d, J=9 Hz), 7.80 (2H, s), 7.91 (1H, d, J=9 Hz), 7.98 (1H, d, J=9 Hz), 8.01 (1H, s), 8.07 (1H, dd, J=9, 1 Hz), 8.61 (1H, s). IR spectrum ν max (KBr) cm⁻¹: 3445, 1718, 1708, 1139. Mass spectrum m/z (FAB): 556 (M⁺+1). .

| Elemental analysis: | | | | |
|---|---|---|---|---|
| Calculated for C₂₈H₂₇F₂N₃O₅S | C: 60.53 | H: 4.90 | N: 7.56 | F: 6.84 |
| Found | C: 60.52 | H: 4.86 | N: 7.56 | F: 6.87. | cis isomer NMR spectrum (400 MHz, CDCl₃) δ ppm: 1.24 (3H, d, J=7 Hz), 3.23 (1H, t, J=2 Hz), 3.4–3.6 (1H, m), 3.99 (3H, s), 4.2–4.5 (4H, m), 4.88 (1H, d, J=14 Hz), 4.97 (1H, d, J=1 Hz), 5.17 (1H, d, J=14 Hz), 5.78 (1H, s), 6.6–6.8 (2H, m), 7.3–7.5 (1H, m), 7.71 (1H, dd, J=9, 1 Hz), 7.77 (1H, s), 7.79 (1H, s), 7.91 (1H, d, J=8 Hz), 7.98 (1H, d, J=8 Hz), 8.03 (1H, s), 8.07 (1H, dd, J=9, 1 Hz), 8.61 (1H, s). Mass spectrum m/z (FAB): 556 (M⁺+1).

(4) Trimethylaluminium (0.67 ml, 1.07M n-hexane solution, 0.72 mmol) was added dropwise to a solution of commercially available 4-aminobenzonitrile (85 mg, 0.72 mmol) in anhydrous toluene (4 ml) at room temperature with stirring under a nitrogen atmosphere. After stirring the mixture at room temperature for 10 minutes, a solution of methyl 6-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-2-naphthalenecarboxylate (100 mg, 0.18 mmol) in anhydrous toluene (3 ml) was added dropwise to the resulting mixture. This mixture was stirred at 80C for 2.5 hours. At the end of this time to the reaction mixture were added sequentially water and 0.5N aqueous potassium sodium (+)-tartrate solution at room temperature. The mixture was partitioned between ethyl acetate and water. The organic layer was washed with saturated aqueous sodium chloride solution, dried over anhydrous magnesium sulfate and concentrated under reduced pressure. The resulting residue was chromatographed on a silica gel column using ethyl acetate-hexane (3:1) as the eluant to afford the title compound (99 mg, yield 85%) as a colorless oil which was recrystallized from ethyl acetate-hexane to give white powdery crystals.

Melting point: 114° C. NMR spectrum (400 MHz, CDCl₃) δ ppm: 1.23 (3H, d, J=7 Hz), 3.38 (1H, q, J=7 Hz), 3.5–3.6 (1H, m), 3.82 (1H, t, J=11 Hz), 3.84 (1H, t, J=11 Hz), 4.46 (1H, ddd, J=11, 5, 2 Hz), 4.59 (1H, ddd, J=11, 5, 2 Hz), 4.86 (1H, d, J=14 Hz), 5.06 (1H, d, J=1 Hz), 5.06 (1H, d, J=14 Hz), 5.68 (1H, s), 6.7–6.8 (2H, m), 7.3–7.5 (1H, m), 7.69 (2H, d, J=9 Hz), 7.70 (1H, d, J=9 Hz), 7.80 (2H, s), 7.85 (2H, d, J=9 Hz), 7.92 (1H, dd, J=9, 1 Hz), 8.00 (2H, d, J=9 Hz), 8.06 (1H, s), 8.12 (1H, s), 8.39 (1H, s). IR spectrum ν max (KBr) cm⁻¹: 3395, 2225, 1681, 1513, 1138. Mass spectrum m/z (FAB): 642 (M⁺+1). Specific rotation: [α]_D^25 −61° (c=0.60, CHCl₃).

Example 4

4'-Cyano-4-[trans-5-[(2S,3R)-3-(2,4-difluorophenyl)-3-hydroxy-2-methyl-4-(1H-1,2,4-triazol-1-yl)butyl]-1,3-dioxan-2-yl]benzanilide and cis isomer Thereof (Exemplification Compound Number 2-3)

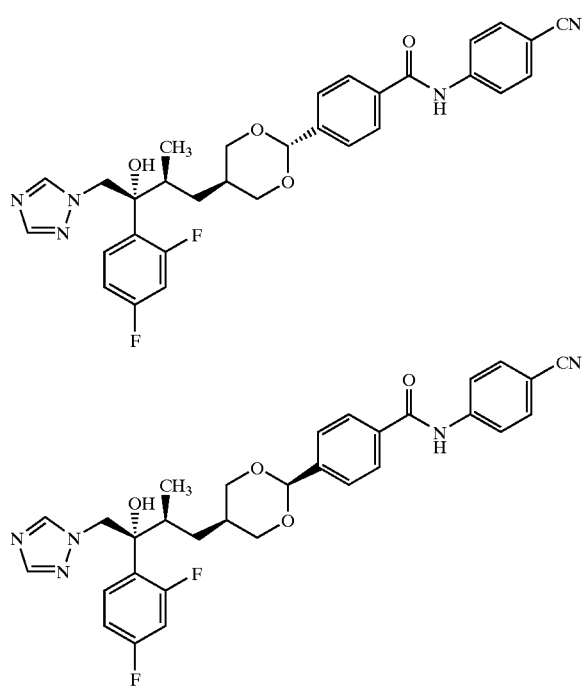

In the same manner as described in Example 1(2), a reaction was carried out using 4'-cyano-4-formylbenzanilide (78 mg, 0.31 mmol) obtained in Example 2(1), (4S,5R)-5-(2,4-difluorophenyl)-2-(hydroxymethyl)-4-methyl-6-(1H-1,2,4-triazol-1-yl)-1,5-hexanediol (disclosed in Japanese Patent Application Publication No. Hei-11-80135: 100 mg, 0.29 mmol) and p-toluenesulfonic acid monohydrate (99 mg, 0.52 mmol) and the reaction mixture was treated using a similar procedure to that described in Example 1(2) to give the trans isomer of the title compound (100 mg, yield 59%) as a white solid and the cis isomer (23 mg, yield 14%) as a colorless oil. The trans isomer was recrystallized from ethyl acetate-hexane to give white powdery crystals.

Trans isomer: Melting point 159° C. NMR spectrum (500 MHz, CDCl₃) δ ppm: 0.86 (3H, d, J=7 Hz), 1.15 (1H, ddd, J=14, 10, 2 Hz), 1.49 (1H, ddd, J=14, 10, 2 Hz), 2.0–2.1 (1H, m), 2.2–2.3 (1H, m), 3.60 (1H, t, J=11 Hz), 3.62 (1H, t, J=11 Hz), 4.23 (1H, ddd, J=11, 5, 2 Hz), 4.35 (1H, ddd, J=11, 5, 2 Hz), 4.50 (1H, d, J=14 Hz), 4.90 (1H, s), 4.96 (1H, d, J=14 Hz), 5.51 (1H, s), 6.6–6.8 (2H, m), 7.3–7.5 (1H, m), 7.64 (2H, d, J=8 Hz), 7.67 (2H, d, J=8 Hz), 7.79 (1H, s), 7.79 (2H, d, J=8 Hz), 7.87 (1H, s), 7.88 (2H, d, J=8 Hz), 7.94 (1H, bs). IR spectrum ν max (KBr) cm⁻¹: 3426, 2225, 1681, 1513, 1138. Mass spectrum m/z (FAB): 574 (M⁺+1). Specific rotation: [α]_D^25 −60° (c=0.56, CHCl₃).

Cis isomer: NMR spectrum (400 MHz, CDCl₃) δ ppm: 0.78 (3H, d, J=7 Hz), 1.5–1.8 (2H, m), 2.1–2.3 (1H, m), 2.5–2.6 (1H, m), 4.0–4.3 (4H, m), 4.65 (1H, d, J=14 Hz), 4.76 (1H, s), 4.91 (1H, d, J=14 Hz), 5.60 (1H, s), 6.6–6.8 (2H, m), 7.3–7.5 (1H, m), 7.61 (2H, d, J=8 Hz), 7.64 (2H, d, J=8 Hz), 7.76 (1H, s), 7.78 (1H, s), 7.81 (2H, d, J=8 Hz), 7.88 (2H, d, J=8 Hz), 8.18 (1H, bs). Mass spectrum m/z (FAB): 574 (M⁺+1).

Example 5

4'-Cyano-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-3-fluorobenzanilide (Exemplification Compound Number 2-21)

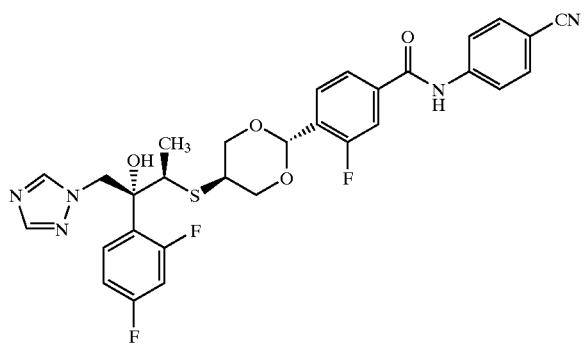

(1) Methyl 3-fluoro-4-bromomethylbenzoate (80 mg, 0.32 mmol), described in J. Med. Chem., 35(5) 877 (1992), was dissolved in a mixture of anhydrous dimethyl sulfoxide (4.5 ml) and anhydrous dichloromethane (3 ml). To the solution cooled to 0° C. was added dropwise with stirring triethylamine N-oxide dihydrate (180 mg, 1.62 mmol) and the mixture was stirred at room temperature for 2 hours. Water was added to the reaction mixture and this mixture was partitioned between a mixture of ethyl acetate and hexane (1:1) and water. The organic layer was washed with saturated aqueous sodium chloride solution, dried over anhydrous magnesium sulfate and then concentrated under reduced pressure. The residue was chromatographed on a silica gel column using ethyl acetate-hexane (1:10) as the eluant to give methyl 3-fluoro-4-formylbenzoate (29 mg, yield 48%) as a white solid. NMR spectrum (400 MHz, CDCl$_3$) δ ppm: 3.97 (3H, s), 7.85 (1H, d, J=11 Hz), 7.9–8.0 (2H, m), 10.43 (1H, s). Mass spectrum m/z (EI): 182 (M$^+$, 100%).

(2) In the same manner as that described in Example 3(3), a reaction was carried out using methyl 3-fluoro-4-formylbenzoate (105 mg, 0.58 mmol) obtained in Example 5(1), (2R,3R)-2-(2,4-difluorophenyl)-3-[[1-(hydroxymethyl)-2-hydroxyethyl]thio]-1-(1H-1,2,4-triazol-1-yl)-2-butanol (207 mg, 0.58 mmol) and p-toluenesulfonic acid monohydrate (199 mg, 1.04 mmol) and the reaction mixture was treated according to a similar procedure to that described in Example 3(3) to give methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-3-fluorobenzoate (trans isomer, 106 mg, yield 35%) and methyl 4-[cis-5-[[(1R,2R)-2-(2,4-difluorophenyl)-2-hydroxy-1-methyl-3-(1H-1,2,4-triazol-1-yl)propyl]thio]-1,3-dioxan-2-yl]-3-fluorobenzoate (cis isomer, 29 mg, yield 10%) as a colorless oil.

Trans isomer: NMR spectrum (400 MHz, CDCl$_3$) δ ppm: 1.21 (3H, d, J=7 Hz), 3.35 (1H, q, J=7 Hz), 3.4–3.6 (1H, m), 3.77 (1H, t, J=11 Hz), 3.79 (1H, t, J=11 Hz), 3.93 (3H, s), 4.39 (1H, ddd, J=11, 5, 2 Hz), 4.52 (1H, ddd, J=11, 5, 2 Hz), 4.84 (1H, d, J=14 Hz), 5.06 (1H, d, J=1 Hz), 5.05 (1H, d, J=14 Hz), 5.79 (1H, s), 6.7–6.8 (2H, m), 7.3–7.4 (1H, m), 7.6–7.8 (2H, m), 7.80 (2H, s), 7.86 (1H, dd, J=8, 1 Hz). Mass spectrum m/z (FAB): 524 (M$^+$+1).

| High resolution mass spectrum: | | |
|---|---|---|
| Calculated for C$_{24}$H$_{25}$O$_5$N$_3$F$_3$S | m/z | 524.1467 |
| Found | | 524.1457 |

Cis isomer: NMR spectrum (400 MHz, CDCl$_3$) δ ppm: 1.18 (3H, d, J=7 Hz), 3.1–3.2 (1H, m), 3.40 (1H, q, J=7 Hz), 3.87 (3H, s), 4.2–4.5 (4H, m), 4.83 (1H, d, J=14 Hz), 4.95 (1H, d, J=1 Hz), 5.12 (1H, d, J=14 Hz), 5.84 (1H, s), 6.6–6.8 (2H, m), 7.2–7.4 (1H, m), 7.66 (1H, dd, J=11, 1 Hz), 7.7–7.8 (1H, m), 7.73 (1H, s), 7.76 (1H, s), 7.81 (1H, dd, J=8, 1 Hz) Mass spectrum m/z (FAB): 524 (M$^+$+1).

(3) In the same manner as that described in Example 3(4) a reaction was carried out using commercially available 4-aminobenzonitrile (98 mg, 0.83,mmol), trimethylaluminium (0.78 ml, 1.07M n-hexane solution, 0.83 mmol) and methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-3-fluorobenzoate (109 mg, 0.21 mmol) obtained in Example 5(2) and the reaction mixture was treated using a similar procedure to that described in Example 3(4) to give the title compound (95 mg, yield 75%) as a colorless oil which was recrystallized from ethyl acetate-hexane to give white powdery crystals.

Melting point: 110° C. NMR spectrum (400 MHz, CDCl$_3$) δ ppm: 1.22 (3H, d, J=7 Hz), 3.36 (1H, q, J=7 Hz), 3.5–3.6 (1H, m), 3.78 (1H, t, J=11 Hz), 3.80 (1H, t, J=11 Hz), 4.41 (1H, ddd, J=11, 5, 2 Hz), 4.54 (1H, ddd, J=11, 5, 2 Hz), 4.85 (1H, d, J=14 Hz), 5.05 (1H, d, J=14 Hz), 5.07 (1H, s), 5.80 (1H, s), 6.7–6.8 (2H, m), 7.3–7.4 (1H, m), 7.6–7.7 (2H, m), 7.68 (2H, d, J=9 Hz), 7.7–7.8 (3H, m), 7.80 (2H, s), 7.96 (1H, bs). IR spectrum ν max (KBr) cm$^{-1}$: 3343, 2226, 1685, 1512, 1141. Mass spectrum m/z (FAB): 610 (M$^+$+1).

| High resolution mass spectrum (FAB): | | |
|---|---|---|
| Calculated for C$_{30}$H$_{27}$O$_4$N$_5$F$_3$S | m/z | 610.1736 |
| Found | | 610.1750. |

Specific rotation: [α]$_D^{25}$ −65° (c=0.53, CHCl$_3$).

Example 6

4'-Cyano-3-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide (Exemplification Compound Number 2-25)

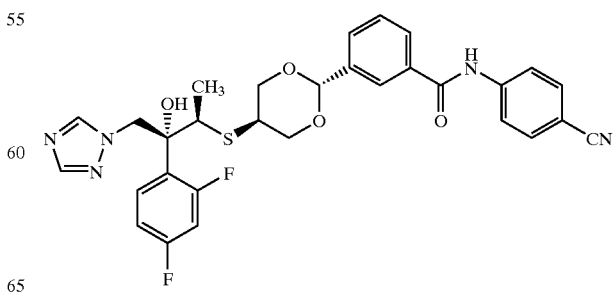

(1) In the same manner as that described in Example 3(3) a reaction was carried out using methyl 3-formylbenzoate, described in Chem. Ber., 45, 1585 (1912), (188 mg, 1.2 mmol), (2R, 3R)-2-(2,4-difluorophenyl)-3-[[1-(hydroxymethyl)-2-hydroxyethyl]thio]-1-(1H-1,2,4-triazol-1-yl)-2-butanol (412 mg, 1.2 mmol) and p-toluenesulfonic acid monohydrate (394 mg, 2.1 mmol) and the reaction mixture was treated according to a similar procedure to that described in Example 3(3) to give methyl 3-[trans-5-[[(1R, 2R)-2-(2,4-difluorophenyl)-2-hydroxy-1-methyl-3-(1H-1,2, 4-triazol-1-yl)propyl]thio]-1,3-dioxan-2-yl]-3-benzoate (228 mg, yield 39%) as a colorless oil.

NMR spectrum (400 MHz, CDCl$_3$) δ ppm: 1.21 (3H, d, J=7 Hz), 3.34 (1H, q, J=7 Hz), 3.4–3.6 (1H, m), 3.75 (1H, t, J=11 Hz), 3.78 (1H, t, J=11 Hz), 3.93 (3H, s), 4.41 (1H, ddd, J=11, 4, 2 Hz), 4.53 (1H, ddd, J=11, 4, 2 Hz), 4.85 (1H, d, J=14 Hz), 5.06 (1H, d, J=14 Hz), 5.07 (1H, s), 5.52 (1H, s), 6.7–6.8 (2H, m), 7.2–7.4 (1H, m), 7.47 (1H, t, J=8 Hz), 7.69 (1H, d, J=8 Hz), 7.79 (2H, s), 8.04 (1H, d, J=8 Hz), 8.18 (1H, s). Mass spectrum m/z (FAB): 506 (M$^+$+1).

(2) In the same manner as that described in Example 3(4) a reaction was carried out using commercially available 4-aminobenzonitrile (138 mg, 1.2 mmol), trimethylaluminium (1.08 ml, 1.07M n-hexane solution, 1.2 mmol) and methyl 3-[trans-5-[[(1R, 2R)-2-(2,4-difluorophenyl)-2-hydroxy-1-methyl-3-(1H-1,2,4-triazol-1-yl)propyl]thio]-1, 3-dioxan-2-yl]benzoate (147 mg, 0.29 mmol), obtained in Example 6(1), and the reaction mixture was treated using a similar procedure to that described in Example 3(4) to afford the title compound (162 mg, yield 94%) as a pale yellow oil which was recrystallized from ethyl acetate-hexane to give pale yellow powdery crystals.

Melting point: 105° C. NMR spectrum (400 MHz, CDCl$_3$) δ ppm: 1.22 (3H, d, J=7 Hz), 3.36 (1H, q, J=7 Hz), 3.4–3.6 (1H, m), 3.77 (1H, t, J=11 Hz), 3.80 (1H, t, J=11 Hz), 4.42 (1H, ddd, J=11, 4, 2 Hz), 4.56 (1H, ddd, J=11, 4, 2 Hz), 4.85 (1H, d, J=14 Hz), 5.06 (1H, d, J=14 Hz), 5.08 (1H, s), 5.56 (1H, s), 6.7–6.8 (2H, m), 7.3–7.4 (1H, m), 7.56 (1H, t, J=8 Hz), 7.68 (2H, d, J=8 Hz), 7.71 (1H, d, J=8 Hz), 7.80 (2H, s), 7.81 (2H, d, J=8 Hz), 7.92 (1H, d, J=8 Hz), 7.98 (1H, s), 8.00 (1H, bs). IR spectrum ν max (KBr) cm$^{-1}$: 3331, 2225, 1681, 1514, 1139. Mass spectrum m/z (FAB): 592 (M$^+$+1). Specific rotation: [α]$_D^{25}$ −64° (c=0.56, CHCl$_3$).

Example 7

4'-(Cyanomethyl)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide and cis isomer Thereof (Exemplification Compound Number 3-1)

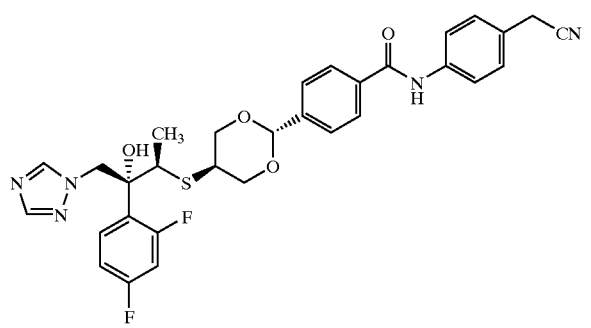

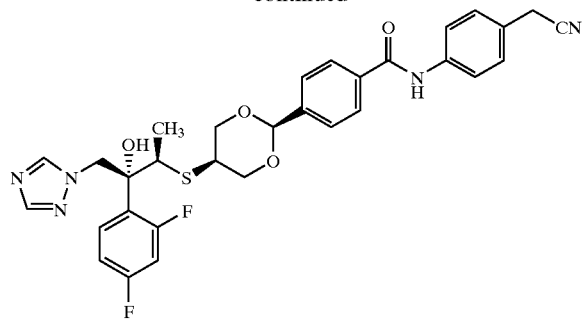

(1) In the same manner as that described in Example 2(1), a reaction was carried out using commercially available 4-aminobenzyl cyanide (329 mg, 2.5 mmol), N,N-diisopropylethylamine (0.91 ml, 5.2 mmol), 4-formylbenzoyl chloride (350 mg, 2.1 mmol) and 4-(dimethylamino)pyridine (a catalytic amount) and the reaction mixture was treated according to a similar procedure to that described in Example 2(1) to afford 4'-(cyanomethyl)-4-formylbenzanilide (370 mg, yield 67%) as a pale yellow solid which was recrystallized from a mixture of ethyl acetate and tetrahydrofuran to give pale yellow powdery crystals.

Melting point: 194° C. NMR spectrum (270 MHz, CDCl$_3$) δ ppm: 3.77 (2H, s), 7.37 (2H, d, J=8 Hz), 7.69 (2H, d, J=8 Hz), 7.84 (1H, bs), 8.02 (2H, d, J=8 Hz), 8.04 (2H, d, J=8 Hz), 10.13 (1H, s). IR spectrum ν max (KBr) cm$^{-1}$: 3343, 2253, 1699, 1666, 1597, 1526. Mass spectrum m/z (FAB): 265 (M$^+$+1).

(2) In the same manner as that described in Example 1(2) a reaction was carried out using 4'-(cyanomethyl)-4-formylbenzanilide (160 mg, 0.61 mmol), obtained in Example 7(1), (2R,3R)-2-(2,4-difluorophenyl)-3-[[1-(hydroxymethyl)-2-hydroxyethyl]thio]-1-(1H-1,2,4-triazol-1-yl)-2-butanol (189 mg, 0.53 mmol) and p-toluenesulfonic acid monohydrate (181 mg, 0.96 mmol) and the reaction mixture was treated using a similar procedure to that described in Example 1(2) to afford the trans isomer of the title compound (61 mg, yield 19%) as a pale yellow solid and the cis isomer (35 mg, yield 11%) as a white solid. The trans isomer was recrystallized from ethyl acetate-tetrahydrofuran to give white powdery crystals and the cis isomer was recrystallized from ethyl acetate-hexane to give pale yellow powdery cryatals.

Trans isomer: Melting point: 188° C. NMR spectrum (270 MHz, CDCl$_3$) δ ppm: 1.22 (3H, d, J=7 Hz), 3.36 (1H, q, J=7 Hz), 3.4–3.6 (1H, m), 3.7–3.9 (2H, m), 3.76 (2H, s), 4.42 (1H, ddd, J=11, 5, 2 Hz), 4.55 (1H, ddd, J=11, 5, 2 Hz), 4.85 (1H, d, J=14 Hz), 5.05 (1H, s), 5.05 (1H, d, J=14 Hz), 5.54 (1H, s), 6.7–6.8 (2H, m), 7.3–7.4 (1H, m), 7.35 (2H, d, J=8 Hz), 7.63 (2H, d, J=8 Hz), 7.80 (3H, bs), 7.68 (2H, d, J=8 Hz), 7.89 (2H, d, J=8 Hz). IR spectrum ν max (KBr) cm$^{-1}$: 3372, 2250, 1663, 1517, 1139. Mass spectrum m/z (FAB): 606 (M$^+$+1). Specific rotation: [α]$_D^{25}$ −680 (c=0.51, CHCl$_3$).

Cis isomer: Melting point: 145° C. NMR spectrum (270 MHz, CDCl$_3$) δ ppm: 1.23 (3H, d, J=7 Hz), 3.22 (1H, t, J=2 Hz), 3.44 (1H, q, J=7 Hz), 3.75 (2H, s), 4.2–4.5 (4H, m), 4.87 (1H, d, J=14 Hz), 4.96 (1H, s), 5.15 (1H, d, J=14 Hz), 5.67 (1H, s), 6.6–6.8 (2H, m), 7.3–7.4 (1H, m), 7.34 (2H, d, J=8 Hz), 7.65 (2H, d, J=8 Hz), 7.68 (2H, d, J=8 Hz), 7.78 (1H, s), 7.79 (1H, s), 7.82 (1H, bs), 7.88 (2H, d, J=8 Hz). IR spectrum ν max (KBr) cm$^{-1}$: 3408, 2250, 1669, 1516, 1135. Mass spectrum m/z (EI): 605 (M$^+$), 133 (100%).

Example 8

4'-Chloro-4-[trans-5-[[(1R,2R)-2-(2, 4-difluorophenyl)-2-hydroxy-1-methyl-3-(1H-1,2,4-triazol-1-yl)propyl]thio]-1,3-dioxan-2-yl]benzanilide and cis isomer Thereof (Exemplification Compound Number 4-1)

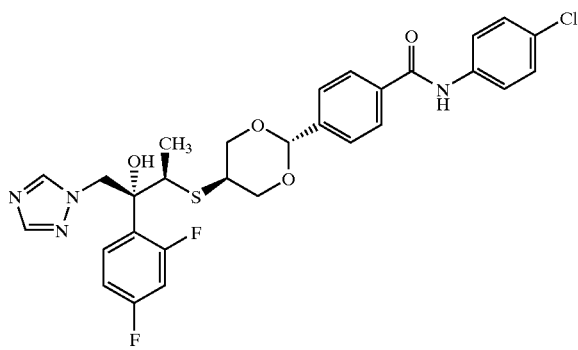

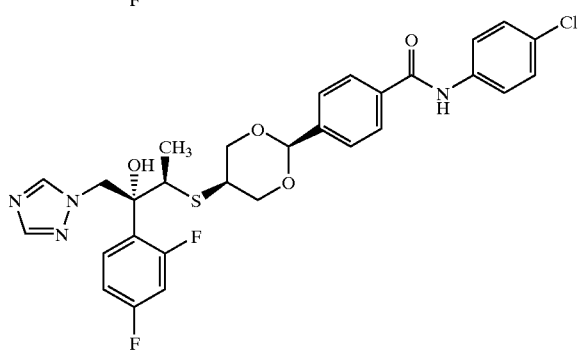

(1) In the same manner as that described in Example 2(1) a reaction was carried out using commercially available 4-chloroaniline (354 mg, 2.8 mmol), triethylamine (0.7 ml, 5.0 mmol), 4-formylbenzoyl chloride (700 mg, 4.2 mmol) and 4-(dimethylamino)pyridine (a catalytic amount) and the reaction mixture was treated according to a similar procedure to that described in Example 2(1) to afford 4'-chloro-4-formylbenzanilide (489 mg, yield 68%) as a white solid which was recrystallized from ethyl acetate-hexane to give white powdery crystals.

Melting point 173° C. NMR spectrum (270 MHz, CDCl$_3$) δ ppm: 7.37 (2H, d, J=9 Hz), 7.61 (2H, d, J=9 Hz), 7.82 (1H, bs), 8.02 (4H, s), 10.12 (1H, s). IR spectrum ν max (KBr) cm$^{-1}$: 3294, 1703, 1645, 1531, 1091. Mass spectrum m/z (EI): 259 (M$^+$), 133 (100%).

| Elemental analysis: | | | |
|---|---|---|---|
| Calculated for C$_{14}$H$_{10}$ClNO$_2$ | C: 64.75 | H: 3.88 | N: 5.39 |
| Found | C: 64.48 | H: 3.87 | N: 5.36. |

(2) In the same manner as that described in Example 3(3) a reaction was carried out using 4'-chloro-4-formylbenzanilide (300 mg, 1.2 mmol), (2R,3R)-2-(2,4-difluorophenyl)-3-[[1-(hydroxymethyl)-2-hydroxyethyl]thio]-1-(1H-1,2,4-triazol-1-yl)-2-butanol (359 mg, 1.0 mmol) and p-toluenesulfonic acid monohydrate (342 mg, 1.8 mmol) and the reaction mixture was treated according to a similar procedure to that described in Example 3(3) to give the trans isomer of the title compound (290 mg, yield 48%) as a colorless solid and the cis isomer (82 mg, yield 14%) as a colorless oil. The trans isomer was recrystallized from ethyl acetate-hexane to give white powdery crystals.

Trans isomer: Melting point:210° C. NMR spectrum (270 MHz, CDCl$_3$) δ ppm: 1.22 (3H, d, J=7 Hz), 3.36 (1H, q, J=7 Hz), 3.4–3.6 (1H, m), 3.76 (1H, t, J=11 Hz), 3.78 (1H, t, J=11 Hz), 4.42 (1H, ddd, J=11, 5, 2 Hz), 4.55 (1H, ddd, J=11, 5, 2 Hz), 4.85 (1H, d, J=14 Hz), 5.04 (1H, d, J=1 Hz), 5.05 (1H, d, J=14 Hz), 5.54 (1H, s), 6.7–6.8 (2H, m), 7.2–7.5 (1H, m), 7.35 (2H, d, J=8 Hz), 7.61 (2H, d, J=8 Hz), 7.62 (2H, d, J=8 Hz), 7.76 (1H, bs), 7.80 (2H, s), 7.88 (2H, d, J=8 Hz). IR spectrum ν max (KBr) cm$^{-1}$: 3396, 1659, 1531, 1140, 1080. Mass spectrum m/z (FAB): 601 (M$^+$+1).

| Elemental analysis: | | | |
|---|---|---|---|
| Calculated for C$_{29}$H$_{27}$ClF$_2$N$_4$O$_4$S | C: 57.95 | H: 4.53 | N: 9.32 | F: 6.32 |
| Found | C: 58.02 | H: 4.74 | N: 9.20 | F: 6.20. |

Specific rotation: [α]$_D^{25}$ –63° (c=0.63, CHCl$_3$).

Cis isomer: NMR spectrum (270 MHz, CDCl$_3$) δ ppm: 1.23 (3H, d, J=7 Hz), 3.21 (1H, t, J=2 Hz), 3.44 (1H, q, J=7 Hz), 4.2–4.5 (4H, m), 4.86 (1H, d, J=14 Hz), 4.96 (1H, s), 5.15 (1H, d, J=14 Hz), 5.66 (1H, s), 6.6–6.8 (2H, m), 7.2–7.5 (1H, m), 7.34 (2H, d, J=8 Hz), 7.61 (2H, d, J=8 Hz), 7.65 (2H, d, J=8 Hz), 7.78 (1H, s), 7.79 (1H, s), 7.82 (1H, bs), 7.87 (2H, d, J=8 Hz). Mass spectrum m/z (FAB): 601 (M$^+$+1).

Example 9

4'-Chloro-3-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide (Exemplification Compound Number 4-25)

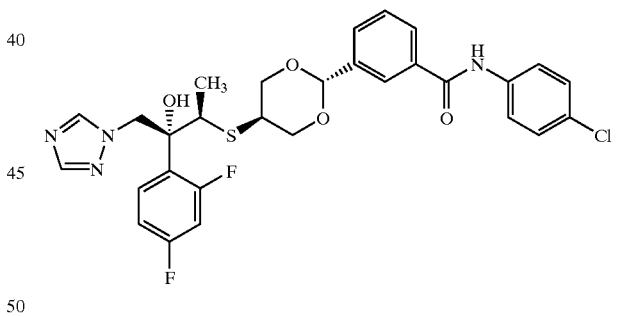

In the same manner as described in Example 3(4), a reaction was carried out using commercially available 4-chloroaniline (81 mg, 0.63 mmol), trimethylaluminium (0.59 ml, 1.07M n-hexane solution, 0.63 mmol) and methyl 3-[trans-5-[[(1R,2R)-2-(2,4-difluorophenyl)-2-7hydroxy-1-methyl-3-(1H-1,2,4-triazol-1-yl)propyl]thio]-1,3-dioxan-2-yl]benzoate (80 mg, 0.16 mmol), obtained in Example 6(1), and the reaction mixture was treated using a similar procedure to that described in Example 3(4) to afford the title compound (80 mg, yield 84%) as a pale yellow oil which was recrystallized from ethyl acetate-hexane to give pale yellow powdery crystals.

Melting point: 90° C. NMR spectrum (400 MHz, CDCl$_3$) δ ppm: 1.22 (3H, d, J=7 Hz), 3.36 (1H, q, J=7 Hz), 3.4–3.7 (1H, m), 3.77 (1H, t, J=11 Hz), 3.80 (1H, t, J=11 Hz), 4.42 (1H, ddd, J=11, 5, 2 Hz), 4.5–4.6 (1H, m), 4.85 (1H, d, J=14

Hz), 5.06 (1H, d, J=14 Hz), 5.07 (1H, s), 5.56 (1H, s), 6.7–6.9 (2H, m), 7.3–7.5 (1H, m), 7.35 (2H, d, J=8 Hz), 7.53 (1H, t, J=8 Hz), 7.61 (2H, d, J=8 Hz), 7.68 (1H, d, J=8 Hz), 7.80 (2H, s), 7.82 (1H, s), 7.91 (1H, d, J=8 Hz), 7.97 (1H, s). IR spectrum ν max (KBr) cm$^{-1}$: 3307, 1659, 1528, 1139. Mass spectrum m/z (FAB): 601 (M$^+$+1). Specific rotation: $[\alpha]_D^{25}$ –65° (c=0.49, CHCl$_3$).

Example 10

4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-4'-fluorobenzanilide and cis isomer Thereof (Exemplification Compound Number 5-1).

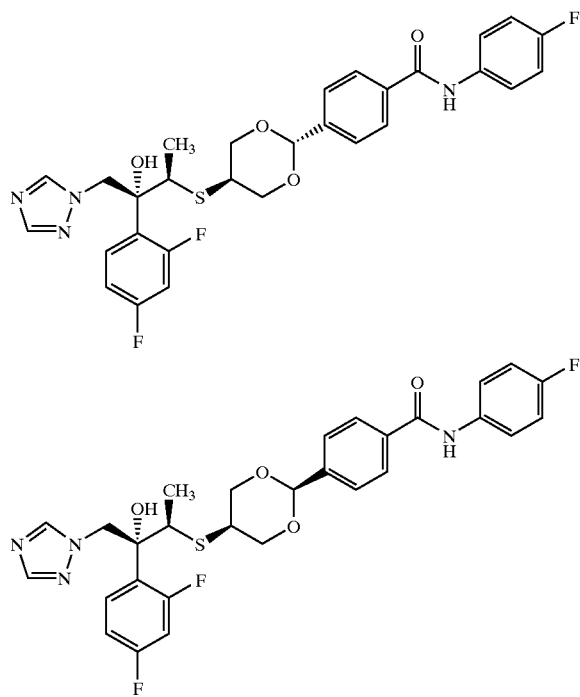

(1) In the same manner as that described in Example 1(1), a reaction was carried out using commercially available 4-fluoroaniline (308 mg, 2.8 mmol), triethylamine (0.7 ml, 5.0 mmol), 4-formylbenzoyl chloride (700 mg, 4.2 mmol) and 4-(dimethylamino)pyridine (a catalytic amount) and the reaction mixture was treated according to a similar procedure to that described in Example 1(1) to afford 4'-chloro-4-formylbenzanilide (527 mg, yield 78%) as a white solid which was recrystallized from ethyl acetate-hexane to give white powdery crystals.

Melting point: 158° C. NMR spectrum (270 MHz, CDCl$_3$) δ ppm: 7.10 (2H, t, J=9 Hz), 7.61 (2H, dd, J=9, 5 Hz), 7.80 (1H, bs), 8.02 (4H, s), 10.12 (1H, s). IR spectrum ν max (KBr) cm$^{-1}$: 3321, 1704, 1650, 1515, 1219. Mass spectrum m/z (EI): 243 (M$^+$), 133 (100%).

Elemental analysis:

| | | | |
|---|---|---|---|
| Calculated for C$_{14}$H$_{10}$FNO$_2$ | C: 69.13 | H: 4.14 | N: 5.76 |
| Found | C: 69.00 | H: 3.87 | N: 5.82. |

(2) In the same manner as that described in Example 3(3), a reaction was carried out using 4'-fluoro-4-formylbenzanilide (300 mg, 1.2 mmol), (2R,3R)-2-(2,4-difluorophenyl)-3-[[1-(hydroxymethyl)-2-hydroxyethyl]thio]-1-(1H-1,2,4-triazol-1-yl)-2-butanol (385 mg, 1.1 mmol) and p-toluenesulfonic acid monohydrate (366 mg, 1.9 mmol) and the reaction mixture was treated according to a similar procedure to that described in Example 3(3) to give the trans isomer of the title compound (306 mg, yield 48%) as a colorless oil and the cis isomer (78 mg, yield 12%) as a colorless oil. The trans isomer was recrystallized from ethyl acetate-hexane to give white powdery crystals.

Trans isomer: Melting point 104° C. NMR spectrum (270 MHz, CDCl$_3$) δ ppm: 1.22 (3H, d, J=7 Hz), 3.36 (1H, q, J=7 Hz), 3.4–3.6 (1H, m), 3.76 (1H, t, J=11 Hz), 3.78 (1H, t, J=11 Hz), 4.42 (1H, ddd, J=11, 5, 2 Hz), 4.55 (1H, ddd, J=11, 5, 2 Hz), 4.85 (1H, d, J=14 Hz), 5.05 (1H, s), 5.06 (1H, d, J=14 Hz), 5.54 (1H, s), 6.7–6.8 (2H, m), 7.08 (2H, t, J=8 Hz), 7.3–7.5 (1H, m), 7.5–7.7 (2H, m), 7.63 (2H, d, J=8 Hz), 7.75 (1H, bs), 7.80 (2H, s), 7.88 (2H, d, J=8 Hz). IR spectrum ν max (KBr) cm$^{-1}$: 3330, 1654, 1510, 1212, 1139. Mass spectrum m/z (FAB): 585 (M$^+$+1). Specific rotation: $[\alpha]_D^{25}$ –680 (c=0.64, CHCl$_3$).

Cis isomer: NMR spectrum (270 MHz, CDCl$_3$) δ ppm: 1.23 (3H, d, J=7 Hz), 3.21 (1H, t, J=2 Hz), 3.44 (1H, q, J=7 Hz), 4.2–4.5 (4H, m), 4.86 (1H, d, J=14 Hz), 4.96 (1H, s), 5.15 (1H, d, J=14 Hz), 5.66 (1H, s), 6.6–6.8 (2H, m), 7.07 (2H, t, J=8 Hz), 7.2–7.5 (1H, m), 7.5–7.7 (2H, m), 7.65 (2H, d, J=8 Hz), 7.78 (2H, bs), 7.79 (1H, s), 7.88 (2H, d, J=8 Hz). Mass spectrum m/z (FAB): 585 (M$^+$).

Example 11

4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-4'-(trifluoromethyl)benzanilide and cis isomer Thereof (Exemplification Compound Number 6-1)

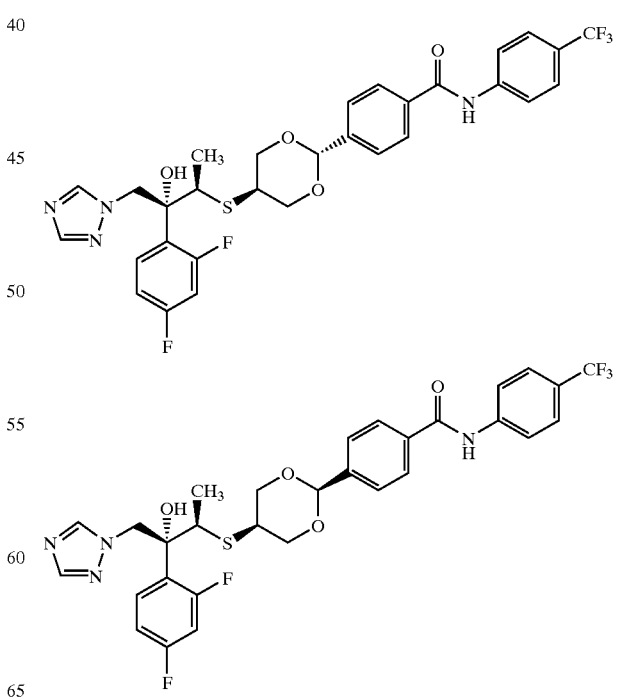

(1) In the same manner as that described in Example 2(1), a reaction was carried out using commercially available 4-(trifluoromethyl)aniline (446 mg, 2.8 mmol), triethylamine (0.6 ml, 4.4 mmol), 4-formylbenzoyl chloride (700 mg, 4.2 mmol) and 4-(dimethylamino)pyridine (a catalytic amount) and the reaction mixture was treated according to a similar procedure to that described in Example 2(1) to afford 4-formyl-4'-(trifluoromethyl)benzanilide (577 mg, yield 71%) as a white solid which was recrystallized from ethyl acetate-hexane to give white fluffy crystals.

Melting point: 173° C. NMR spectrum (270 MHz, CDCl$_3$) δ ppm: 7.67 (2H, d, J=9 Hz), 7.80 (2H, d, J=9 Hz), 7.93 (1H, bs), 8.05 (4H, s), 10.13 (1H, s). IR spectrum ν max (KBr) cm$^{-1}$: 3312, 1702, 1650, 1533, 1322. Mass spectrum m/z (EI): 293 (M$^+$), 133 (100%).

(2) In the same manner as that described in Example 3(3), a reaction was carried out using 4-formyl-4'-(trifluoromethyl)benzanilide (300 mg, 1.0 mmol), (2R,3R)-2-(2,4-difluorophenyl)-3-[[1-(hydroxymethyl)-2-hydroxyethyl]thio]-1-(1H-1,2,4-triazol-1-yl)-2-butanol (334 mg, 0.93 mmol) and p-toluenesulfonic acid monohydrate (318 mg, 1.7 mmol) and the reaction mixture was treated according to a similar procedure to that described in Example 3(3) to give the trans isomer of the title compound (275 mg, yield 47%) as a white solid and the cis isomer (58 mg, yield 10%) as a colorless oil. The trans isomer was recrystallized from ethyl acetate-hexane to give white powdery crystals.

Trans isomer: Melting point: 210° C. NMR spectrum (270 MHz, CDCl$_3$) δ ppm: 1.22 (3H, d, J=7 Hz), 3.36 (1H, q, J=7 Hz), 3.4–3.6 (1H, m), 3.77 (1H, t, J=11 Hz), 3.79 (1H, t, J=11 Hz), 4.41 (1H, ddd, J=11, 5, 2 Hz), 4.55 (1H, ddd, J=11, 5, 2 Hz), 4.85 (1H, d, J=14 Hz), 5.05 (1H, d, J=1 Hz), 5.05 (1H, d, J=14 Hz), 5.55 (1H, s), 6.7–6.8 (2H, m), 7.3–7.5 (1H, m), 7.64 (4H, d, J=8 Hz), 7.78 (2H, d, J=8 Hz), 7.80 (2H, s), 7.90 (2H, d, J=8 Hz), 7.91 (1H, bs). IR spectrum ν max (KBr) cm$^{-1}$: 3399, 1665, 1531, 1325, 1139. Mass spectrum m/z (FAB): 635 (M$^+$+1).

Elemental analysis:

| Calculated for C$_{30}$H$_{27}$F$_5$N$_4$O$_4$S | C: 56.78 | H: 4.29 | N: 8.83 | F: 14.97 |
|---|---|---|---|---|
| Found | C: 56.70 | H: 4.46 | N: 8.90 | F: 14.67. |

Cis isomer: NMR spectrum (270 MHz, CDCl$_3$) δ ppm: 1.23 (3H, d, J=7 Hz), 3.22 (1H, t, J=2 Hz), 3.44 (1H, q, J=7 Hz), 4.2–4.5 (4H, m), 4.86 (1H, d, J=14 Hz), 4.96 (1H, s), 5.15 (1H, d, J=14 Hz), 5.67 (1H, s), 6.6–6.8 (2H, m), 7.2–7.5 (1H, m), 7.64 (2H, d, J=B Hz), 7.67 (2H, d, J=8 Hz), 7.78 (1H, s), 7.79 (1H, s), 7.79 (2H, d, J=8 Hz), 7.89 (2H, d, J=8 Hz), 7.93 (1H, bs). Mass spectrum m/z (FAB): 635 (M$^+$+1).

Example 12

4-[trans-5-[[(1R,2R)-2-(2,4-Difluorophenyl)-2-hydroxy-1-methyl-3-(1H-1,2,4-triazol-1-yl)propyl] thio]-1,3-dioxan-2-yl]-4'-(trifluoromethoxy) benzanilide (Exemplification Compound Number 7-1)

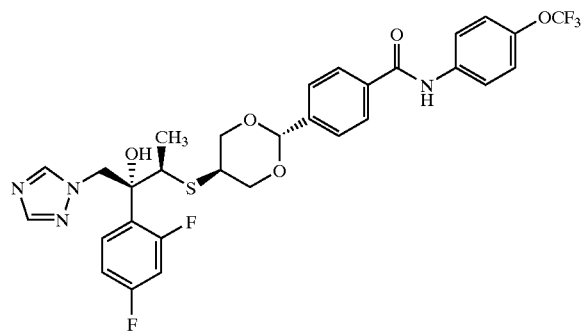

(1) In the same manner as that described in Example 3(3), a reaction was carried out using commercially available methyl 4-formylbenzoate (525 mg, 3.2 mmol), (2R,3R)-2-(2,4-difluorophenyl)-3-[[1-(hydroxymethyl)-2-hydroxyethyl]thio]-1-(1H-1,2,4-triazol-1-yl)-2-butanol (1.0 g, 2.8 mmol) and p-toluenesulfonic acid monohydrate (952 mg, 5.0 mmol) and the reaction mixture was treated according to a similar procedure to that described in Example 3(3) to afford methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-3-benzoate (936 mg, yield 67%) as a white solid which was recrystallized from ethyl acetate-hexane to give white prismatic crystals.

Melting point: 114° C. NMR spectrum (270 MHz, CDCl$_3$) δ ppm: 1.21 (3H, d, J=7 Hz), 3.36 (1H, q, J=7 Hz), 3.4–3.6 (1H, m), 3.75 (1H, t, J=11 Hz), 3.77 (1H, t, J=11 Hz), 3.92 (3H, s), 4.41 (1H, ddd, J=11, 5, 2 Hz), 4.53 (1H, ddd, J=11, 5, 2 Hz), 4.84 (1H, d, J=14 Hz), 5.03 (1H, s), 5.06 (1H, d, J=14 Hz), 5.52 (1H, s), 6.7–6.8 (2H, m), 7.3–7.5 (1H, m), 7.57 (2H, d, J=8 Hz), 7.79 (2H, s), 8.06 (2H, d, J=8 Hz). IR spectrum ν max (KBr) cm$^{-1}$: 3421, 1722, 1279, 1139. Mass spectrum m/z (FAB): 506 (M$^+$+1).

Elemental analysis:

| Calculated for C$_{24}$H$_{25}$F$_2$N$_3$O$_5$S | C: 57.02 | H: 4.99 | N: 8.31 | F: 7.52 |
|---|---|---|---|---|
| Found | C: 57.03 | H: 5.10 | N: 8.32 | F: 7.62. |

Specific rotation [α]$_D^{25}$ −81° (c=0.56, CHCl$_3$).

(2) In the same manner as that described in Example 3(4), a reaction was carried out using commercially available 4-(trifluoromethoxy)aniline (123 mg, 0.69 mmol), trimethylaluminium (0.64 ml, 1.07M n-hexane solution, 0.69 mmol) and methyl 4-[trans-5-[[(1R,2R)-2-(2,4-difluorophenyl)-2-hydroxy-1-methyl-3-(1H-1,2,4-triazol-1-yl)propyl]thio]-1, 3-dioxan-2-yl]benzoate (100 mg, 0.20 mmol), obtained in Example 12(1), and the reaction mixture was treated using a similar procedure to that described in Example 3(4) to afford the title compound (122 mg, yield 95%) as white solid which was recrystallized from ethyl acetate-hexane to give white powdery crystals.

Melting point 180° C. NMR spectrum (270 MHz, CDCl$_3$) δ ppm: 1.22 (3H, d, J=7 Hz), 3.36 (1H, q, J=7 Hz), 3.4–3.6

(1H, m), 3.76 (1H, t, J=11 Hz), 3.78 (1H, t, J=11 Hz), 4.42 (1H, ddd, J=11, 5, 2 Hz), 4.54 (1H, ddd, J=11, 5, 2 Hz), 4.85 (1H, d, J=14 Hz), 5.04 (1H, s), 5.06 (1H, d, J=14 Hz), 5.53 (1H, s), 6.7–6.8 (2H, m), 7.22 (2H, d, J=8 Hz), 7.3–7.5 (1H, m), 7.61 (2H, d, J=8 Hz), 7.67 (2H, d, J=8 Hz), 7.79 (2H, s), 7.87 (2H, d, J=8 Hz), 7.97 (1H, bs). IR spectrum ν max (KBr) cm$^{-1}$: 3390, 1656, 1511, 1265, 1140. Mass spectrum m/z (FAB): 651 (M$^+$+1).

| Elemental analysis: | | | | |
|---|---|---|---|---|
| Calculated for C$_{30}$H$_{27}$F$_5$N$_4$O$_5$S | C:55.38 | H:4.18 | N:8.61 | F:14.60 |
| Found | C:55.35 | H:4.13 | N:8.52 | F:14.32. |

Specific rotation: $[\alpha]_D^2 -60°$ (c=0.55, CHCl$_3$).

Example 13

4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-4'-(trifluoromethylthio)benzanilide (Exemplification Compound Number 8-1)

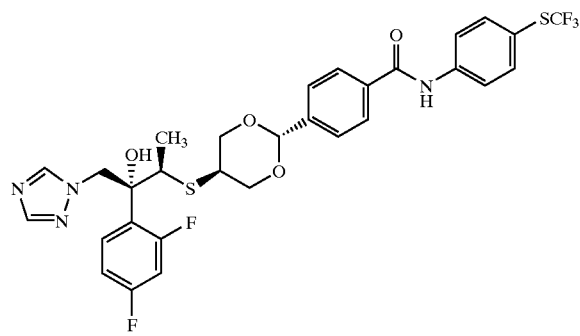

In the same manner as that described in Example 3(4), a reaction was carried out using commercially available 4-(trifluoromethylthio)aniline (230 mg, 1.2 mmol), trimethylaluminium (1.1 ml, 1.07M n-hexane solution, 1.2 mmol) and methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzoate (150 mg, 0.30 mmol), obtained in Example 12(1), and the reaction mixture was treated using a similar procedure to that described in Example 3(4) to afford the title compound (184 mg, yield 93%) as a colorless oil which was recrystallized from ethyl acetate-hexane to give white powdery crystals.

Melting point: 95° C. NMR spectrum (400 MHz, CDCl$_3$) δ ppm 1.22 (3H, d, J=7 Hz), 3.36 (1H, q, J=7 Hz), 3.4–3.6 (1H, m), 3.76 (1H, t, J=11 Hz), 3.79 (1H, t, J=11 Hz), 4.42 (1H, ddd, J=11, 5, 2 Hz), 4.55 (1H, ddd, J=11, 5, 2 Hz), 4.85 (1H, d, J=14 Hz), 5.05 (1H, d, J=1 Hz), 5.06 (1H, d, J=14 Hz), 5.55 (1H, s), 6.7–6.8 (2H, m), 7.3–7.5 (1H, m), 7.64 (2H, d, J=8 Hz), 7.67 (2H, d, J=8 Hz), 7.74 (2H, d, J=8 Hz), 7.80 (2H, s), 7.87 (1H, bs), 7.89 (2H, d, J=8 Hz). IR spectrum ν max (KBr) cm$^{-1}$: 3320, 1667, 1527, 1139, 1122. Mass spectrum m/z (FAB): 667 (M$^+$+1). Specific rotation: $[\alpha]_D^{25} -64°$ (c=0.54, CHCl$_3$).

Example 14

4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-4'-methylbenzanilide (Exemplification Compound Number 9-1)

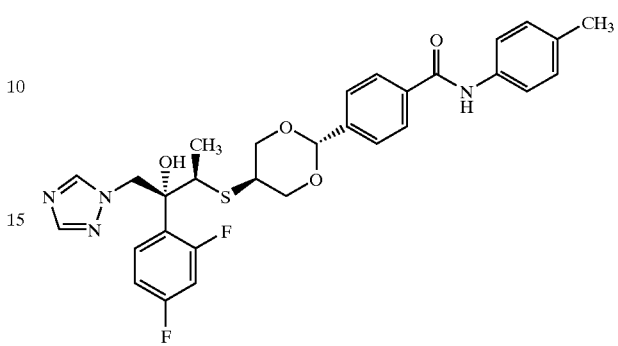

In the same manner as that described in Example 3(4), a reaction was carried out using commercially available p-toluidine (128 mg, 1.2 mmol), trimethylaluminium (1.1 ml, 1.07M n-hexane solution, 1.2 mmol) and methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzoate (150 mg, 0.30 mmol), obtained in Example 12(1), and the reaction mixture was treated using a similar procedure to that described in Example 3(4) to afford the title compound (166 mg, yield 96%) as a pale yellow oil which was recrystallized from ethyl acetate-hexane to give white powdery crystals.

Melting point: 101° C. NMR spectrum (400 MHz, CDCl$_3$) δ ppm: 1.21 (3H, d, J=7 Hz), 2.35 (3H, s), 3.36 (1H, q, J=7 Hz), 3.4–3.6 (1H, m), 3.76 (1H, t, J=11 Hz), 3.78 (1H, t, J=11 Hz), 4.42 (1H, ddd, J=11, 5, 2 Hz), 4.54 (1H, ddd, J=11, 5, 2 Hz), 4.85 (1H, d, J=14 Hz), 5.05 (1H, s), 5.06 (1H, d, J=14 Hz), 5.54 (1H, s), 6.7–6.8 (2H, m), 7.18 (2H, d, J=8 Hz), 7.3–7.4 (1H, m), 7.52 (2H, d, J=8 Hz), 7.61 (2H, d, J=8 Hz), 7.73 (1H, bs), 7.80 (2H, s), 7.88 (2H, d, J=8 Hz). IR spectrum ν max (KBr) cm$^{-1}$: 3322, 1666, 1515, 1139. Mass spectrum m/z (FAB): 581 (M$^+$+1). Specific rotation: $[\alpha]_D^{25} -70°$ (c=0.50, CHCl$_3$).

Example 15

4'-Bromo-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide (Exemplification Compound Number 10-1)

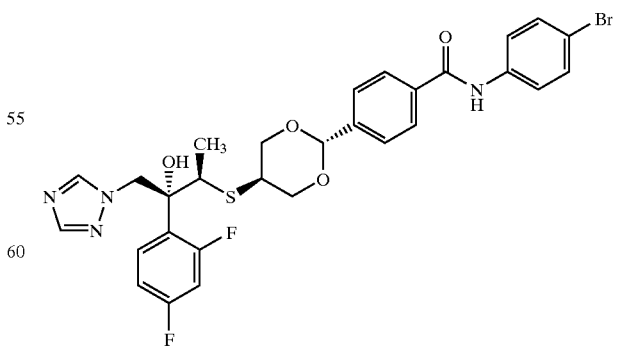

In the same manner as that described in Example 3(4), a reaction was carried out using commercially available 4-bromoaniline (205 mg, 1.2 mmol), trimethylaluminium (1.1 ml, 1.07M n-hexane solution, 1.2 mmol) and methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzoate (150 mg, 0.30 mmol), obtained in Example 12(1), and the reaction mixture was treated using a similar procedure to that described in Example 3(4) to afford the title compound (182 mg, yield 95%) as a white solid which was recrystallized from ethyl acetate to give white powdery crystals.

Melting point: 221° C. NMR spectrum (400 MHz, CDCl$_3$) δ ppm: 1.21 (3H, d, J=7 Hz), 3.36 (1H, q, J=7 Hz), 3.4–3.6 (1H, m), 3.76 (1H, t, J=11 Hz), 3.78 (1H, t, J=11 Hz), 4.41 (1H, ddd, J=11, 5, 2 Hz), 4.55 (1H, ddd, J=11, 5, 2 Hz), 4.85 (1H, d, J=14 Hz), 5.05 (1H, d, J=1 Hz), 5.06 (1H, d, J=14 Hz), 5.54 (1H, s), 6.7–6.8 (2H, m), 7.3–7.4 (1H, m), 7.49 (2H, d, J=9 Hz), 7.56 (2H, d, J=9 Hz), 7.62 (2H, d, J=9 Hz), 7.76 (1H, bs), 7.80 (2H, s), 7.88 (2H, d, J=9 Hz). IR spectrum ν max (KBr) cm$^{-1}$: 3399, 1660, 1529, 1139. Mass spectrum m/z (FAB): 645 (M$^+$+1).

| Elemental analysis: | | | | |
|---|---|---|---|---|
| Calculated for C$_{29}$H$_{27}$BrF$_2$N$_4$O$_4$S | C:53.96 | H:4.22 | N:8.68 | F:5.89 |
| Found | C:53.86 | H:4.32 | N:8.55 | F:5.98. |

Specific rotation: $[α]_D^{25}$ −66° (c=0.64, CHCl$_3$).

Example 16

3'-Chloro-4'-cyano-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide (Exemplification Compound Number 11-1)

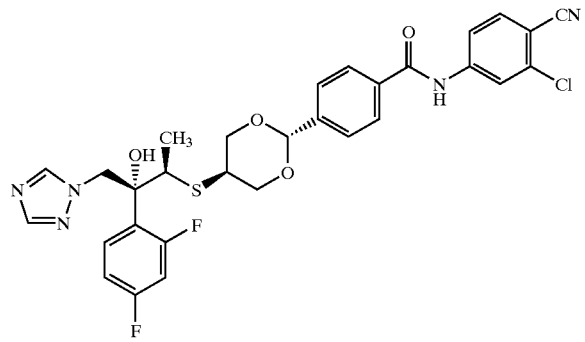

In the same manner as that described in Example 3(4), a reaction was carried out using commercially available 4-amino-2-chlorobenzonitrile (182 mg, 1.2 mmol), trimethylaluminium (1.1 ml, 1.07M n-hexane solution, 1.2 mmol) and methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzoate (150 mg, 0.30 mmol), obtained in Example 12(1), and the reaction mixture was treated using a similar procedure to that described in Example 3(4) to afford the title compound (167 mg, yield 90%) as a colorless oil which was recrystallized from ethyl acetate-isopropyl ether to give white powdery crystals.

Melting point: 115° C. NMR spectrum (400 MHz, CDCl$_3$) δ ppm: 1.21 (3H, d, J=7 Hz), 3.36 (1H, q, J=7 Hz), 3.4–3.6 (1H, m), 3.76 (1H, t, J=11 Hz), 3.78 (1H, t, J=11 Hz), 4.42 (1H, ddd, J=11, 5, 2 Hz), 4.55 (1H, ddd, J=11, 5, 2 Hz), 4.85 (1H, d, J=14 Hz), 5.05 (1H, d, J=1 Hz), 5.05 (1H, d, J=14 Hz), 5.54 (1H, s), 6.7–6.8 (2H, m), 7.2–7.4 (1H, m), 7.6–7.7 (4H, m), 7.80 (2H, s), 7.88 (2H, d, J=8 Hz), 7.98 (1H, bs), 8.02 (1H, d, J=2 Hz). IR spectrum ν max (KBr) cm$^{-1}$: 3426, 2229, 1685, 1503, 1139, 1077. Mass spectrum m/z (FAB): 626 (M$^+$+1). Specific rotation $[α]_D^{25}$ −59° (c=0.55, CHCl$_3$).

Example 17

4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-N-(4-pyridyl)benzamide and cis isomer thereof (Exemplification Compound Number 12-1)

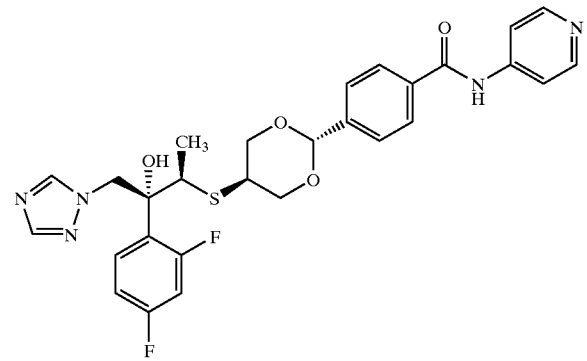

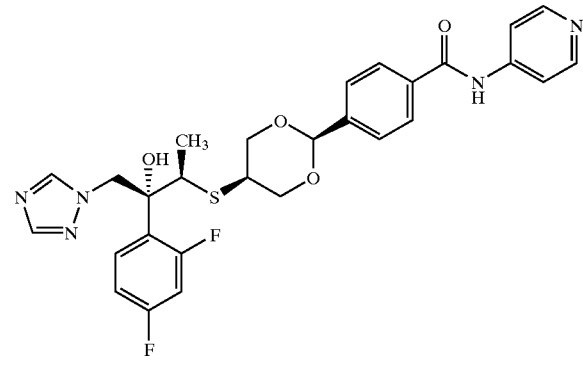

(1) In the same manner as that described in Example 1(1), a reaction was carried out using commercially available 4-aminopyridine (159 mg, 1.7 mmol), triethylamine (0.38 ml, 2.7 mmol) and 4-formylbenzoyl chloride (400 mg, 2.4 mmol) and the reaction mixture was treated according to a similar procedure to that described in Example 1(1) to afford a crystalline residue which was recrystallized from a mixture of tetrahydrofuran and hexane to give 4-formyl-N-(4-pyridyl)benzamide (214 mg, yield 56%) as white powdery crystals.

Melting point: 161° C. NMR spectrum (400 MHz, CDCl$_3$) δ ppm: 7.79 (2H, d, J=6 Hz), 8.08 (2H, d, J=8 Hz), 8.15 (2H, d, J=8 Hz), 8.51 (2H, d, J=6 Hz), 10.13 (1H, s), 10.81 (1H, s). IR spectrum ν max (KBr) cm$^{-1}$: 3234, 1700, 1596, 1512, 1330. Mass spectrum m/z (EI): 226 (M$^+$), 133 (100%).

(2) In the same manner as that described in Example 3(3), a reaction was carried out using 4-formyl-N-(4-pyridyl) benzamide (200 mg, 0.88 mmol), (2R,3R)-2-(2,4-difluorophenyl)-3-[[1-(hydroxymethyl)-2-hydroxyethyl] thio]-1-(1H-1,2,4-triazol-1-yl)-2-butanol (318 mg, 0.88 mmol) and p-toluenesulfonic acid monohydrate (469 mg, 2.5 mmol) and the reaction mixture was treated according to a similar procedure to that described in Example 3(3) to give the trans isomer of the title compound (187 mg, yield 37%) as a white solid and the cis isomer (86 mg, yield 17%) as a colorless oil. The trans isomer was recrystallized from ethyl acetate-hexane to give white powdery crystals.

Trans isomer: Melting point: 133° C. NMR spectrum (400 MHz, CD$_3$OD) δ ppm: 1.20 (3H, d, J=7 Hz), 3.3–3.5 (1H, m), 3.62 (1H, q, J=7 Hz), 3.82 (1H, t, J=11 Hz), 3.82 (1H, t, J=11 Hz), 4.4–4.5 (2H, m), 4.92 (1H, d, J=14 Hz), 5.06 (1H, d, J=14 Hz), 5.63 (1H, s), 6.7–7.0 (2H, m), 7.2–7.4 (1H, m), 7.64 (2H, d, J=8 Hz), 7.71 (1H, s), 7.84 (2H, d, J=7 Hz), 7.95 (2H, d, J=8 Hz), 8.23 (1H, s), 8.44 (2H, d, J=7 Hz). IR spectrum ν max (KBr) cm$^{-1}$: 3414, 1684, 1593, 1139. Mass spectrum m/z (FAB): 568 (M$^+$+1). Specific rotation: $[α]_D^{25}$ −42° (c=0.45, CH$_3$OH)

Cis isomer: NMR spectrum (400 MHz, CD$_3$OD) δ ppm: 1.20 (3H, d, J=7 Hz), 3.12 (1H, s), 3.65 (1H, q, J=7 Hz), 4.3–4.6 (4H, m), 4.93 (1H, d, J=14 Hz), 5.17 (1H, d, J=$_{14}$ Hz), 5.72 (1H, s), 6.7–7.0 (2H, m), 7.3–7.4 (1H, m), 7.67 (2H, d, J=8 Hz), 7.68 (1H, s), 7.84 (2H, d, J=7 Hz), 7.96 (2H, d, J=8 Hz), 8.25 (1H, s), 8.44 (2H, d, J=7 Hz). Mass spectrum m/z (FAB): 568 (M$^+$+1).

Example 18

4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-4-nitrobenzanilide
(Exemplification Compound Number 13-1)

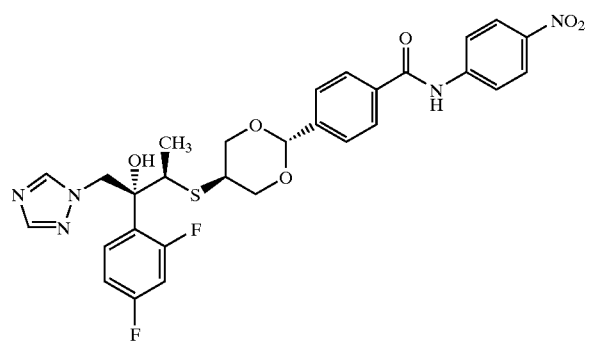

In the same manner as that described in Example 3(4), a reaction was carried out using commercially available 4-nitroaniline (165 mg, 1.2 mmol), trimethylaluminium (1.1 ml, 1.07M n-hexane solution, 1.2 mmol) and methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzoate (150 mg, 0.30 mmol), obtained in Example 12(1), and the reaction mixture was treated using a similar procedure to that described in Example 3(4) to afford the title compound (169 mg, yield 93%) as a pale orange solid which was recrystallized from ethyl acetate-hexane to give pale yellow fluffy crystals.

Melting point: 189° C. NMR spectrum (400 MHz, CDCl$_3$) δ ppm: 1.22 (3H, d, J=7 Hz), 3.37 (1H, q, J=7 Hz), 3.4–3.6 (1H, m), 3.76 (1H, t, J=11 Hz), 3.79 (1H, t, J=11 Hz), 4.42 (1H, ddd, J=11, 5, 2 Hz), 4.55 (1H, ddd, J=11, 5, 2 Hz), 4.85 (1H, d, J=14 Hz), 5.05 (1H, d, J=1 Hz), 5.05 (1H, d, J=14 Hz), 5.55 (1H, s), 6.7–6.8 (2H, m), 7.3–7.4 (1H, m), 7.65 (2H, d, J=9 Hz), 7.80 (2H, s), 7.86 (2H, d, J=9 Hz), 7.90 (2H, d, J=9 Hz), 8.09 (1H, bs), 8.27 (2H, d, J=9 Hz). IR spectrum ν max (KBr) cm$^{-1}$: 3397, 1681, 1501, 1140. Mass spectrum m/z (FAB): 612 (M$^+$+1).

| Elemental analysis: | | | | |
|---|---|---|---|---|
| Calculated for C$_{29}$H$_{27}$F$_2$N$_5$O$_6$S | C:56.95 | H:4.45 | N:11.45 | F:6.21 |
| Found | C:57.24 | H:4.25 | N:11.32 | F:6.13. |

Specific rotation: $[α]_D^{25}$ −62° (c=0.51, CHCl$_3$).

Example 19

N-(4-Cyano-1-naphthyl)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzamide
(Exemplification Compound Number 38-1)

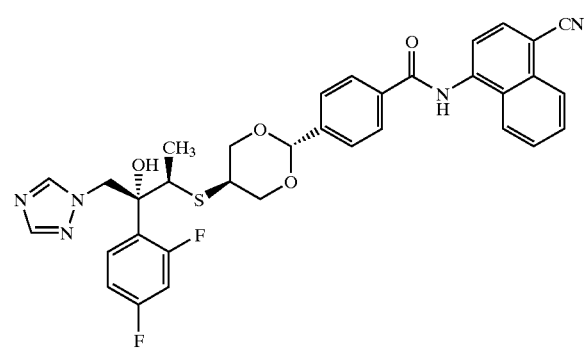

In the same manner as that described in Example 3(4), a reaction was carried out using commercially available 4-amino-1-naphthalenecarbonitrile (200 mg, 1.2 mmol), trimethylaluminium (1.1 ml, 1.07M n-hexane solution, 1.2 mmol) and methyl 4-[trans-5-[[(1R,2R)-2-(2,4-difluorophenyl)-2-hydroxy-1-methyl-$^3$-(1H-1,2,4-triazol-1-yl)propyl]thio]-1,3-dioxan-2-yl]benzoate (150 mg, 0.30 mmol), obtained in Example 12(1), and the reaction mixture was treated using a similar procedure to that described in Example 3(4) to afford the title compound (73 mg, yield 38%) as a pale yellow oil which was recrystallized from ethyl acetate-hexane to give white powdery crystals.

Melting point: 109° C. NMR spectrum (400 MHz, CDCl$_3$) δ ppm: 1.22 (3H, d, J=7 Hz), 3.37 (1H, q, J=7 Hz), 3.5–3.6 (1H, m), 3.78 (1H, t, J=11 Hz), 3.81 (1H, t, J=11 Hz), 4.44 (1H, ddd, J=11, 5, 2 Hz), 4.57 (1H, ddd, J=11, 5, 2 Hz), 4.85 (1H, d, J=14 Hz), 5.06 (1H, s), 5.06 (1H, d, J=14 Hz), 5.58 (1H, s), 6.7–6.8 (2H, m), 7.2–7.5 (1H, m), 7.70 (2H, d, J=8 Hz), 7.80 (2H, s), 7.6–7.8 (2H, m), 7.9–8.1 (2H, m), 8.00 (2H, d, J=8 Hz), 8.33 (1H, d, J=8 Hz), 8.43 (1H, d, J=8 Hz), 8.46 (1H, bs). IR spectrum ν max (KBr) cm$^{-1}$: 3409, 2221, 1662, 1528, 1139. Mass spectrum m/z (FAB): 642 (M$^+$+1). Specific rotation: $[α]_D^{25}$ −62° (c=0.58, CHCl$_3$).

Example 20

4'-Cyano-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-2',3',5',6'-tetrafluorobenzanilide (Exemplification Compound Number 14-1)

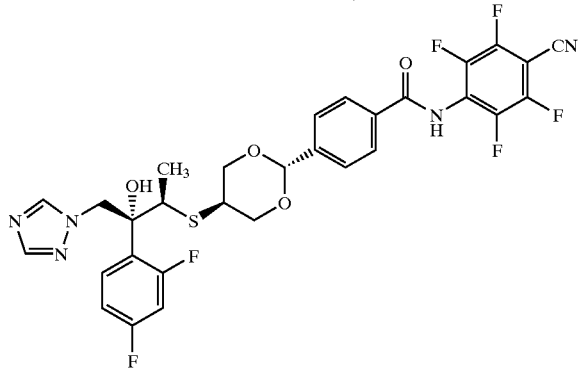

In the same manner as that described in Example 3(4), a reaction was carried out using commercially available 4-amino-2,3,5,6-tetrafluorobenzonitrile (227 mg, 1.2 mmol), trimethylaluminium (1.1 ml, 1.07M n-hexane solution, 1.2 mmol) and methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzoate (150 mg, 0.30 mmol), obtained in Example 12(1), and the reaction mixture was treated using a similar procedure to that described in Example 3(4) to afford the title compound (84 mg, yield 42%) as a colorless oil which was recrystallized from ethyl acetate-hexane to give white powdery crystals.

Melting point: 182° C. NMR spectrum (400 MHz, CDCl$_3$) δ ppm: 1.22 (3H, d, J=7 Hz), 3.36 (1H, q, J=7 Hz), 3.5–3.6 (1H, m), 3.76 (1H, t, J=11 Hz), 3.79 (1H, t, J=11 Hz), 4.43 (1H, ddd, J=11, 5, 2 Hz), 4.56 (1H, ddd, J=11, 5, 2 Hz), 4.85 (1H, d, J=14 Hz), 5.05 (1H, d, J=14 Hz), 5.06 (1H, s), 5.55 (1H, s), 6.7–6.8 (2H, m), 7.3–7.4 (1H, m), 7.66 (1H, s), 7.67 (2H, d, J=8 Hz), 7.80 (2H, s), 7.94 (2H, d, J=8 Hz). IR spectrum ν max (KBr) cm$^{-1}$: 3290, 2245, 1684, 1505, 1140. Mass spectrum m/z (FAB): 664 (M$^+$+1). Specific rotation: [α]$_D^{25}$ −61° (c=0.49, CHCl$_3$).

Example 21

3',4'-Dicyano-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide (Exemplification Compound Number 15-1)

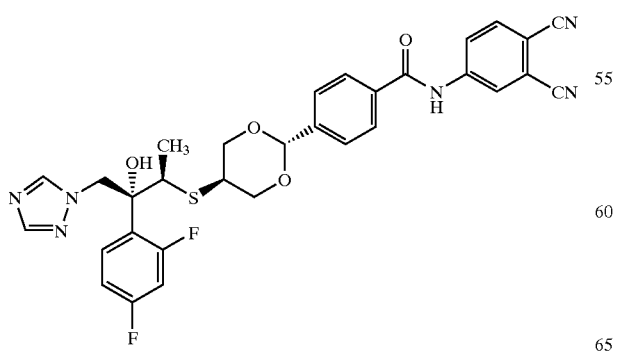

In the same manner as that described in Example 3(4), a reaction was carried out using commercially available 4-aminophthalonitrile (170 mg, 1.2 mmol), trimethylaluminium (1.1 ml, 1.07M n-hexane solution, 1.2 mmol) and methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzoate (150 mg, 0.30 mmol), obtained in Example 12(1), and the reaction mixture was treated using a similar procedure to that described in Example 3(4) to afford the title compound (129 mg, yield 71%) as a yellow oil which was recrystallized from ethyl acetate-hexane to give pale yellow powdery crystals.

Melting point: 182° C. NMR spectrum (400 MHz, CDCl$_3$) δ ppm: 1.24 (3H, d, J=7 Hz), 3.36 (1H, q, J=7 Hz), 3.4–3.6 (1H, m), 3.76 (1H, t, J=11 Hz), 3.79 (1H, t, J=11 Hz), 4.42 (1H, ddd, J=11, 5, 2 Hz), 4.56 (1H, ddd, J=11, 5, 2 Hz), 4.85 (1H, d, J=14 Hz), 5.05 (1H, d, J=14 Hz), 5.05 (1H, d, J=1 Hz), 5.55 (1H, s), 6.7–6.8 (2H, m), 7.3–7.5 (1H, m), 7.67 (2H, d, J=8 Hz), 7.80 (2H, s), 7.80 (1H, d, J=8 Hz), 7.89 (2H, d, J=8 Hz), 8.00 (1H, dd, J=8, 2 Hz), 8.14 (1H, s), 8.27 (1H, d, J=2 Hz). IR spectrum ν max (KBr) cm$^{-1}$: 3341, 2232, 1688, 1139. Mass spectrum m/z (FAB): 617 (M$^+$+1). Specific rotation: [α]$_D^{25}$ −630 (c=0.60, CHCl$_3$).

Example 22

4'-Acetyl-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide (Exemplification Compound Number 16-1)

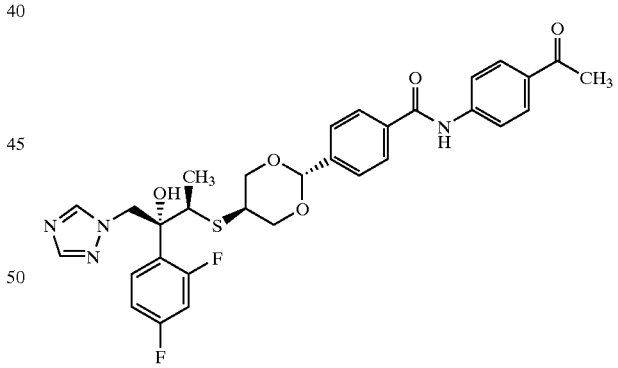

(1) In the same manner as that described in Example 1(1), a reaction was carried out using commercially available p-aminoacetophenone (309 mg, 2.3 mmol), triethylamine (0.48 ml, 3.4 mmol), and 4-formylbenzoyl chloride (500 mg, 3.0 mmol) and the reaction mixture was treated according to a similar procedure to that described in Example 1(1) to afford a crystalline residue which was recrystallized from a mixture of tetrahydrofuran and hexane to give 4'-acetyl-4-formylbenzanilide (552. mg, yield 90%) as pale yellow powdery crystals.

Melting point: 174° C. NMR spectrum (400 MHz, DMSO-$d_6$) δ ppm: 2.56 (3H, s), 7.95 (2H, d, J=8 Hz), 8.00 (2H, d, J=8 Hz), 8.07 (2H, d, J=8 Hz), 8.16 (2H, d, J=8 Hz), 10.13 (1H, s), 10.77 (1H, bs). IR spectrum ν max (KBr) $cm^{-1}$: 3348, 1703, 1679, 1659, 1529. Mass spectrum m/z (EI): 267 ($M^+$), 133 (100%).

(2) In the same manner as that described in Example 3(3), a reaction was carried out using 4'-acetyl-4-formylbenzanilide (200 mg, 0.75 mmol), (2R,3R)-2-(2,4-difluorophenyl)-3-[[1-(hydroxymethyl)-2-hydroxyethyl]thio]-1-(1H-1,2,4-triazol-1-yl)-2-butanol (256 mg, 0.71 mmol) and p-toluenesulfonic acid monohydrate (243 mg, 1.3 mmol) and the reaction mixture was treated according to a similar procedure to that described in Example 3(3) to give the trans isomer of the title compound (280 mg, yield 65%) as a white solid which was recrystallized from ethyl acetate-hexane to give white powdery crystals.

Trans isomer: Melting point: 171° C. NMR spectrum (400 MHz, $CDCl_3$) δ ppm: 1.22 (3H, d, J=7 Hz), 2.61 (3H, s), 3.3–3.4 (1H, m), 3.4–3.6 (1H, m), 3.77 (1H, t, J=11 Hz), 3.79 (1H, t, J=11 Hz), 4.42 (1H, m), 4.55 (1H, ddd, J=11, 5, 2 Hz), 4.85 (1H, d, J=14 Hz), 5.05 (1H, s), 5.06 (1H, d, J=14 Hz), 5.55 (1H, s), 6.7–6.8 (2H, m), 7.3–7.5 (1H, m), 7.64 (2H, d, J=8 Hz), 7.77 (2H, d, J=8 Hz), 7.80 (2H, s), 7.90 (2H, d, J=8 Hz), 7.94 (1H, s), 8.00 (2H, d, J=8 Hz). IR spectrum ν max (KBr) $cm^{-1}$: 3347, 1677, 1527, 1139. Mass spectrum m/z (FAB): 609 ($M^+$+1).

| Elemental analysis: | | | | |
|---|---|---|---|---|
| Calculated for $C_{31}H_{30}F_2N_4O_5S$ | C:61.17 | H:4.97 | N:9.21 | F:6.24 |
| Found | C:61.24 | H:4.93 | N:9.00 | F:6.20. |

Specific rotation: $[α]_D^5$ −59° (c=0.54, $CHCl_3$).

Example 23

(1) 4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-4'-hydroxybenzanilide (Exemplification Compound Number 27-1)

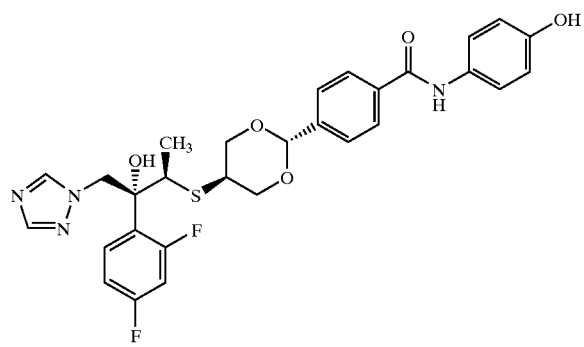

(1) In the same manner as that described in Example 3(4), a reaction was carried out using 4-(t-butyldimethylsilyloxy) aniline (266 mg, 1.2 mmol), described in J. Org. Chem., 54(1), 51 (1998), trimethylaluminium (1.1 ml, 1.07M n-hexane solution, 1.2 mmol) and methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzoate (150 mg, 0.30 mmol), obtained in Example 12(1), and the reaction mixture was treated using a similar procedure to that described in Example 3(4) to afford 4'-(t-butyldimethylsilyloxy)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide (182 mg, yield 88%) as a colorless oil.

NMR spectrum (400 MHz, $CDCl_3$) δ ppm: 0.20 (6H, 6), 0.99 (9H, s), 1.21 (3H, d, J=7 Hz), 3.36 (1H, q, J=7 Hz), 3.4–3.6 (1H, m), 3.76 (1H, t, J=11 Hz), 3.78 (1H, t, J=11 Hz), 4.42 (1H, ddd, J=11, 5, 2 Hz), 4.54 (1H, ddd, J=11, 5, 2 Hz), 4.85 (1H, d, J=14 Hz), 5.05 (1H, d, J=14 Hz), 5.05 (1H, d, J=1 Hz), 5.53 (1H, s), 6.7–6.8 (2H, m), 6.85 (2H, d, J=8 Hz), 7.2–7.4 (1H, m), 7.48 (2H, d, J=8 Hz), 7.60 (2H, d, J=8 Hz), 7.69 (1H, s), 7.80 (2H, s), 7.87 (2H, d, J=8 Hz). Mass spectrum m/z (FAB): 697 ($M^+$+1).

(2) Tetra-n-butylammonium fluoride (0.40 ml, 1 mol/l tetrahydrofuran solution, a product of Tokyokasei Kougyo Kabushiki Kaisha, 0.40 mmol) was added dropwise to a solution of 4'-(t-butyldimethylsilyloxy)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide (186 mg, 0.27 mmol), obtained in Example 23(1), in tetrahydrofuran (6 ml) cooled to 0° C. with stirring. The resulting mixture was stirred at 0° C. for 20 minutes. At the end of this time, saturated aqueous sodium hydrogencarbonate solution was added to the reaction mixture at 0° C. The resulting mixture was partitioned between ethyl acetate and water. The organic layer was washed with saturated aqueous sodium chloride solution, dried over anhydrous magnesium sulfate and concentrated under reduced pressure. The crystalline residue was recrystallized from a mixture of tetrahydrofuran and ethyl acetate to give the title compound (136 mg, yield 87%) as white powdery crystals.

Melting point: 254° C. NMR spectrum (400 MHz, DMSO-$d_6$) δ ppm: 1.10 (3H, d, J=7 Hz), 3.3–3.5 (1H, m), 3.57 (1H, q, J=7 Hz), 3.76 (1H, t, J=11 Hz), 3.76 (1H, t, J=11 Hz), 4.3–4.5 (2H, m), 4.81 (1H, d, J=14 Hz), 4.90 (1H, d, J=14 Hz), 5.66 (1H, s), 6.01 (1H, s), 6.74 (2H, d, J=9 Hz), 6.9–7.0 (1H, m), 7.1–7.2 (1H, m), 7.2–7.3 (1H, m), 7.52 (2H, d, J=9 Hz), 7.54 (2H, d, J=9 Hz), 7.67 (1H, s), 7.94 (2H, d, J=9 Hz), 8.27 (1H, s), 9.26 (1H, bs), 10.05 (1H, bs). IR spectrum ν max (KBr) $cm^{-1}$: 3286, 1652, 1513, 1139. Mass spectrum m/z (FAB): 583 ($M^+$+1). Specific rotation: $[α]_D^{25}$ −50° (c=0.20, THF).

Example 24

4'-Acetoxy-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide
(Exemplification Compound Number 17-1)

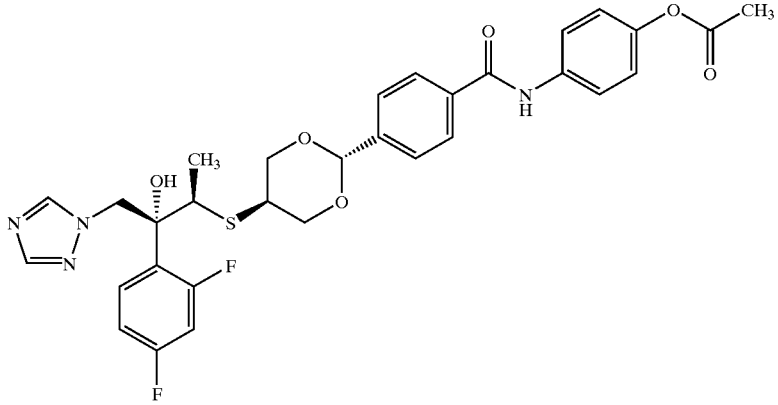

Acetic anhydride (1.5 ml) was added dropwise to a solution of 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-4'-hydroxybenzanilide (40 mg, 0.07 mmol), obtained in Example 23(2), in anhydrous pyridine (3 ml) cooled to 0° C. with stirring. The resulting mixture was stirred at room temperature overnight. At the end of this time, the reaction mixture was poured into saturated aqueous sodium hydrogencarbonate solution at 0° C. The resulting mixture was partitioned between ethyl acetate and water. The organic layer was washed with saturated aqueous sodium chloride solution, dried over anhydrous magnesium sulfate and concentrated under reduced pressure to afford the title compound (43 mg, yield 100%) as a colorless oil. The oil was recrystallized from ethyl acetate-hexane to give white powdery crystals.

Melting point: 127° C. NMR spectrum (400 MHz, CDCl$_3$) δ ppm: 1.22 (3H, d, J=7 Hz), 2.31 (3H, s), 3.36 (1H, q, J=7 Hz), 3.4–3.6 (1H, m), 3.76 (1H, t, J=11 Hz), 3.78 (1H, t, J=11 Hz), 4.42 (1H, ddd, J=11, 5, 2 Hz), 4.55 (1H, ddd, J=11, 5, 2 Hz), 4.85 (1H, d, J=14 Hz), 5.05 (1H, s), 5.06 (1H, d, J=14 Hz), 5.54 (1H, s), 6.7–6.8 (2H, m), 7.11 (2H, d, J=8 Hz), 7.3–7.4 (1H, m), 7.62 (2H, d, J=8 Hz), 7.66 (2H, d, J=8 Hz), 7.80 (3H, s), 7.88 (2H, d, J=8 Hz). IR spectrum ν max (KBr) cm$^{-1}$: 3372, 1670, 1509, 1139. Mass spectrum m/z (FAB): 625 (M$^+$+1). Specific rotation: [α]$_D^{25}$ –63° (c=0.55, CHCl$_3$).

Example 25

4'-Cyano-2'-fluoro-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide
(Exemplification Compound Number 18-1)

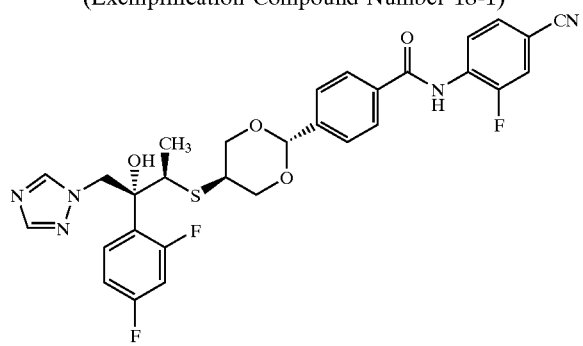

(1) 4-Methoxybenzylamine (5.6 ml, 43.1 mmol) was added dropwise to a solution of commercially available 3,4-difluorobenzonitrile (2.0 g, 14.4 mmol) in anhydrous di(ethylene glycol) dimethyl ether (10 ml) cooled to 0° C. with stirring. The resulting mixture was stirred at 120° C. for 1 hour. At the end of this time, the reaction mixture was poured into saturated aqueous sodium hydrogencarbonate solution at room temperature. The resulting mixture was partitioned between ethyl acetate and water. The organic layer was washed with saturated aqueous sodium chloride solution, dried over anhydrous magnesium sulfate and concentrated under reduced pressure. Hexane was added to the crystalline residue to give 3-fluoro-4-[(4-methoxybenzyl)amino]benzonitrile (2.26 g, yield 61%) as white fluffy crystals.

Melting point: 113° C. NMR spectrum (400 MHz, CDCl$_3$) δ ppm: 3.81 (3H, s), 4.34 (2H, d, J=6 Hz), 4.77 (1H, bs), 6.65 (1H, t, J=9 Hz), 6.90 (2H, d, J=9 Hz), 7.2–7.3 (4H, m). IR spectrum ν max (KBr) cm$^{-1}$: 3376, 2211, 1356, 1248. Mass spectrum m/z (EI): 256 (M$^+$), 121 (100%).

(2) Trifluoroacetic acid (1 ml) was added dropwise to a solution of 3-fluoro-4-[(4-methoxybenzyl)amino]benzonitrile (1.0 g, 3.9 mmol), obtained in Example 25(1), in anhydrous dichloromethane (20 ml) cooled to 0° C. with stirring. The resulting mixture was stirred at room temperature overnight. At the end of this time, the reaction mixture was poured into saturated aqueous sodium hydrogencarbonate solution at 0° C. The resulting mixture was partitioned between ethyl acetate and water. The organic layer was washed with saturated aqueous sodium chloride solution, dried over anhydrous magnesium sulfate and concentrated under reduced pressure. The residual oil was chromatographed on a silica gel column using ethyl acetate-hexane (1:6) as the eluant to afford 4-amino-3-fluorobenzonitrile (252 mg, yield 47%) as a pale orange solid which was recrystallized from ethyl acetate-hexane to give white powdery crystals. Melting point: 84° C.

NMR spectrum (400 MHz, CDCl$_3$) δ ppm: 4.23 (2H, bs), 6.76 (1H, t, J=9 Hz), 7.2–7.3 (2H, m). IR spectrum ν max (KBr) cm$^{-1}$: 3449, 3353, 2224, 1641. Mass spectrum m/z (EI): 136 (M$^+$, 100%)

(3) In the same manner as that described in Example 3(4), a reaction was carried out using 4-amino-3-fluorobenzonitrile (129 mg, 0.95 mmol), obtained in Example 25(2), trimethylaluminium (0.89 ml, 1.07M n-hexane solution, 0.95 mmol) and methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzoate (120 mg, 0.24 mmol), obtained in Example 12(1), and the reaction mixture was treated using a similar procedure to that described in Example 3(4) to afford the title compound (134 mg, yield 92%) as a white solid which was recrystallized from ethyl acetate-hexane to give white powdery crystals.

Melting point: 136° C. NMR spectrum (500 MHz, CDCl$_3$) δ ppm: 1.22 (3H, d, J=7 Hz), 3.36 (1H, q, J=7 Hz), 3.4–3.6 (1H, m), 3.76 (1H, t, J=11 Hz), 3.79 (1H, t, J=11 Hz), 4.42 (1H, ddd, J=11, 5, 2 Hz), 4.55 (1H, ddd, J=11, 5, 2 Hz), 4.85 (1H, d, J=14 Hz), 5.05 (1H, d, J=14 Hz), 5.05 (1H, s), 5.55 (1H, s), 6.7–6.8 (2H, m), 7.3–7.4 (1H, m), 7.45 (1H, d, J=12 Hz), 7.53 (1H, d, J=8 Hz), 7.66 (2H, d, J=8 Hz), 7.79 (2H, s), 7.91 (2H, d, J=8 Hz), 8.22 (1H, bd, J=4 Hz), 8.73 (1H, t, J=8 Hz). IR spectrum: ν max (KBr) cm$^{-1}$: 3435, 2232, 1686, 1520, 1139. Mass spectrum m/z (FAB): 610 (M$^+$+1). Specific rotation: $[\alpha]_D^{25}$ −61° (c=0.57, CHCl$_3$).

Example 26

N-(4-Cyanobenzyl)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzamide and cis isomer Thereof (Exemplification Compound Number 19-1)

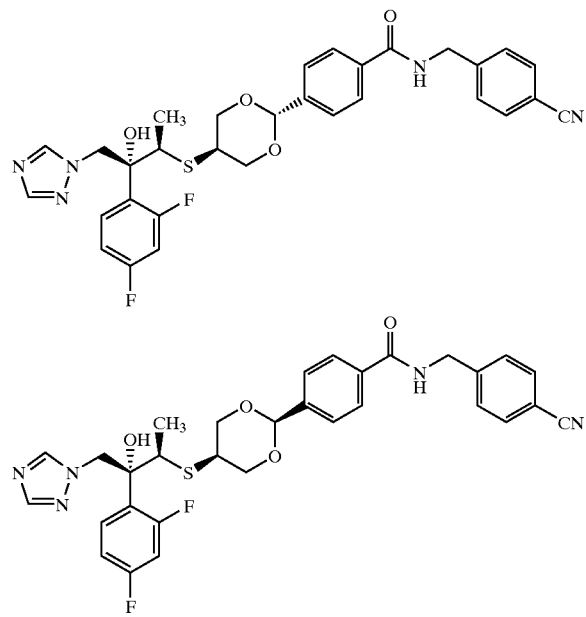

(1) In the same manner as that described in Example 2(1), a reaction was carried out using 4-cyanobenzylamine (329 mg, 2.5 mmol), described in J. Am. Chem. Soc., 81, 4328 (1959), N,N-diisopropylethylamine (0.91 ml, 5.2 mmol), 4-formylbenzoyl chloride (350 mg, 2.1 mmol) and 4-(dimethylamino)pyridine (a catalytic amount) and the reaction mixture was treated according to a similar procedure to that described in Example 2(1) to afford N-(4-cyanobenzyl)-4-formylbenzamide (308 mg, yield 56) as a white solid which was recrystallized from ethyl acetate to give white fluffy crystals.

Melting point: 170° C. NMR spectrum (270 MHz, CDCl$_3$) δ ppm: 4.74 (2H, d, J=6 Hz), 6.59 (1H, bs), 7.48 (2H, d, J=8 Hz), 7.65 (2H, d, J=8 Hz), 7.95 (2H, d, J=8 Hz), 7.99 (2H, d, J=8 Hz), 10.10 (1H, s). IR spectrum ν max (KBr) cm$^{-1}$: 3319, 2223, 1706, 1642, 1542. Mass spectrum m/z (EI): 264 (M$^+$), 133 (100%).

| Elemental analysis: | | | |
|---|---|---|---|
| Calculated for C$_{16}$H$_{12}$N$_2$O$_2$ | C:72.72 | H:4.58 | N:10.60 |
| Found | C:72.89 | H:4.83 | N:10.51. |

(2) In the same manner as that described in Example 1(2), a reaction was carried out using N-(4-cyanobenzyl)-4-formylbenzamide, obtained in Example 26(1) (200 mg, 0.76 mmol), (2R,3R)-2-(2,4-difluorophenyl)-3-[[1-(hydroxymethyl)-2-hydroxyethyl]thio]-1-(1H-1,2,4-triazol-1-yl)-2-butanol (237 mg, 0.66 mmol) and p-toluenesulfonic acid monohydrate (151 mg, 0.79 mmol) and the reaction mixture was treated using a similar procedure to that described in Example 1(2) to afford the trans isomer of the title compound (137 mg, yield 34%) as a white solid and the cis isomer (82 mg, yield 21%) as a white solid. The trans isomer was recrystallized from tetrahydrofuran-hexane to give white powdery crystals and the cis isomer was recrystallized from ethyl acetate to give white powdery cryatals.

Trans isomer: Melting point: 188° C. NMR spectrum (270 MHz, CDCl$_3$) δ ppm: 1.21 (3H, d, J=7 Hz), 3.36 (1H, q, J=7 Hz), 3.4–3.6 (1H, m), 3.75 (1H, t, J=11 Hz), 3.77 (1H, t, J=11 Hz), 4.40 (1H, ddd, J=11, 5, 2 Hz), 4.53 (1H, ddd, J=11, 5, 2 Hz), 4.72 (2H, d, J=6 Hz), 4.84 (1H, d, J=14 Hz), 5.04 (1H, s), 5.05 (1H, d, J=14 Hz), 5.52 (1H, s), 6.51 (1H, bt), 6.7–6.8 (2H, m), 7.3–7.5 (1H, m), 7.46 (2H, d, J=8 Hz), 7.59 (2H, d, J=8 Hz), 7.65 (2H, d, J=8 Hz), 7.79 (2H, s), 7.82 (2H, d, J=8 Hz). IR spectrum ν max (KBr) cm$^{-1}$: 3302, 2229, 1636, 1541, 1139. Mass spectrum m/z (FAB): 606 (M$^+$+1). Specific rotation: $[\alpha]_D^{25}$ −64° (c=0.50, CHCl$_3$).

Cis isomer: Melting point: 171° C. NMR spectrum (270 MHz, CDCl$_3$) δ ppm: 1.22 (3H, d, J=7 Hz), 3.20 (1H, t, J=2 Hz), 3.43 (1H, q, J=7 Hz), 4.2–4.5 (4H, m), 4.71 (2H, d, J=6 Hz), 4.86 (1H, d, J=14 Hz), 4.95 (1H, s), 5.15 (1H, d, J=14 Hz), 5.64 (1H, s), 6.52 (1H, bt, J=6 Hz), 6.6–6.9 (2H, m), 7.3–7.5 (1H, m), 7.45 (2H, d, J=8 Hz), 7.62 (2H, d, J=8 Hz), 7.64 (2H, d, J=8 Hz), 7.78 (2H, d, J=8 Hz), 7.79 (1H, s), 7.83 (1H, s). IR spectrum ν max (KBr) cm$^{-1}$: 3283, 2229, 1634, 1543, 1135. Mass spectrum m/z (FAB): 606 (M$^+$+1). Specific rotation: $[\alpha]_D^{25}$ −75° (c=0.53, CHCl$_3$).

Example 27

4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-N-(2-thiazolyl)benzamide and cis isomer Thereof (Exemplification Compound Number 20-1)

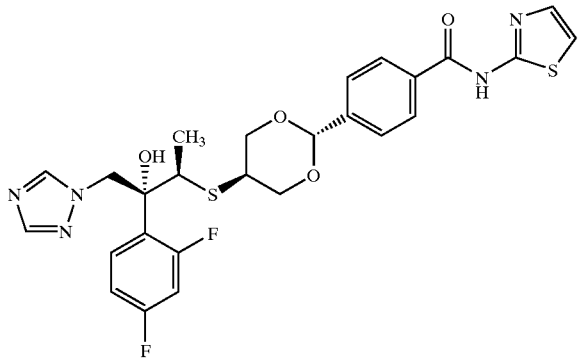

(1) In the same manner as that described in Example 2(1), a reaction was carried out using commercially available 2-aminothiazole (333 mg, 3.3 mmol), N,N-diisopropylethylamine (1.21 ml, 7.0 mmol), 4-formylbenzoyl chloride (468 mg, 2.8 mmol) and 4-(dimethylamino)pyridine (a catalytic amount) and the reaction mixture was treated according to a similar procedure to that described in Example 2(1) to afford 4-formyl-N-(2-thiazolyl)benzamide (355 mg, yield 55%) as a pale yellow solid which was recrystallized from ethyl acetate-hexane to give pale yellow powdery crystals.

Melting point: 189° C. NMR spectrum (270 MHz, CDCl$_3$) δ ppm: 7.02 (1H, d, J=4 Hz), 7.14 (1H, d, J=4 Hz), 8.05 (2H, d, J=8 Hz), 8.17 (2H, d, J=8 Hz), 10.15 (1H, s), 11.92 (1H, bs). IR spectrum ν max (KBr) cm$^{-1}$: 3149, 1691, 1671, 1549. Mass spectrum m/z (EI): 232 (M$^+$), 133 (100%).

(2) In the same manner as that described in Example 1(2), a reaction was carried out using 4-formyl-N-(2-thiazolyl)benzamide, obtained in Example 27(1) (200 mg, 0.86 mmol), (2R,3R)-2-(2,4-difluorophenyl)-3-[[1-(hydroxymethyl)-2-hydroxyethyl]thio]-1-(1H-1,2,4-triazol-1-yl)-2-butanol (270 mg, 0.75 mmol) and p-toluenesulfonic acid monohydrate (357 mg, 1.88 mmol) and the reaction mixture was treated using a similar procedure to that described in Example 1(2) to afford the trans isomer of the title compound (64 mg, yield 15%) as a white oil and the cis isomer (29 mg, yield 7%) as a colorless oil. The trans isomer was recrystallized from tetrahydrofuran-hexane to give white powdery crystals.

Trans isomer: Melting point: 108° C. NMR spectrum (270 MHz, CDCl$_3$) δ ppm: 1.22 (3H, d, J=7 Hz), 3.36 (1H, q, J=7 Hz), 3.4–3.6 (1H, m), 3.77 (1H, t, J=11 Hz), 3.79 (1H, t, J=11 Hz), 4.43 (1H, ddd, J=11, 5, 2 Hz), 4.56 (1H, ddd, J=11, 5, 2 Hz), 4.85 (1H, d, J=14 Hz), 5.05 (1H, s), 5.05 (1H, d, J=14 Hz), 5.56 (1H, s), 6.7–6.8 (3H, m), 7.01 (1H, d, J=4 Hz), 7.2–7.4 (1H, m), 7.31 (1H, d, J=4 Hz), 7.66 (2H, d, J=8 Hz), 7.80 (2H, s), 8.00 (2H, d, J=8 Hz). IR spectrum ν max (KBr) cm$^{-1}$: 3409, 1672, 1543, 1139. Mass spectrum m/z (FAB): 574 (M$^+$+1). Specific rotation: [α]$_D^{25}$ −30° (c=0.09, MeOH).

Cis isomer: Melting point: 171° C.

NMR spectrum (270 MHz, CDCl$_3$) δ ppm 1.23 (3H, d, J=7 Hz), 3.22 (1H, t, J=2 Hz), 3.47 (1H, q, J=7 Hz), 4.2–4.5 (4H, m), 4.87 (1H, d, J=14 Hz), 4.99 (1H, s), 5.16 (1H, d, J=14 Hz), 5.68 (1H, s), 6.6–6.8 (3H, m), 7.00 (1H, d, J=4 Hz), 7.30 (1H, d, J=4 Hz), 7.3–7.5 (1H, m), 7.69 (2H, d, J=8 Hz), 7.78 (1H, s), 7.80 (1H, s), 8.01 (2H, d, J=8 Hz). Mass spectrum m/z (FAB): 574 (M$^+$+1).

Example 28

N-(Benzothiazol-2-yl)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzamide and cis isomer Thereof (Exemplification Compound Number 39-1)

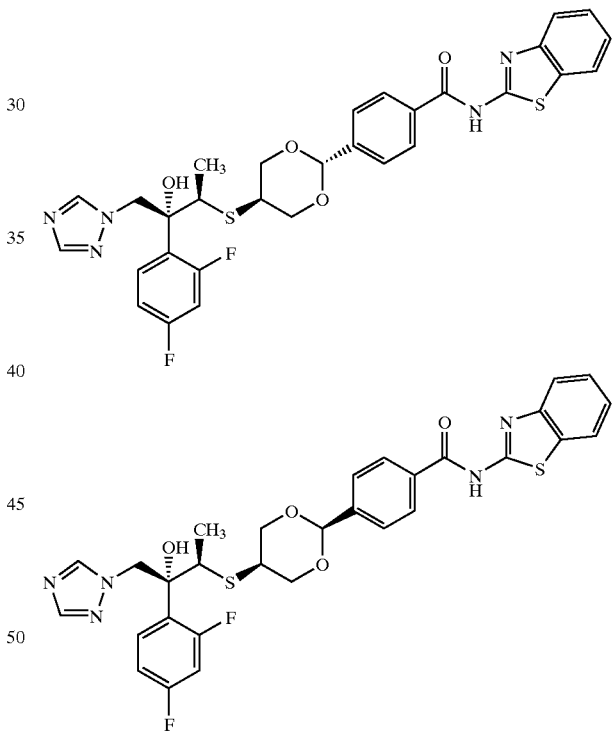

In the same manner as that described in Example 1(1), a solution of 4-formylbenzoyl chloride (561 mg, 3.33 mmol) in anhydrous tetrahydrofuran (6 ml) was added dropwise to a solution of commercially available 2-aminobenzothiazole (416 mg, 2.8 mmol) and triethylamine (0.62 ml, 4.4 mmol) in tetrahydrofuran cooled to 0° C. with stirring. The resulting mixture was stirred at 0° C. for two hours. At the end of this time, saturated aqueous sodium hydrogencarbonate solution was added to the reaction mixture in an ice bath. The resulting mixture was partitioned between ethyl acetate and water. The organic layer was washed sequentially with saturated aqueous sodium hydrogencarbonate solution, water and saturated aqueous sodium hydrogencarbonate solution, dried over anhydrous magnesium sulfate and then concentrated under reduced pressure. The crystalline residue was recrystallized from ethyl acetate to afford pale yellow powdery crystals (346 mg). In the same manner as that described in Example 3(3), a reaction was carried out using the yellow powdery crystals (300 mg) and (2R,3R)-2-(2,4-difluorophenyl)-3-[[1-(hydroxymethyl)-2-hydroxyethyl]thio]-1-(1H-1,2,4-triazol-1-yl)-2-butanol (258 mg, 0.72 mmol) and p-toluenesulfonic acid monohydrate (685 mg, 3.6 mmol) and the reaction mixture was treated according to a similar procedure to that described in Example 3(3) to give the trans isomer of the title compound (141 mg, yield 31%) as a colorless oil and the cis isomer (63 mg, yield 14%) as a colorless oil. The trans isomer was recrystallized from ethyl acetate-hexane to give white powdery crystals.

Trans isomer: Melting point 107° C. NMR spectrum (270 MHz, CDCl$_3$) δ ppm: 1.22 (3H, d, J=7 Hz), 3.36 (1H, q, J=7 Hz), 3.4–3.6 (1H, m), 3.76 (1H, t, J=11 Hz), 3.79 (1H, t, J=11 Hz), 4.42 (1H, ddd, J=11, 5, 2 Hz), 4.55 (1H, ddd, J=11, 5, 2 Hz), 4.85 (1H, d, J=14 Hz), 5.05 (1H, d, J=14 Hz), 5.06 (1H, s), 5.55 (1H, s), 6.7–6.8 (2H, m), 7.2–7.5 (3H, m), 7.67 (2H, d, J=8 Hz), 7.73 (1H, d, J=8 Hz), 7.80 (2H, s), 7.86 (1H, d, J=8 Hz), 8.01 (2H, d, J=8 Hz), 9.98 (1H, bs). IR spectrum ν max (KBr) cm$^{-1}$: 3409, 1678, 1539, 1139. Mass spectrum m/z (FAB): 624 (M$^+$+1). Specific rotation: $[\alpha]_D^{25}$ –64° (c=0.59, CHCl$_3$).

Cis isomer: NMR spectrum (270 MHz, CDCl$_3$) δ ppm: 1.23 (3H, d, J=7 Hz), 3.23 (1H, t, J=2 Hz), 3.44 (1H, q, J=7 Hz), 4.2–4.5 (4H, m), 4.87 (1H, d, J=14 Hz), 4.98 (1H, s), 5.15 (1H, d, J=14 Hz), 5.67 (1H, s), 6.6–6.8 (2H, m), 7.2–7.5 (3H, m), 7.70 (2H, d, J=8 Hz), 7.75 (1H, d, J=8 Hz), 7.78 (1H, s), 7.80 (1H, s), 7.86 (1H, d, J=8 Hz), 8.01 (2H, d, J=8 Hz), 9.97 (1H, bs). Mass spectrum m/z (FAB): 624 (M$^+$+1).

Example 29

4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-N-[(1-naphthyl)methyl]benzamide (Exemplification Compound Number 21-1)

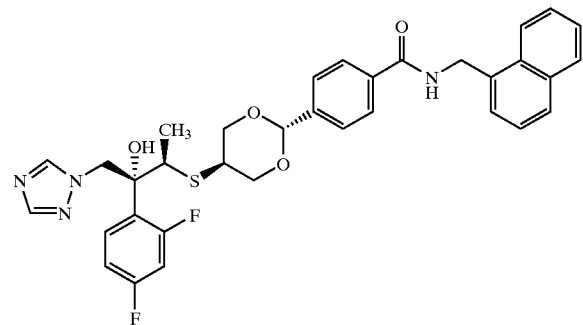

In the same manner as that described in Example 3(4), a reaction was carried out using commercially available 1-naphthylmethylamine (187 mg, 1.2 mmol), trimethylaluminium (1.1 ml, 1.07M n-hexane solution, 1.2 mmol) and methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzoate (150 mg, 0.30 mmol), obtained in Example 12(1), and the reaction mixture was treated using a similar procedure to that described in Example 3(4) to afford the title compound (170 mg, yield 91%) as a white solid which was recrystallized from dichloromethane-hexane to give white powdery crystals.

Melting point: 97° C. NMR spectrum (270 MHz, CDCl$_3$) δ ppm: 1.19 (3H, d, J=7 Hz), 3.34 (1H, q, J=7 Hz), 3.4–3.6 (1H, m), 3.73 (1H, t, J=11 Hz), 3.75 (1H, t, J=11 Hz), 4.38 (1H, ddd, J=11, 5, 2 Hz), 4.51 (1H, ddd, J=11, 5, 2 Hz), 4.83 (1H, d, J=14 Hz), 5.02 (1H, s), 5.03 (1H, d, J=14 Hz), 5.10 (2H, d, J=5 Hz), 5.48 (1H, s), 6.32 (1H, bt, J=5 Hz), 6.7–6.8 (2H, m), 7.2–7.4 (1H, m), 7.4–7.6 (6H, m), 7.7–7.8 (4H, m), 7.8–8.0 (2H, m), 8.0–8.2 (1H, m). IR spectrum ν max (KBr) cm$^{-1}$: 3328, 1646, 1539, 1139. Mass spectrum m/z (FAB): 631 (M$^+$+1). Specific rotation: $[\alpha]_D^{25}$ –61° (c=0.59, CHCl$_3$).

Example 30

4'-Carbamoyl-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide (Exemplification Compound Number 24-1)

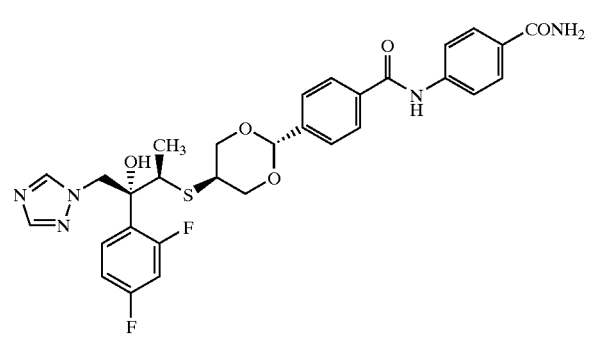

In the same manner as that described in Example 3(4), a reaction was carried out using commercially available p-aminobenzamide (162 mg, 1.2 mmol), trimethylaluminium (2.2 ml, 1.07M n-hexane solution, 2.4 mmol) and methyl 4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzoate (150 mg, 0.30 mmol), obtained in Example 12(1), and the reaction mixture was treated using a similar procedure to that described in Example 3(4) to afford the title compound (66 mg, yield 37%) as a white solid which was recrystallized from ethyl acetate-hexane to give pale orange powdery crystals.

Melting point: 230° C. NMR spectrum (400 MHz, DMSO-d$_6$) δ ppm: 1.11 (3H, d, J=7 Hz), 3.3–3.5 (1H, m), 3.58 (1H, q, J=7 Hz), 3.77 (2H, t, J=11 Hz), 4.3–4.5 (2H, m), 4.81 (1H, d, J=14 Hz), 4.91 (1H, d, J=14 Hz), 5.67 (1H, s), 6.02 (1H, s), 6.9–7.0 (1H, m), 7.1–7.3 (3H, m), 7.58 (2H, d, J=8 Hz), 7.68 (1H, s), 7.8–7.9 (5H, m), 8.00 (2H, d, J=8 Hz), 8.27 (1H, s), 10.48 (1H, s). IR spectrum ν max (KBr) cm$^{-1}$: 3386, 1659, 1526, 1139. Mass spectrum m/z (FAB): 610 (M$^+$+1). Specific rotation $[\alpha]_D^{25}$ –40° (c=0.18, MeOH).

Test Example 1

In Vitro Antifungal Activity

The antifungal activities of test compounds were assessed according to their minimum inhibitory concentrations (MICs) which were measured by the methods described below.

Liquid medium: RPMI1640 medium which was buffered to pH 7.0 (without an indicator) with 0.165M 3-(morpholino)propanesulfonic acid was used for *Candida albicans* and *Aspergillus fumigatus*. Yeast Nitrogen Base medium which was buffered to pH 7.0 with 0.165M 3-(morpholino)propanesulfonic acid was used for *Cryptococcus neoformans*.

Preparation of inoculation fungi solution: Each test fungi solution of *Candida albicans* and *Cryptococcus neoformans* was incubated on Sabouraud agar medium at 35° C. for 48 hours. About five colonies of the test fungi having 1 mm diameter were suspended in physiological saline and the transmittance of the suspension was adjusted to Macfarland 0.5 degree. A one thousand-fold diluted suspension of the resulting suspension was prepared by dilution with the liquid medium described above and was used for *Candida albicans*. A one hundred-fold diluted suspension of the resulting suspension was prepared by dilution with the liquid medium described above and was used for *Cryptococcus neoformans*. *Aspergillus fumigatus* was incubated on Potato dextrose agar at 35° C. for five days. Spores on the agar medium were collected with physiological saline containing 0.05% Tween 80 and the number of spores was adjusted to 2.5× $10^7$/ml using a blood cell counter. A one thousand-fold diluted suspension was prepared by dilution of the resulting spore suspension with the liquid medium described above and was used for *Aspergillus fumigatus*.

Preparation of test compound solution: Each test compound was dissolved in 100% dimethyl sulfoxide and serial two-fold dilutions of each compound were prepared with 100% dimethyl sulfoxide. The final concentration of dimethyl sulfoxide was adjusted to not greater than 1% by dilution with each liquid medium described above respectively.

Assessment method: Each diluted test compound (100 μl), the inoculation fungi solution (80 μl) and Alamar blue solution (20 μl) was sequentially added to each of wells of microtiter plate having 96 wells. The resulting mixture was incubated at 35° C. (30° C. for *Aspergillus fumigatus*). When the light absorbance at 570 nm of growth control exceeded 0.6, the MICs were determined. The MICs were defined as the lowest compound concentrations causing at least 80% growth inhibition ($IC_{80}$) compared with the control to which the test compound was not added.

The smaller the MIC value of the test compound, the more potent its antifungal activity.

The results of the comparison of compounds of formula (I) of this invention with the compound obtained in Example 40 (Comparative compound A) in Japanese Patent Application Publication No. Hei-8-333350 are shown in Table 2.

TABLE 2

*In vitro* antifungal activity

| Compound[1] | MIC value (μg/ml) | | |
|---|---|---|---|
| | *Candida albicans* SANK 51486 | *Cryptococcus neoformans* TIMM 1855 | *Aspergillus fumigatus* SANK 10569 |
| Example 1 | 0.016 | 0.063 | 0.125 |
| Example 3 | ≦0.008 | 0.063 | 0.063 |
| Example 9 | ≦0.008 | 0.25 | 2 |
| Example 23 | 0.016 | 0.25 | 0.5 |
| Example 26 | 0.016 | 0.25 | 0.25 |
| Comparative[2] compound (A) | 0.063 | 0.25 | 4 |

[1]The two substituents of the dioxane ring have trans configuration.
[2]Comparative compound (A) has the following formula:

1) The two substituents of the dioxane ring have trans configuration.

2) Comparative compound (A) has the following formula:

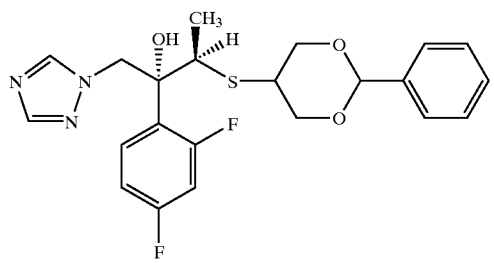

Formulation Example 1

Hard Capsule

The components shown below are filled into a standard two-component hard gelatin capsule, after which the capsule is washed and dried to give the desired hard capsule.

| | |
|---|---|
| Compound obtained in Example 1 | 100 mg |
| Lactose | 150 mg |
| Cellulose | 50 mg |
| Magnesium stearate | 6 mg |
| | 306 mg |

Formulation Example 2

Soft Capsule

A mixture of compound obtained in Example 1 in a digestible oil such as soy bean oil, cottonseed oil or olive oil is prepared and injected into gelatin using a pump to obtain a soft capsule containing 100 mg of the active ingredient which is then washed and dried to give the desired soft capsule.

Formulation Example 3

Tablet

The components shown below are mixed and wet granulation of the mixture is carried out using corn starch paste. The resulting granules are dried and compressed by a tablet machine to give the desired tablet (490 mg).

| | |
|---|---|
| Compound obtained in Example 1 | 100 mg |
| Colloidal silicon dioxide | 0.2 mg |
| Magnesium stearate | 5 mg |
| Microcrystalline cellulose | 275 mg |
| Starch | 11 mg |
| Lactose | 98.8 mg |
| | 490 mg |

If desired, the tablet can be coated with a suitable preparation coating.

The compounds (I) and pharmaceutically acceptable prodrugs thereof and pharmarceutically acceptable salts thereof in the present invention exhibit excellent antifungal activity.

These compounds are useful for the treatment and prevention of fungal infections and are used in methods for the prevention and/or treatment of a fungal infection in a warm-blooded animal by administering an effective amount of said compound(s) (I) or said prodrugs or salts thereof.

What is claimed is:

1. A compound of formula (I) or a pharmacologically acceptable prodrug or salt thereof:

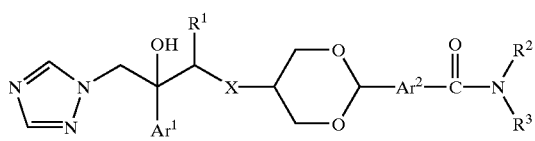

wherein:

$Ar^1$ is selected from the group consisting of a phenyl group and a phenyl group substituted with 1 to 3 substituents wherein said substituents are selected from the group consisting of a halogen atom and a trifluoromethyl group;

$Ar^2$ is selected from the group consisting of a phenylene group, a phenylene group substituted with 1 or 2 substituents wherein aid substituents are selected from the group consisting of a fluorine atom and a chlorine atom, a naphthylene group and a naphthylene group substituted with 1 or 2 substituents wherein said substituents are selected from the group consisting of a fluorine atom and a chlorine atom;

X is selected from the group consisting of a sulfur atom and a methylene group;

$R^1$ is selected from the group consisting of a hydrogen atom and a $C_{1-3}$ alkyl group;

$R^2$ is selected from the group consisting of a hydrogen atom and a $C_{1-3}$ alkyl group;

$R^3$ is selected from the group consisting of a $C_{6-10}$ aryl group, a $C_{6-10}$ aryl group substituted with 1 to 5 substituents selected from substituent group A, a heteroaryl group, a heteroaryl group substituted with 1 or 2 substituents selected from substituent group A, a $C_{7-14}$ aralkyl group, and a $C_{7-14}$ aralkyl group substituted with 1 to 5 substituents selected from substituent group A;

the substituent group A substituent(s) are selected from the group consisting of a $C_{1-6}$ alkyl group, a $C_{1-6}$ alkyl group substituted with 1 to 5 substituents wherein said substituents are selected from the group consisting of a halogen atom, a hydroxyl group, a cyano group and a $C_{1-6}$ alkoxy group, a $C_{1-6}$ alkoxy group, a $C_{1-6}$ alkoxy group substituted with 1 to 5 substituents wherein said substituents are selected from the group consisting of a halogen atom, a hydroxyl group, a cyano group and a $C_{1-6}$ alkoxy group, a $C_{1-6}$ alkanoyl group, a $C_{2-6}$ alkanoyl group substituted with 1 to 5 substituents wherein said substituents are selected from the group consisting of a halogen atom, a hydroxyl group, a cyano group and a $C_{1-6}$ alkoxy groupe, a $C_{1-6}$ alkanoyloxy group, a $C_{2-6}$ alkanoyloxy group substituted with 1 to 5 substituents wherein said substituents are selected from the group consisting of a halogen atom, a hydroxyl group, a cyano group and a $C_{1-6}$ alkoxy group, a halogen atom, a hydroxyl group, an amino group, a mercapto group, a carbamoyl group, a nitro group, a cyano group, a carboxyl group, a group of formula $—S(O)_nR^4$ wherein $R^4$ is selected from the group consisting of a $C_{1-6}$ alkyl group and a $C_{1-6}$ alkyl group substituted with 1 to 5 substituents wherein said substituents are selected from the group consisting of halogen atoms, and n represents 0, 1, or 2, a $C_{2-6}$ alkenyl group, a $C_{2-6}$ alkynyl group, a $C_{3-6}$ cycloalkyl group, and a $(C_{3-6}$ cycloalkyl)$C_{1-6}$ alkyl group.

2. A compound or a pharmacologically acceptable prodrug or salt thereof according to claim 1 wherein $Ar^1$ is selected from the group consisting of a phenyl group substituted with 1 or 2 substituents wherein said substituents are selected from the group consisting of a fluorine atom, a chlorine atom and a trifluoromethyl group.

3. A compound or a pharmacologically acceptable prodrug or salt thereof according to claim 1 wherein $Ar^1$ is a 2,4-difluorophenyl group.

4. A compound or a pharmacologically acceptable prodrug or salt thereof according to claim 1 wherein $Ar^2$ is a 1,4-phenylene group.

5. A compound or a pharmacologically acceptable prodrug or salt thereof according to claim 1 wherein X is a sulfur atom.

6. A compound or a pharmacologically acceptable prodrug or salt thereof according to claim 1 wherein X is a methylene group.

7. A compound or a pharmacologically acceptable prodrug or salt thereof according to claim 1 wherein $R^1$ is a $C_{1-3}$ alkyl group.

8. A compound or a pharmacologically acceptable prodrug or salt thereof according to claim 1 wherein $R^1$ is a methyl group.

9. A compound or a pharmacologically acceptable prodrug or salt thereof according to claim 1 wherein $R^2$ is a hydrogen atom.

10. A compound or a pharmacologically acceptable prodrug or salt thereof according to claim 1 wherein $R^3$ is selected from the group consisting of a $C_{6-10}$ aryl group and a $C_{6-10}$ aryl group substituted with 1 to 5 substituents selected from substituent group A.

11. A compound or a pharmacologically acceptable prodrug or salt thereof according to claim 1 wherein $R^3$ is selected from the group consisting of a phenyl group and a phenyl group substituted with 1 to 5 substituents selected from substituent group A.

12. A compound or a pharmacologically acceptable prodrug or salt thereof according to claim 1 wherein $R^3$ is a 5- or 6-membered aromatic heterocyclyl group having 1 or 2 nitrogen, oxygen or sulfur atoms or a bicyclic heterocyclyl group which is a 5- or 6-membered aromatic heterocyclyl group that has 1 or 2 nitrogen, oxygen or sulfur atoms and is fused to a benzene ring, and said heterocyclic group substituted with 1 or 2 substituents selected from substituent group A.

13. A compound or a pharmacologically acceptable prodrug or salt thereof according to claim 1 wherein $R^3$ is selected from the group consisting of a benzyl group and a benzyl group substituted with 1 or 2 substituents selected from substituent group A.

14. A compound or a pharmacologically acceptable prodrug or salt thereof according to claim 1 wherein substituent group A is selected from the group consisting of a $C_{1-6}$ alkyl group, a $C_{1-6}$ alkyl group substituted with 1 to 4 substituents wherein said substituents are selected from the group consisting of a halogen atom, a hydroxyl group and a cyano group, a $C_{1-6}$ alkoxy group, a $C_{1-6}$ alkoxy group substituted with 1 to 5 substituents wherein said substituents are selected from the group consisting of a halogen atom, a hydroxyl group and a cyano group, a $C_{1-6}$ alkanoyl group, a $C_{2-6}$ alkanoyl group substituted with 1 to 4 substituents wherein said substituents are selected from the group consisting of a halogen atom, a hydroxyl group and a cyano group, a $C_{1-6}$ alkanoyloxy group, a $C_{2-6}$ alkanoyloxy group substituted with 1 to 4 substituents wherein said substituents are selected from the group consisting of a halogen atom, a hydroxyl group and a cyano group, a halogen atom, a hydroxyl group, a carbamoyl group, a nitro group, a cyano group, a carboxyl group and a group of formula —S(O)$_n$R$^4$ wherein R$^4$ is selected from the group consisting of a $C_{1-6}$ alkyl group and a $C_{1-6}$ alkyl group substituted with 1 to 5 substituents wherein said substituents are selected from the group consisting of halogen atoms; and n represents 0, 1, or 2.

15. A compound or a pharmacologically acceptable prodrug or salt thereof according to claim 1 wherein substituent group A is selected from the group consisting of a $C_{1-3}$ alkyl group a $C_{1-4}$ alkyl group substituted with 1 to 4 substituents wherein said substituents are selected from the group consisting of a fluorine atom, a chlorine atom, a hydroxyl group and a cyano group, a $C_{1-3}$ alkoxy group, a $C_{1-4}$ alkoxy group substituted with 1 to 5 substituents wherein said substituents are selected from the group consisting of a fluorine atom, a chlorine atom and a hydroxyl group, a $C_{1-3}$ alkanoyl group, a $C_{2-4}$ alkanoyl group substituted with 1 to 3 substituents wherein said substituents are selected from the group consisting of a fluorine atom and a hydroxyl group, a $C_{1-3}$ alkanoyloxy group, a $C_{2-6}$ alkanoyloxy group substituted with 1 to 4 substituents wherein said substituents are selected from the group consisting of hydroxyl group, a halogen atom, a hydroxyl group, a carbamoyl group, a nitro group, a cyano group, a carboxyl group and a group of formula —S(O)$_n$R$^4$ wherein R$^4$ is selected from the group consisting of a $C_{1-3}$ alkyl group and a $C_{1-3}$ alkyl group substituted with 1 to 5 substituents wherein said substituents are selected from the group consisting of fluorine atoms; and n represents 0, 1, or 2.

16. A compound or a pharmacologically acceptable prodrug or salt thereof according to claim 1 wherein substituent group A is selected from the group consisting of a methyl group, a trifluoromethyl group, a cyanomethyl group, a trifluoromethoxy group, a tetrafluoropropoxy group, an acetyl group, an acetoxy group, a fluorine atom, a chlorine atom, an iodine atom, a hydroxyl group, a carbamoyl group, a nitro group, a cyano group, a carboxyl group, a trifluoromethylthio group, a methanesulfonyl group and a trifluoromethanesulfonyl group.

17. A compound or a pharmacologically acceptable prodrug or salt thereof according to claim 1 wherein:
   Ar$^1$ is selected from the group consisting of a phenyl group substituted with 1 or 2 substituents wherein said substituents are selected from the group consisting of a fluorine atom, a chlorine atom and a trifluoromethyl group;
   Ar$^2$ is a 1,4-phenylene group;
   X is a sulfur atom;
   R$^1$ is a $C_{1-3}$ alkyl group;
   R$^2$ is a hydrogen atom;
   R$^3$ is selected from the group consisting of a $C_{6-10}$ aryl group and a $C_{6-10}$ aryl group substituted with 1 to 5 substituents selected from substituent group A; and
   substituent group A is selected from a $C_{1-6}$ alkyl group, a $C_{1-6}$ alkyl group substituted with 1 to 4 substituents wherein said substituents are selected from the group consisting of a halogen atom, a hydroxyl group and a cyano group, a $C_{1-6}$ alkoxy group, a $C_{1-6}$ alkoxy group substituted with 1 to 5 substituents wherein said substituents are selected from the group consisting of a halogen atom, a hydroxyl group and a cyano group, a $C_{1-6}$ alkanoyl group, a $C_{2-6}$ alkanoyl group substituted with 1 to 4 substituents wherein said substituents are selected from the group consisting of a halogen atom, a hydroxyl group and a cyano group, a $C_{1-6}$ alkanoyloxy group, a $C_{2-6}$ alkanoyloxy group substituted with 1 to 4 substituents wherein said substituents are selected from the group consisting of a halogen atom, a hydroxyl group and a cyano group, a halogen atom, a hydroxyl group, a carbamoyl group, a nitro group, a cyano group, a carboxyl group and a group of formula —S(O)$_n$R$^4$ wherein R$^4$ is selected from the group consisting of a $C_{1-6}$ alkyl group and a $C_{1-6}$ alkyl group substituted with 1 to 5 substituents wherein said substituents are selected from the group consisting of halogen atoms; and n represents 0, 1, or 2.

18. A compound or a pharmacologically acceptable prodrug or salt thereof according to claim 1 wherein:
   Ar$^1$ is selected from the group consisting of a phenyl group substituted with 1 or 2 substituents wherein said substituents are selected from the group consisting of a fluorine atom, a chlorine atom and a trifluoromethyl group;
   Ar$^2$ is a 1,4-phenylene group;
   X is a methylene group;
   R$^1$ is a $C_{1-3}$ alkyl group;
   R$^2$ is a hydrogen atom;
   R$^3$ is selected from the group consisting of a $C_{6-10}$ aryl group and a $C_{6-10}$ aryl group substituted with 1 to 5 substituents selected from substituent group A; and
   substituent group A is selected from a $C_{1-6}$ alkyl group, a $C_{1-6}$ alkyl group substituted with 1 to 4 substituents wherein said substituents are selected from the group consisting of a halogen atom, a hydroxyl group and a cyano group, a $C_{1-6}$ alkoxy group, a $C_{1-6}$ alkoxy group substituted with 1 to 5 substituents wherein said substituents are selected from the group consisting of a halogen atom, a hydroxyl group and a cyano group, a $C_{1-6}$ alkanoyl group, a $C_{2-6}$ alkanoyl group substituted with 1 to 4 substituents wherein said substituents are selected from the group consisting of a halogen atom, a hydroxyl group and a cyano group, a $C_{1-6}$ alkanoyloxy group, a $C_{2-6}$ alkanoyloxy group substituted with 1 to 4 substituents wherein said substituents are selected from the group consisting of a halogen atom, a hydroxyl group and a cyano group, a halogen atom, a hydroxyl group, a carbamoyl group, a nitro group, a cyano group, a carboxyl group and a group of formula —S(O)$_n$R$^4$ wherein R$^4$ is selected from the group consisting of a $C_{1-6}$ alkyl group and a $C_{1-6}$ alkyl group substituted with 1 to 5 substituents wherein said substituents are selected from the group consisting of halogen atoms; and n represents 0, 1, or 2.

19. A compound or a pharmacologically acceptable prodrug or salt thereof according to claim 1 wherein:
   Ar$^1$ is a 2,4-difluoropheny group;
   Ar$^2$ is a 1,4-phenylene group;
   X is a sulfur atom;
   R$^1$ is a methyl group;
   R$^2$ is a hydrogen atom;
   R$^3$ is selected from the group consisting of a phenyl group and a phenyl group substituted with 1 to 5 substituents selected from Substituent group A; and substituent group A is selected from a $C_{1-3}$ alkyl group, a $C_{1-4}$ alkyl group substituted with 1 to 4 substituents wherein said substituents are selected from the group consisting of a fluorine atom, a chlorine atom, a hydroxyl group and a cyano group, a $C_{1-3}$ alkoxy group, a $C_{1-4}$ alkoxy group substituted with 1 to 5 substituents wherein said substituents are selected from the group consisting of a fluorine atom, a chlorine atom and a hydroxyl group, a $C_{1-3}$ alkanoyl group, a $C_{2-4}$ alkanoyl group substituted with 1 to 3 substituents wherein said substituents are selected from the group consisting of a fluorine atom and a hydroxyl group, a $C_{1-3}$ alkanoyloxy group, a $C_{2-6}$ alkanoyloxy group substituted with 1 to 4 substituents wherein said substituents are selected from the group consisting of hydroxyl groups, a halogen atom, a hydroxyl group, a carbamoyl group, a nitro group, a cyano group, a carboxyl group and a group of formula —S(O)$_n$R$^4$ wherein R$^4$ is selected from the group consisting of a $C_{1-3}$ alkyl group and a $C_{1-3}$ alkyl group substituted with 1 to 5 substituents wherein said substituents are selected from the group consisting of fluorine atoms; and n represents 0, 1, or 2.

20. A compound or a pharmacologically acceptable prodrug or salt thereof according to claim 1 wherein:

Ar$^1$ is a 2,4-difluorophenyl group;

Ar$^2$ is a 1,4-phenylene group;

X is a methylene group;

R$^1$ is a methyl group;

R$^2$ is a hydrogen atom;

R$^3$ is selected from the group consisting of a phenyl group and a phenyl group substituted with 1 to 5 substituents selected from substituent group A; and substituent group A is selected from a $C_{1-3}$ alkyl group, a $C_{1-4}$ alkyl group substituted with 1 to 4 substituents wherein said substituents are selected from the group consisting of a fluorine atom, a chlorine atom, a hydroxyl group and a cyano groups, a $C_{1-3}$ alkoxy group, a $C_{1-4}$ alkoxy group substituted with 1 to 5 substituents wherein said substituents are selected from the group consisting of a fluorine atom, a chlorine atom and a hydroxyl group, a $C_{1-3}$ alkanoyl group, a $C_{2-4}$ alkanoyl group substituted with 1 to 3 substituents wherein said substituents are selected from the group consisting of a fluorine atom and a hydroxyl group, a $C_{1-3}$ alkanoyloxy group, a $C_{2-6}$ alkanoyloxy group substituted with 1 to 4-substituents wherein said substituents are selected from the group consisting of hydroxyl groups, a halogen atom, a hydroxyl group, a carbamoyl group, a nitro group, a cyano group, a carboxyl group and a group of formula —S(O)$_n$R$^4$ wherein R$^4$ is selected from the group consisting of a $C_{1-3}$ alkyl group and a $C_{1-3}$ alkyl group substituted with 1 to 5 substituents wherein said substituents are selected from the group consisting of fluorine atoms; and n represents 0, 1, or 2.

21. A compound or a pharmacologically acceptable prodrug or salt thereof, said compound being selected from the group consisting of:

4-[5-[[2-(2,4-difluorophenyl)-2-hydroxy-1-methyl-3-(1H-1,2,4-triazol-1-yl)propyl]thio]-1,3-dioxan-2-yl]-4'-(2,2,3,3-tetrafluoropropoxy)benzanilide, 4-[5-[3-(2,4-difluorophenyl)-3-hydroxy-2-methyl-4-(1H-1,2,4-triazol-1-yl)butyl]-1,3-dioxan-2-yl]-4'-(2,2,3,3-tetrafluoropropoxy)benzanilide, 4'-cyano-4-[5-[[2-(2,4-difluorophenyl)-2-hydroxy-1-methyl-3-(1H-1,2,4-triazol-1-yl)propyl]thio]-1,3-dioxan-2-yl]benzanilide, 4'-cyano-4-[5-[3-(2,4-difluorophenyl)-3-hydroxy-2-methyl-4-(1H-1,2,4-triazol-1-yl)butyl]-1,3-dioxan-2-yl]benzanilide, 4'-chloro-4-[5-[(2-(2,4-difluorophenyl)-2-hydroxy-1-methyl-3-(1H-1,2,4-triazol-1-yl)propyl]thio)-1,3-dioxan-2-yl]benzanilide, 4'-chloro-4-[5-[3-(2,4-difluorophenyl)-3-hydroxy-2-methyl-4-(1H-1,2,4-triazol-1-yl)butyl]-1,3-dioxan-2-yl]benzanilide, 4-[5-[[2-(2,4-difluorophenyl)-2-hydroxy-1-methyl-3-(1H-1,2,4-triazol-1-yl)propyl]thio]-1,3-dioxan-2-yl]-4'-fluorobenzanilide, 4-[5-[3-(2,4-difluorophenyl)-3-hydroxy-2-methyl-4-(1H-1,2,4-triazol-1-yl)butyl]-1,3-dioxan-2-yl]-4'-fluorobenzanilide, 4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethyl)benzanilide, 4-[5-[3-(2,4-difluorophenyl)-3-hydroxy-2-methyl-4-(1H-1,2,4-triazol-1-yl)butyl]-1,3-dioxan-2-yl]-4'-(trifluoromethyl)benzanilide, 4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethoxy)benzanilide, 4-[5-[3-(2,4-difluorophenyl)-3-hydroxy-2-methyl-4-(1H-1,2,4-triazol-1-yl)butyl]-1,3-dioxan-2-yl]-4'-(trifluoromethoxy)benzanilide, 4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethylthio)benzanilide, 4-[5-[3-(2,4-difluorophenyl)-3-hydroxy-2-methyl-4-(1H-1,2,4-triazol-1-yl)butyl]-1,3-dioxan-2-yl]-4'-(trifluoromethylthio)benzanilide, 4-[5-[[2-(2,4-difluorophenyl)-2-hydroxy-1-methyl-3-(1H-1,2,4-triazol-1-yl)propyl]thio]-1,3-dioxan-2-yl]-4'-methylbenzanilide, 4-[5-[3-(2,4-difluorophenyl)-3-hydroxy-2-methyl-4-(1H-1,2,4-triazol-1-yl)butyl]-1,3-dioxan-2-yl]-4'-methylbenzanilide, 3'-chloro-4'-cyano-4-[5-[[2-(2,4-difluorophenyl)-2-hydroxy-1-methyl-3-(1H-1,2,4-triazol-1-yl)propyl]thio]-1,3-dioxan-2-yl]benzanilide, 3'-chloro-4'-cyano-4-[5-[3-(2,4-difluorophenyl)-3-hydroxy-2-methyl-4-(1H-1,2,4-triazol-1-yl)butyl]-1,3-dioxan-2-yl]benzanilide, 4'-cyano-2'-fluoro-4-[5-[[2-(2,4-difluorophenyl)-2-hydroxy-1-methyl-3-(1H-1,2,4-triazol-1-yl)propyl]thio]-1,3-dioxan-2-yl]benzanilide, 4'-cyano-2'-fluoro-4-[5-[3-(2,4-difluorophenyl)-3-hydroxy-2-methyl-4-(1H-1,2,4-triazol-1-yl)butyl]-1,3-dioxan-2-yl]benzanilide, 4-[5-([2-(2,4-difluorophenyl)-2-hydroxy-1-methyl-3-(1H-1,2,4-triazol-1-yl)propyl]thio]-1,3-dioxan-2-yl]-4'-hydroxybenzanilide, 4-[5-[3-(2;4-difluorophenyl)-3-hydroxy-2-methyl-4-(1H-1,2,4-triazol-1-yl)butyl]-1,3-dioxan-2-yl]-4'-hydroxybenzanilide, 4-[5-[[2-(2,4-difluorophenyl)-2-hydroxy-1-methyl-3-(1H-1,2,4-triazol-1-yl)propyl]thio]-1,3-dioxan-2-yl]-4'-methanesulfonyl)benzanilide, 4-[5-[3-(2,4-difluorophenyl)-3-hydroxy-2-methyl-4-(1H-1,2,4-triazol-1-yl)butyl]-1,3-dioxan-2-yl]-4'-(methanesulfonyl)benzanilide, 4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethanesulfonyl)benzanilide, 4-[5-[3-(2,4-difluorophenyl)-3-hydroxy-2-methyl-4-(1H-1,2,4-triazol-1-yl)butyl]-1,3-dioxan-2-yl]-4'-(trifluoromethanesulfonyl)benzanilide, 2',4'-dichloro-4-[5-[[2-(2,4-difluorophenyl)-2-hydroxy-1-methyl-3-(1H-1,2,4-triazol-1-yl)propyl]thio]-1,3-dioxan-2-yl]benzanilide, 2',4'-dichloro-4-[5-[3-(2,4-difluorophenyl)-3-hydroxy-2-methyl-4-(1H-1,2,4-triazol-1-yl)butyl]-1,3-dioxan-2-yl]benzanilide, 2'-chloro-4-[5-[[2-(2,4-difluorophenyl)-2-hydroxy-1-methyl-3-(1H-1,2,4-triazol-1-yl)propyl]thio]-1,3-dioxan-2-yl]-4'-(trifluoromethyl)benzanilide, and 2'-chloro-4-[5-[3-(2,4-difluorophenyl)-3-hydroxy-2-methyl-4-(1H-1,2,4-triazol-1-yl)butyl]-1,3-dioxan-2-yl]-4'-(trifluoromethyl)benzanilide.

22. A compound or a pharmacologically acceptable prodrug or salt thereof, said compound being selected from the group consisting of:

4'-cyano-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide, 4'-cyano-4-[trans-5-[(2S,3R)-3-(2,4-difluorophenyl)-3-hydroxy-2-methyl-4-(1H-1,2,4-triazol-1-yl)butyl]-1,3-dioxan-2-yl]benzanilide, 4'-chloro-4-[trans-5-[[(1R,2R)-2-(2,4-difluorophenyl)-2-hydroxy-1-methyl-3-(1H-1,2,4-triazol-1-yl)propyl)thio]-1,3-dioxan-2-yl]benzanilide, and 4'-chloro-4-[trans-5-[(2S,3R)-3-(2,4-difluorophenyl)-3-hydroxy-2-methyl-4-(1H-1,2,4-triazol-1-yl)butyl]-1,3-dioxan-2-yl]benzanilide.

23. A compound or a pharmacologically acceptable salt thereof according to claim 22, wherein said compound is 4'-cyano-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide.

24. A compound or a pharmacologically acceptable salt thereof according to claim 22, wherein said compound is 4'-cyano-4-[trans-5-[(2S,3R)-3-(2,4-difluorophenyl)-3-hydroxy-2-methyl-4-(1H-1,2,4-triazol-1-yl)butyl]-1,3-dioxan-2-yl]benzanilide.

25. A compound or a pharmacologically acceptable salt thereof according to claim 22, wherein said compound is 4'-chloro-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]benzanilide.

26. A compound or a pharmacologically acceptable salt thereof according to claim 22, wherein said compound is 4'-chloro-4-(trans-5-((2S,3R)-3-(2,4-difluorophenyl)-3-hydroxy-2-methyl-4-(1H-1,2,4-triazol-1-yl)butyl]-1,3-dioxan-2-yl]benzanilide.

27. An amide-type triazole compound of formula (I) or a pharmacologically acceptable salt thereof:

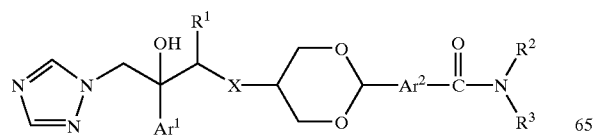

(I)

wherein $Ar^1$ represents a phenyl group or a phenyl group substituted with 1 to 3 substituents wherein said substituents are selected from a halogen atom and a trifluoromethyl group;

$Ar^2$ represents a phenylene group, a phenylene group substituted with 1 or 2 substituents wherein said substituents are selected from a fluorine atom and a chlorine atom, a naphthylene group or a naphthylene group substituted with 1 or 2 substituents wherein said substituents are selected from a fluorine atom and a chlorine atom;

X represents a sulfur atom or a methylene group;

$R^1$ represents a hydrogen atom or a $C_{1-3}$ alkyl group;

$R^2$ represents a hydrogen atom or a $C_{1-3}$ alkyl group;

$R^3$ represents a $C_{6-10}$ aryl group, a $C_{6-10}$ aryl group substituted with 1 to 5 substituents selected from substituent group A, a heteroaryl group, a heteroaryl group substituted with 1 or 2 substituents selected from substituent group A, a $C_{7-14}$ aralkyl group, or a $C_{7-14}$ aralkyl group substituted with 1 to 5 substituents selected from substituent group A;

substituent group A comprises a $C_{1-6}$ alkyl group, a $C_{1-6}$ alkyl group substituted with 1 to 5 substituents wherein said substituents are selected from a halogen atom, a hydroxyl group, and a cyano group, a $C_{1-6}$ alkoxy group, a $C_{1-6}$ alkoxy group substituted with 1 to 5 substituents wherein said substituents are selected from a halogen atom, a hydroxyl group, and a cyano group, a $C_{1-6}$ alkanoyl group, a $C_{2-6}$ alkanoyl group substituted with 1 to 5 substituents wherein said substituents are selected from a halogen atom, a hydroxyl group, and a cyano group, a $C_{1-6}$ alkanoyloxy group, a $C_{2-6}$ alkanoyloxy group substituted with 1 to 5 substituents wherein said substituents are selected from a halogen atom, a hydroxyl group, and a cyano group, a halogen atom, a hydroxyl group, an amino group, a mercapto group, a carbamoyl group, a nitro group, a cyano group, a carboxyl group, a group of formula $-S(O)_nR^4$ wherein $R^4$ represents a $C_{1-6}$ alkyl group or a $C_{1-6}$ alkyl group substituted with 1 to 5 substituents wherein said substituents are selected from halogen atoms, and n represents 0, 1, or 2.

28. A pharmaceutical composition comprising a pharmaceutically acceptable carrier and a compound or a pharmacologically acceptable prodrug or salt thereof according to any one of claims 1 to 27.

29. A method for the treatment of a fungal infection in a warm-blooded animal, which comprises administering to said warm-blooded animal in need of said prevention or treatment an effective amount of a compound or a pharmacologically acceptable prodrug or salt thereof according to any one claims 1 to 27.

30. A method according to claim 29, wherein said warm-blooded animal is a human.

* * * * *